US008609610B2

(12) United States Patent
Kisselev et al.

(10) Patent No.: US 8,609,610 B2
(45) Date of Patent: *Dec. 17, 2013

(54) INHIBITORS OF THE TRYPSIN-LIKE SITE OF THE PROTEASOME AND METHODS OF USE THEREOF

(71) Applicants: Trustees of Dartmouth College, Hanover, NH (US); Leiden University, Leiden (NL)

(72) Inventors: Alexei Kisselev, West Lebanon, NH (US); Dmitry V. Filippov, Leiden (NL); Herman Overkleeft, Leiden (NL)

(73) Assignees: Trustees of Dartmouth College, Hanover, NH (US); Leiden University (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,979

(22) Filed: Dec. 21, 2012

(65) Prior Publication Data

US 2013/0102527 A1    Apr. 25, 2013

Related U.S. Application Data

(63) Continuation-in-part of application No. 13/399,189, filed on Feb. 17, 2012, now Pat. No. 8,455,431.

(60) Provisional application No. 61/444,164, filed on Feb. 18, 2011.

(51) Int. Cl.
| | | |
|---|---|---|
| *A61P 33/00* | (2006.01) |
| *A61K 38/00* | (2006.01) |
| *A61P 35/00* | (2006.01) |
| *A61K 38/55* | (2006.01) |
| *C07K 14/81* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/06* | (2006.01) |

(52) U.S. Cl.
USPC ........... 514/4.6; 530/330; 530/331; 514/19.3; 514/20.1

(58) Field of Classification Search
None
See application file for complete search history.

(56) References Cited

U.S. PATENT DOCUMENTS 8,455,431 B2    6/2013  Kisselev et al. ............. 514/4.6
2007/0293465 A1*  12/2007  Shenk et al. ............... 514/183

FOREIGN PATENT DOCUMENTS

WO    WO 2005/076886    8/2005

OTHER PUBLICATIONS

Verdoes M "Chemical Tools to Probe the Proteasome" Doctoral Thesis, Leiden University. Published Dec. 19, 2008.*
Mirabella et al "Specific Cell-Permeable Inhibitor of Proteasome Trypsin-like Sites Selectively Sensitizes Myeloma Cells to Bortezomib and Carfilzomib" Chem & Biol 18:608-618. Published May 17, 2011.*
Baldisserotto et al. "Glutamine Vinyl Ester Proteasome Inhibitors Selective for Trypsin-like ($\beta$2) Subunit" European Journal of Medicinal Chemistry 2007 42:586-592.
Baldisserotto et al. "N-terminal-prolonged Vinyl Ester-based Peptides as Selective Proteasome $\beta$1 Subunit Inhibitors" Bioorganic & Medicinal Chemistry 2009 17:5535-5540.
Britton et al. "Selective Inhibitor of Proteasome's Caspase-like Sites Sensitizes Cells to Specific Inhibition of Chymotrypsin-like Sites" Chemistry & Biology 2009 16:1278-1289.
Groll et al. "Crystal Structure of Epoxomicin:20S Proteasome Reveals a Molecular Basis for Selectivity of $\alpha'$, $\beta'$-Epoxyketone Proteasome Inhibitors" Journal of the American Chemical Society 2000 122:1237-1238.
Groll et al. "Probing Structural Determinants Distal to the Site of Hydrolysis that Control Substrate Specificity of the 20S Proteasome" Chemistry & Biology 2002 9:655-662.
Groll, M. and Huber, R. "Inhibitors of the Eukaryotic 20S Proteasome Core Particle: a Structural Approach" Biochimica et Biophysica Acta 2004 1695:33-44.
Harris et al. "Substrate Specificity of the Human Proteasome" Chemistry & Biology 2001 8:1131-1141.
Kim et al. "Proteasome Inhibition by the Natural Products Epoxomicin and Dihydroeponemycin: Insights into Specificity and Potency" Bioorganic & Medicinal Chemistry Letters 1999 9:3335-3340.
Kisselev, A. F. "Joining the Army of Proteasome Inhibitors" Chemistry & Biology 2008 15:419-421.
Kisselev, A. F. And Goldberg, A. L. "Monitoring Activity and Inhibition of 26S Proteasomes with Fluorogenic Peptide Substrates" Methods in Enzymology 2005 398:364-378.
Kisselev, A. F. and Goldberg, A. L. "Proteasome Inhibitors: from Research Tools to Drug Candidates" Chemistry & Biology 2001 8:739-758.
Loidl et al. "Bifunctional Inhibitors of the Trypsin-like Activity of Eukaryotic Proteasomes" Chemistry & Biology 1999 6(4):197-204.
Marastoni et al. "Peptidyl Vinyl Ester Derivatives: New Class of Selective Inhibitors of Proteasome Trypsin-like Activity" Journal of Medicinal Chemistry 2005 48:5038-5042.
McCormack et al. "Kinetic Studies of the Branched Chain Amino Acid Preferring Peptidase Activity of the 20S Proteasome: Development of a Continuous Assay and Inhibition by Tripeptide Aldehydes and *clasto*-Lactacystin $\beta$-Lactone" Biochemistry 1998 37:7792-7800.

(Continued)

*Primary Examiner* — Cecilia J Tsang
*Assistant Examiner* — Zachary J. Miknis
(74) *Attorney, Agent, or Firm* — Licata & Tyrrell, P.C.

(57) ABSTRACT

The present invention is an inhibitor of the trypsin-like $\beta$2/$\beta$2i sites of the proteasome. The inhibitor is characterized as being a peptide-based epoxyketone or vinyl sulfone that contains an arginine or 4-aminomethylene-L-phenylalanine at the C-terminus (i.e., at the P1 position). Methods for using the inhibitor to inhibit the activity of the $\beta$2/$\beta$2i site of a proteasome and treat a proteasome-mediated disease or condition are also described.

18 Claims, 2 Drawing Sheets

(56) References Cited

OTHER PUBLICATIONS

Nazif, T. and Bogyo, M. "Global Analysis of Proteasomal Substrate Specificity Using Positional-scanning Libraries of Covalent Inhibitors" Proceedings of the National Academy of Sciences USA 2001 98(6):2967-2972.

Ovaa et al. "Chemistry in Living Cells: Detection of Active Proteasomes by a Two-Step Labeling Strategy" Angewandte Chemie 2003 42:3626-3629.

Portaro et al. "Design of Kallidin-releasing Tissue Kallikrein Inhibitors Based on the Specificities of the Enzyme's Binding Subsites" Biochemical Journal 1997 323:167-171.

Screen et al. "Nature of Pharmacophore Influences Active Site Specificity of Proteasome Inhibitors" The Journal of Biological Chemistry 2010 285(51):40125-40134.

Van Swieten et al. "Bioorthogonal Organic Chemistry in Living Cells: Novel Strategies for Labeling Biomolecules" Organic & Biomolecular Chemistry 2005 3:20-27.

Verdoes et al. "Chemical Tools to Study the Proteasome" European Journal of Organic Chemistry 2009 3301-3313.

Verdoes, M. "Chemical Tools to Probe the Proteasome" Doctoral Thesis, Leiden University. Dec. 19, 2008.

Zhou et al. "Design and Synthesis of an Orally Bioavailable and Selective Peptide Epoxyketone Proteasome Inhibitor (PR-047)" Journal of Medicinal Chemistry 2009 52:3028-3038.

Office Communication dated Oct. 1, 2012 from U.S. Appl. No. 13/399,189, filed Feb. 17, 2012.

\* cited by examiner

SEQUENCE LISTING

```
<160> NUMBER OF SEQ ID NOS: 25

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with vinyl sulfone warhead.
<220> FEATURE:
<221> NAME/KEY: MOD_RES
<222> LOCATION: (4)..(4)
<223> OTHER INFORMATION: ACETYLATION

<400> SEQUENCE: 1

Asn Leu Arg Tyr
1

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Arg or aminosubstituted phenylalanine
      derivative. Xaa is modified with a epoxyketone or vinyl sulfone
      warhead.
<220> FEATURE:
<221> NAME/KEY: MISC_FEATURE
<222> LOCATION: (2)..(2)
<223> OTHER INFORMATION: Xaa is Leu or Ser.
<220> FEATURE:
<221> NAME/KEY: MISC_FEATURE
<222> LOCATION: (3)..(3)
<223> OTHER INFORMATION: Xaa is Leu, Val, Ser, Arg, His, Lys, Phe or an
      aminosubstituted phenylalanine derivative.
<220> FEATURE:
<221> NAME/KEY: MISC_FEATURE
<222> LOCATION: (4)..(4)
<223> OTHER INFORMATION: Xaa is present or absent and when present is
      Phe. Xaa can further include a capping group

<400> SEQUENCE: 2

Xaa Xaa Xaa Xaa
1

<210> SEQ ID NO 3
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with epoxyketone warhead.
<220> FEATURE:
<221> NAME/KEY: MOD_RES
<222> LOCATION: (4)..(4)
<223> OTHER INFORMATION: Aza-Glycine
```

```
<400> SEQUENCE: 3

Arg Leu Leu Gly
1

<210> SEQ ID NO 4
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-aminomethylene-L-phenylalanine modified with
      vinyl sulfone warhead.
<220> FEATURE:
<221> NAME/KEY: MOD_RES
<222> LOCATION: (4)..(4)
<223> OTHER INFORMATION: Azido-Phenylalanine

<400> SEQUENCE: 4

Phe Leu Leu Phe
1

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-aminomethylene-L-phenylalanine modified with
      epoxyketone warhead.
<220> FEATURE:
<221> NAME/KEY: MOD_RES
<222> LOCATION: (4)..(4)
<223> OTHER INFORMATION: Azido-Phenylalanine

<400> SEQUENCE: 5

Phe Leu Leu Phe
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-aminomethylene-L-phenylalanine modified with
      vinyl sulfone warhead.
<220> FEATURE:
<221> NAME/KEY: MOD_RES
<222> LOCATION: (3)..(3)
<223> OTHER INFORMATION: 4-aminomethylene-L-phenylalanine
<220> FEATURE:
<221> NAME/KEY: MOD_RES
<222> LOCATION: (4)..(4)
<223> OTHER INFORMATION: Azido-Phenylalanine

<400> SEQUENCE: 6

Phe Leu Phe Phe
1

<210> SEQ ID NO 7
<211> LENGTH: 4
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-aminomethylene-L-phenylalanine modified with
      vinyl sulfone warhead.
<220> FEATURE:
<221> NAME/KEY: MOD_RES
<222> LOCATION: (4)..(4)
<223> OTHER INFORMATION: Modified with BODIPY-triazole.

<400> SEQUENCE: 7

Phe Leu Leu Phe
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Succinyl-Leucine
<220> FEATURE:
<221> NAME/KEY: MOD_RES
<222> LOCATION: (4)..(4)
<223> OTHER INFORMATION: Modified with amino-4-methylcoumarin.

<400> SEQUENCE: 8

Leu Leu Val Tyr
1

<210> SEQ ID NO 9
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION, Nle
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Modified with amino-4-methylcoumarin.

<400> SEQUENCE: 9

Leu Pro Leu Asp
1

<210> SEQ ID NO 10
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with 7-Methoxycoumarin.
<220> FEATURE:
<221> NAME/KEY: MOD_RES
<222> LOCATION: (10)..(10)
<223> OTHER INFORMATION: Dinitrophenyl-Lysine
<220> FEATURE:
<221> NAME/KEY: MOD_RES
```

```
<222> LOCATION: (11)..(11)
<223> OTHER INFORMATION: D-Arg

<400> SEQUENCE: 10

Gly Lys Pro Ile Leu Phe Phe Arg Leu Lys Xaa
1               5                   10

<210> SEQ ID NO 11
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Modified with Rhodamine110.

<400> SEQUENCE: 11

Asp Glu Val Asp
1

<210> SEQ ID NO 12
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-amino-L-phenylalanine modified with vinyl
      sulfone warhead.
<220> FEATURE:
<221> NAME/KEY: MOD_RES
<222> LOCATION: (4)..(4)
<223> OTHER INFORMATION: Azido-Phenylalanine

<400> SEQUENCE: 12

Phe Leu Leu Phe
1

<210> SEQ ID NO 13
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-Amino-L-Phenylalanine modified with
      epoxyketone warhead.
<220> FEATURE:
<221> NAME/KEY: MOD_RES
<222> LOCATION: (4)..(4)
<223> OTHER INFORMATION: Azido-Phenylalanine

<400> SEQUENCE: 13

Phe Leu Leu Phe
1

<210> SEQ ID NO 14
<211> LENGTH: 4
<212> TYPE: PRT
<213> ORGANISM: Artificial sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: Ala(4-pyridine) modified with vinyl sulfone
      warhead.
<220> FEATURE:
<221> NAME/KEY: MOD_RES
<222> LOCATION: (4)..(4)
<223> OTHER INFORMATION: Azido-Phenylalanine.

<400> SEQUENCE: 14

Ala Leu Leu Phe
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with vinyl sulfone warhead.
<220> FEATURE:
<221> NAME/KEY: MOD_RES
<222> LOCATION: (4)..(4)
<223> OTHER INFORMATION: Azido-Phenylalanine.

<400> SEQUENCE: 15

Lys Leu Leu Phe
1

<210> SEQ ID NO 16
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-Aminomethylene-L-phenylalanine modified wiht
      vinyl sulfone warhead.
<220> FEATURE:
<221> NAME/KEY: MOD_RES
<222> LOCATION: (3)..(3)
<223> OTHER INFORMATION: Ala(4-pyridine).
<220> FEATURE:
<221> NAME/KEY: MOD_RES
<222> LOCATION: (4)..(4)
<223> OTHER INFORMATION: Azido-Phenylalanine.

<400> SEQUENCE: 16

Phe Leu Ala Phe
1

<210> SEQ ID NO 17
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-Aminomethylene-L-phenylalanine modified with
      vinyl sulfone warhead.
<220> FEATURE:
<221> NAME/KEY: MOD_RES
<222> LOCATION: (3)..(3)
<223> OTHER INFORMATION: 4-Amino-L-phenylalanine.
<220> FEATURE:
<221> NAME/KEY: MOD_RES
```

```
<222> LOCATION: (4)..(4)
<223> OTHER INFORMATION: Azido-Phenylalanine.

<400> SEQUENCE: 17

Phe Leu Phe Phe
1

<210> SEQ ID NO 18
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-Aminomethylene-L-phenylalanine modified with
      vinyl sulfone warhead.
<220> FEATURE:
<221> NAME/KEY: MOD_RES
<222> LOCATION: (3)..(3)
<223> OTHER INFORMATION: 4-Aminomethylene-L-phenylalanine.
<220> FEATURE:
<221> NAME/KEY: MOD_RES
<222> LOCATION: (4)..(4)
<223> OTHER INFORMATION: Azido-Phenylalanine.

<400> SEQUENCE: 18

Phe Leu Phe Phe
1

<210> SEQ ID NO 19
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-amino-L-phenylalanine modified with vinyl
      sulfone warhead.
<220> FEATURE:
<221> NAME/KEY: MOD_RES
<222> LOCATION: (3)..(3)
<223> OTHER INFORMATION: 4-Aminomethylene-L-phenylalanine.
<220> FEATURE:
<221> NAME/KEY: MOD_RES
<222> LOCATION: (4)..(4)
<223> OTHER INFORMATION: Azido-Phenylalanine.

<400> SEQUENCE: 19

Phe Leu Phe Phe
1

<210> SEQ ID NO 20
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Ala(4-pyridine) modified with vinyl sulfone
      warhead.
<220> FEATURE:
<221> NAME/KEY: MOD_RES
<222> LOCATION: (3)..(3)
<223> OTHER INFORMATION: 4-Aminomethylene-L-phenylalanine.
<220> FEATURE:
<221> NAME/KEY: MOD_RES
<222> LOCATION: (4)..(4)
<223> OTHER INFORMATION: Azido-Phenylalanine.
```

<400> SEQUENCE: 20

Ala Leu Phe Phe
1

<210> SEQ ID NO 21
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with vinyl sulfone warhead.
<220> FEATURE:
<221> NAME/KEY: MOD_RES
<222> LOCATION: (3)..(3)
<223> OTHER INFORMATION: 4-Aminomethylene-L-phenylalanine.
<220> FEATURE:
<221> NAME/KEY: MOD_RES
<222> LOCATION: (4)..(4)
<223> OTHER INFORMATION: Azido-Phenylalanine.

<400> SEQUENCE: 21

Leu Leu Phe Phe
1

<210> SEQ ID NO 22
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with vinyl sulfone warhead.
<220> FEATURE:
<221> NAME/KEY: MOD_RES
<222> LOCATION: (3)..(3)
<223> OTHER INFORMATION: 4-Amino-L-phenylalanine.
<220> FEATURE:
<221> NAME/KEY: MOD_RES
<222> LOCATION: (4)..(4)
<223> OTHER INFORMATION: Azido-Phenylalanine

<400> SEQUENCE: 22

Leu Leu Phe Phe
1

<210> SEQ ID NO 23
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with vinyl sulfone warhead.
<220> FEATURE:
<221> NAME/KEY: MOD_RES
<222> LOCATION: (3)..(3)
<223> OTHER INFORMATION: Ala(4-pyridine).
<220> FEATURE:
<221> NAME/KEY: MOD_RES
<222> LOCATION: (4)..(4)
<223> OTHER INFORMATION: Azido-Phenylalanine.

<400> SEQUENCE: 23

Leu Leu Ala Phe
1

```
<210> SEQ ID NO 24
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Modified with vinyl sulfone warhead.
<220> FEATURE:
<221> NAME/KEY: MOD_RES
<222> LOCATION: (4)..(4)
<223> OTHER INFORMATION: Azido-Phenylalanine.

<400> SEQUENCE: 24

Phe Leu Phe Phe
1

<210> SEQ ID NO 25
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: 4-Aminomethylene-L-phenylalanine modified with
      vinyl sulfone warhead.
<220> FEATURE:
<221> NAME/KEY: MOD_RES
<222> LOCATION: (3)..(3)
<223> OTHER INFORMATION: 4-Aminomethylene-L-phenylalanine.
<220> FEATURE:
<221> NAME/KEY: MOD_RES
<222> LOCATION: (4)..(4)
<223> OTHER INFORMATION: Modified with BODIPY-triazole.

<400> SEQUENCE: 25

Phe Leu Phe Phe
1
```

INHIBITORS OF THE TRYPSIN-LIKE SITE OF THE PROTEASOME AND METHODS OF USE THEREOF

This patent application is a continuation-in-part application of U.S. Ser. No. 13/399,189, filed Feb. 17, 2012, which claims the benefit of priority from U.S. Provisional Application Ser. No. 61/444,164 filed Feb. 18, 2011, the content of which is incorporated herein by reference in its entirety.

This invention was made with government support under contract number 5RO1CA124634-02 awarded by the National Cancer Institute. The government has certain rights in the invention.

BACKGROUND OF THE INVENTION

Proteasomes are proteolytic machines that are responsible for turnover of the majority of proteins in mammalian cells. The proteasome inhibitor bortezomib (VELCADE) is used for treatment of multiple myeloma, and at least five second-generation proteasome inhibitors including carfilzomib (PR-171) (Demo, et al. (2007) *Cancer Res.* 67:6383-91; O'Connor, et al. (2009) *Clin. Cancer Res.* 15:7085-91), NPI-0052 (Chauhan, et al. (2005) *Cancer Cell* 8:407-19), CEP-18770 (Piva, et al. (2008) *Blood* 111:2765-75), MLN-9708 (Kupperman, et al. (2010) *Cancer Res.* 70:1970-80), and ONX-0912 (PR-047)(Zhou, et al. (2009) *J. Med. Chem.* 52:3028-38) are in clinical testing.

Proteasomes have three different types of active sites, chymotrypsin-like (β5), trypsin-like (β2), and caspase-like (β1). Cells of the immune system express γ-interferon inducible immunoproteasomes, which have slightly different catalytic subunits, namely the β5i (LMP7), β2i (MECL1), and β1i (LMP2). Of these, the chymotrypsin-like sites (β5 and β5i) have long been considered as the only suitable targets for drug development. Bortezomib and all drugs presently undergoing trials were developed to target these sites (Adams (2004) *Cancer Cell* 5:417-21). However, bortezomib, CEP-18770, and MLN-9708 co-target the caspase-like sites (Piva, et al. (2008) supra; Kupperman, et al. (2010) supra; Kisselev, et al. (2006) *J. Biol. Chem.* 281:8583-8590; Altun, et al. (2005) *Cancer Res.* 65:7896-901; Berkers, et al. (2005) *Nat. Methods* 2:357-62), whereas NPI-0052 co-targets trypsin-like and caspase-like sites (Chauhan, et al. (2005) supra). This raises the question of whether inhibition of these sites is important for the anti-neoplastic activity of these drugs. It has been demonstrated that, in most multiple myeloma cell lines, cytotoxicity of inhibitors does not correlate with inhibition of the chymotrypsin-like sites but does correlate with loss of specificity and onset of inhibition of the trypsin-like sites (Britton, et al. (2009) *Chem. Biol.* 16:1278-89). These data strongly suggest that the trypsin-like sites are important co-targets for anti-neoplastic agents (Britton, et al. (2009) supra). Cell-permeable inhibitors of these sites are needed to test this hypothesis.

Conventional efforts to develop specific inhibitors of the trypsin-like site have met with limited success to date. Most proteasome inhibitors are short N-terminally capped peptides with an electrophilic group at the C-terminus. This electrophile interacts, reversibly or irreversibly, with the catalytic N-terminal threonine of the proteasome active site. The peptide moiety of the inhibitor binds to the substrate binding pocket of the active site and is largely responsible for the specificity (Kisselev & Goldberg (2001) *Chem. Biol.* 8:739-758; Groll & Huber (2004) *Biochim. Biophys. Acta* 1695:33-44), although the specificity may be influenced by an electrophile (Screen, et al. (2010) *J. Biol. Chem.* 285:40125-40134).

The trypsin-like sites cleave peptide bonds after a basic residue and it has been shown that the P3 substituent (Arg) of the β2 selective inhibitor Ac-Tyr-Arg-Leu-Asn-VS (1, SEQ ID NO:1) is of importance in selectivity enhancement (Harris, et al. (2001) *Chem. Biol.* 8:1131-41; Nazif & Bogyo (2001) *Proc. Natl. Acad. Sci. USA* 98:2967-2972; Groll, et al. (2002) *Chem. Biol.* 9:655-62). However, inclusion of basic residues in the P1 and P3 positions are challenging to synthesize and would be expected to render the inhibitor cell-impermeable. In this respect, the few β2-specific aldehydes (Loidl, et al. (1999) *Chem. Biol.* 6:197-204) and vinyl sulfones (Nazif & Bogyo (2001) supra; Groll, et al. (2002) supra) are not cell-permeable. A cell-permeable peptide vinyl ester (ve), HMB-VSL-VE 2, has been suggested to be a specific inhibitor of the trypsin-like sites (Marastoni, et al. (2005) *J. Med. Chem.* 48:5038-42; Baldisserotto, et al. (2007) *Eur. J. Med. Chem.* 42:586-592), but does not show inhibitory activity in conventional assays (Screen, et al. (2010) supra).

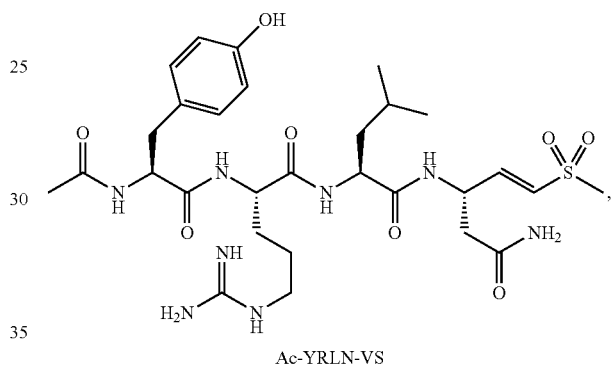

Ac-YRLN-VS

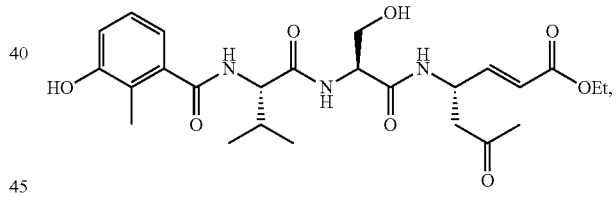

HMB-VSL-VE

SUMMARY OF THE INVENTION

The present invention a peptide-based inhibitor of the proteasome β2/β2i site having the structure:

(Y)-(X4)-X3-X2-X1 (SEQ ID NO:2), wherein X1 is an Arg residue or an aminosubstituted phenylalanine derivative, wherein said residue or derivative has an epoxyketone or vinyl sulfone warhead; X2 is Leu or Ser; X3 is Leu, Val, Ser, Arg, His, Lys, Phe or an aminosubstituted phenylalanine derivative; X4 is present or absent and when present is Phe; and Y is present or absent and when present is a capping group.

A pharmaceutical composition containing the peptide-based inhibitor of the invention and a pharmaceutically acceptable carrier is also provided, wherein some embodiments, embrace the inclusion of an inhibitor of the proteasome β5/β5i site.

Methods for inhibiting the activity of the β2/β2i site of a proteasome and treating cancer, allograft rejection, autoimmune disease, parasitic infection or inflammatory condition using the peptide-based inhibitor of the invention are also provided as is a method for producing a peptide-based inhibitor.

BRIEF DESCRIPTION OF THE DRAWINGS 3

DETAILED DESCRIPTION OF THE INVENTION

Figure 1A:
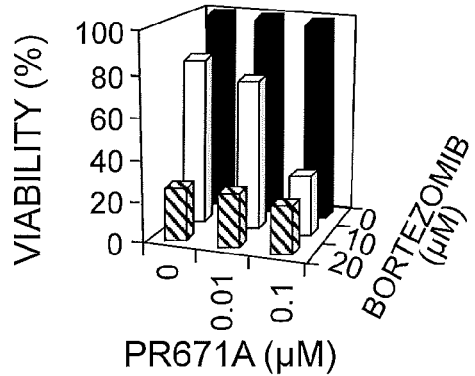
FIG. 1 shows that the combination of compound 4a (PR671A) with β5-selective proteasome inhibitors, bortezomib (FIGS. 1A and 1D) or PR523 (i.e., LU-005.
FIGS. 1B and 1D) results in synergistic cytoxicity against myeloma cells, U266 (FIGS. 1A and 1B) and AMO-1 (FIGS. 1C and 1D) cells.
Figure 1C:
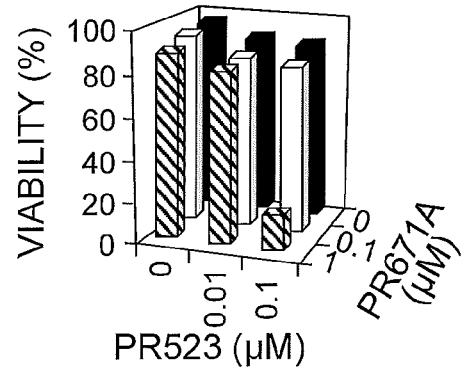
Figure 1B:
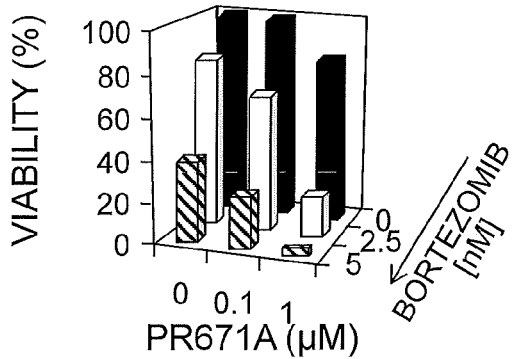
Figure 1D:
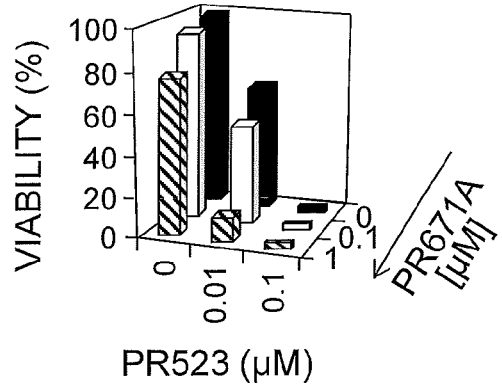

Proteasomes degrade the majority of proteins in mammalian cells, are involved in the regulation of multiple physiological functions, and are established targets of anti-cancer drugs. The mammalian 20S proteasome catalytic core contains two sets of three catalytically active β subunits, which display a different substrate specificity, namely β1 (caspase-like) cleaves after acidic residues, β2 (trypsin-like) cleaves after basic residues and β5 (chymotrypsin-like) cleaves after bulky, hydrophobic residues. In specific cell types involved in the immune surveillance system, the β1i, β2i and β5i active subunits replace their corresponding constitutive counterparts and, β5 is replaced by β5i in cortical thymic epithelial cells.

Chymotrypsin-like sites are the most important for protein breakdown and have been the primary target for anti-neoplastic drug development; however, inhibitors of caspase-like sites have also been shown to sensitize malignant cells to inhibitors of the chymotrypsin-like sites. In the instant invention, specific cell-permeable inhibitors and activity-based probes of the third site type, the trypsin-like sites, have now been developed. These compounds are peptide-based epoxyketones or vinyl sulfones (VS) that contain arginine or an aminosubstituted phenylalanine derivative in the P1 position and inhibit trypsin-like β2/β2i sites of 26S proteasomes. The compounds of the invention also selectively sensitize multiple myeloma cells to inhibitors of the chymotrypsin-like sites, including the anti-myeloma agents bortezomib and carfilzomib. Sensitization was observed in cultured cells adapted to grow in the presence of bortezomib and bortezomib-resistant multiple myeloma cells isolated from patients with bortezomib-refractory myeloma. Thus, the compounds of the invention, when used in combination with inhibitors to the chymotryptic/caspase proteasome activity, overcome resistance of myeloma cells against these inhibitors. Thus, trypsin-like sites are co-targets (with chymotrypsin-like sites) for anti-cancers drugs and the compounds of this invention can be used in the treatment of cancer and sensitization of malignant cells to therapeutic proteasome inhibitors that target β5/β5i sites of the proteasome. Using the specific cell-permeable inhibitors and activity-based probes of this invention, the proteasome's active sites can be modulated separately in living cells.

Accordingly, the present invention features inhibitors of the trypsin-like β2/β2i sites of 26S proteasomes, which are characterized as being peptide-based epoxyketones or vinyl sulfones that contain an arginine or an aminosubstituted phenylalanine derivative at the C-terminus (i.e., at the P1 position). Inhibitors of the present invention are "peptide-based" in the sense that they contain between 1 and 5 amino acid residues covalently attached by peptide bonds. In some embodiments, the inhibitors of the invention are oligopeptides containing between 2 and 5 amino acid residues. In other embodiments, the inhibitors of the invention are oligopeptides containing between 3 and 5 amino acid residues. In particular embodiments, the inhibitors of the invention are oligopeptides containing between 2 and 4 or 3 and 4 amino acid residues.

For the purposes of the present invention, an amino acid residue can be a natural amino acid residue or non-natural amino acid residue. Thus, the inhibitors of the invention can contain between 1 and 5 amino acid residues, wherein 1 to 5 of the amino acid residues are natural or non-natural amino acid residues.

The inhibitors of the invention have the general structure of:

(Y)-(X4)-X3-X2-X1 (SEQ ID NO:2), wherein X1 is an Arg residue or an aminosubstituted phenylalanine derivative, wherein said residue or derivative has an epoxyketone (ek) or vinyl sulfone (VS) warhead; X2 is Leu or Ser; X3 is Leu, Val, Ser, Arg, His, Lys, Phe or an aminosubstituted phenylalanine derivative; X4 is present or absent and when present is Phe; and Y is present or absent and when present is a capping group As used herein, an aminosubstituted phenylalanine derivative of the invention has the structure:

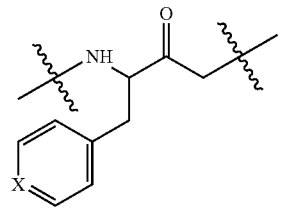

wherein X is N, C—NH$_2$, or C—CH$_2$—NH$_2$.

A capping group of the present invention is a group routinely used in the art to cap or protect alpha amino groups. Capping groups of use in the instant invention include, but not limited to, a HMB (N-(3-hydroxy-2-methylbenzoyl)) group, an acetyl (Ac) group, a carboxybenzyl (Z) group, a benzoyl (Bz) group, or an azido group, See Kristjansson (2001) Curr. Protoc. Food Anal. Chem. C2.1.1-C2.1.7.

Detectable labels or dyes can also serve as capping groups of the instant peptides. Labels or dyes are detectable in the sense that they can be directly or indirectly measured by fluorometry, spectrometry or the like. Examples of amine-reactive dyes or labels which can serve as capping groups of the instant invention include, but are not limited to, a 4,4-difluoro-4-bora-3a,4a-diaza-s-indacene (BODIPY) fluorophore (e.g., BODIPY FL, BODIPY 493/503, BODIPY 530/550, BODIPY TMR, BODIPY 558/568, BODIPY 576/589, BODIPY 581/591, BODIPY TR, BODIPY 630/650, or BODIPY 650/665), an ALEXA Fluor (e.g., ALEXA Fluor 405, ALEXA Fluor 532, ALEXA Fluor 555, ALEXA Fluor 546, ALEXA Fluor 488 or ALEXA Fluor 750), a fluoroscein (e.g., 2',7'-dichloro-fluoroscein, 4',5'-dichloro-2'7'-dimethoxyfluoroscein, or naphthofluorescein), a rhodamine dye (e.g., rhodamine red, X-rhodamineor a Texas Red dye), biotin and the like.

Exemplary peptide-based inhibitors of the invention include the molecules listed in Table 1.

TABLE 1
| Compound | SEQ ID NO: |
|---|---|
| 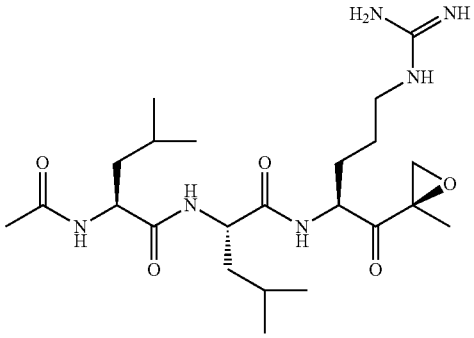 NC-002 (Ac-Leu-Leu-Arg-ek) | |
| 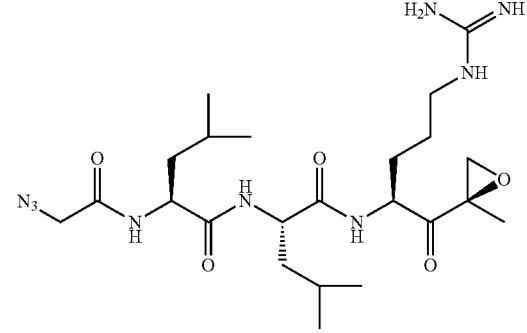 Az-NC-002 (AzGly-Leu-Leu-Arg-ek) | 3 |
| 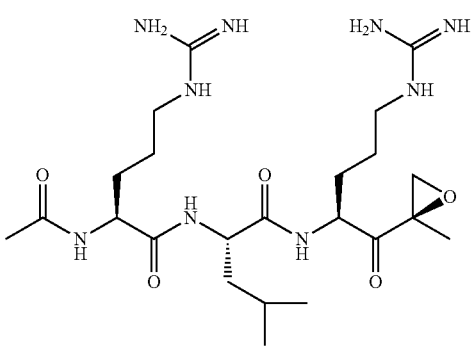 NC-012 (Ac-Arg-Leu-Arg-ek) | |
| 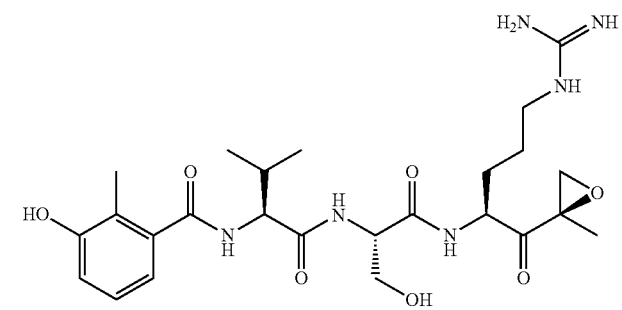 NC-022 (HMB-Val-Ser-Arg-ek) | |

TABLE 1-continued
| Compound | SEQ ID NO: |
|---|---|
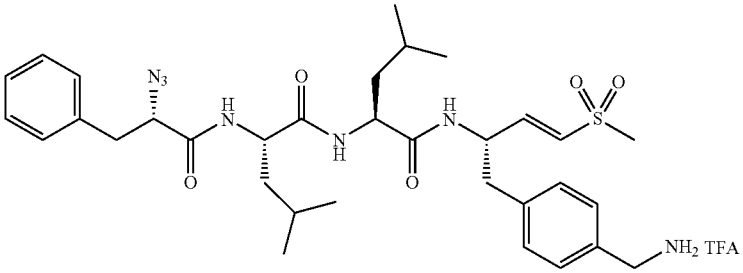
4a (PR671A)
($N_3$Phe-Leu-Leu-Phe(4-$CH_2NH_2$)VS)
4
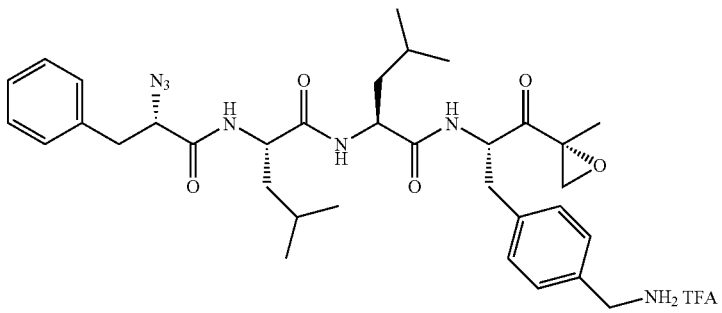
4b
($N_3$Phe-Leu-Leu-Phe(4-$CH_2NH_2$)ek)
5
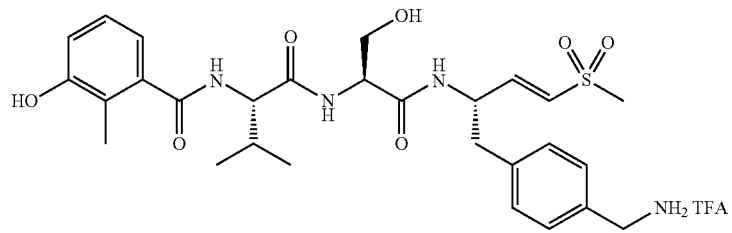
40
((Val-Ser-Phe(4-$CH_2NH_2$)-methyl vinyl sulfone)-3-hydroxy-2-methylbenzamide)
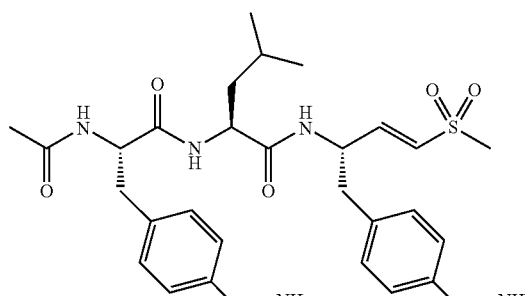
42
(Ac-Phe(4-$CH_2NH_2$)-Leu-Phe(4-$CH_2NH_2$)VS)

TABLE 1-continued

| Compound | SEQ ID NO: |
|---|---|
| 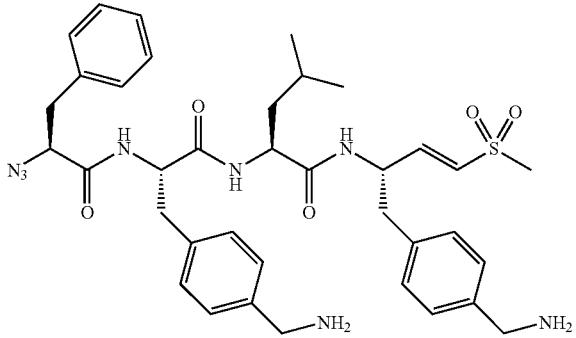<br>43<br>(N₃Phe-Phe(4-CH₂NH₂)-Leu-Phe(4-CH₂NH₂)VS) | 6 |
| 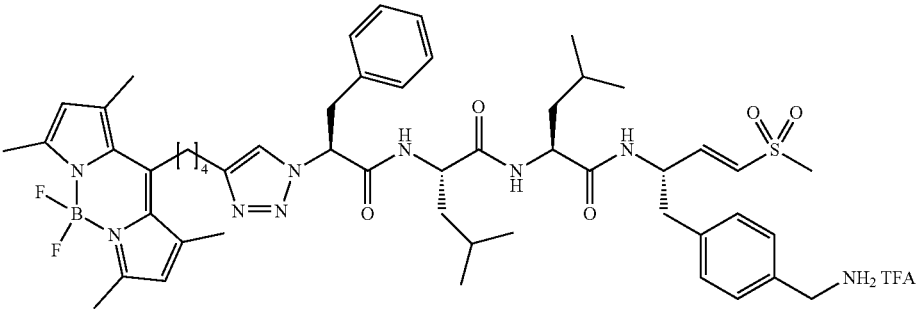<br>39<br>(BODIPY-triazole-Phe-Leu-Leu-Phe(4-CH₂NH₂)VS) | 7 |

Peptide-based inhibitors can be produced by the exemplary methods disclosed herein (see, e.g., the Schemes and the Examples), which, in general, involve the steps of (a) protecting amine groups of arginine or an aminosubstituted phenylalanine derivative, (b) introducing an epoxyketone or vinyl sulfone warhead onto the arginine or aminosubstituted phenylalanine derivative, and (c) attaching a proteasomal β2/β2i site-selective oligopeptide to the alpha amino-group of the arginine or aminosubstituted phenylalanine derivative. As described herein, the P2, P3, and optional P4 amino acid residues of the peptide-based inhibitor are amino acid residues that enhance selectivity for the β2/β2i site of the proteasome. In this respect, "a proteasomal β2/β2i site-selective oligopeptide" is a peptide containing the P2, P3, and optional P4 amino acid residues as described herein.

Inhibitor compositions of this invention can be administered in various forms, depending on the disorder to be treated and the age, condition, and body weight of the subject, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional pharmaceutical carrier, additive or excipient, such as a binder, a disintegrating agent, a lubricant, a corrigent, a solubilizing agent, a suspension aid, an emulsifying agent, or a coating agent in addition to a cyclodextrin and a buffer. Although the dosage will vary depending on the symptoms, age and body weight of the patient, the nature and severity of the disorder to be treated or prevented, the route of administration and the form of the inhibitor, in general, a daily dosage of from 0.01 to 2000 mg of the inhibitor is recommended for an adult human patient, and this may be administered in a single dose or in divided doses. The amount of active ingredient which can be combined with a carrier material to produce a single dosage form will generally be that amount of the inhibitor which produces a therapeutic effect.

The precise time of administration and/or amount of a composition that will yield the most effective results in terms of efficacy of treatment in a given patient will depend upon the activity, pharmacokinetics, and bioavailability of a particular inhibitor, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is used herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

It is further contemplated that the instant inhibitors can be prepared as pharmaceutically acceptable salt. The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge, et al. (1977) *J. Pharm. Sci.* 66:1-19.)

In other cases, the inhibitors of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge, et al. (1977) supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions. Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent. Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound. Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (TWEENS, PLURONICS, sorbitan esters, lecithin, CREMOPHORS), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration can include one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle. Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

The preparations of inhibitors may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion. The phrases "systemic administration," "administered systemically," "peripheral administration" and "administered peripherally" as used herein mean the administration of an inhibitor, or other material other than directly into the central nervous system, such that it enters the subject's system and thus, is subject to metabolism and other like processes, for example, subcutaneous administration.

The inhibitors of the invention may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient. The concentration of a disclosed inhibitor in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected inhibitor(s).

In one embodiment, the proteasome inhibitor is provided as a conjoint therapy, wherein one or more other therapeutic agents are administered with the proteasome inhibitor composition. Such conjoint treatment may be achieved by way of the simultaneous, sequential, or separate dosing of the individual components of the treatment.

In certain embodiments, a composition of the invention is conjointly administered with a chemotherapeutic. Suitable chemotherapeutics may include, natural products such as vinca alkaloids (i.e., vinblastine, vincristine, and vinorelbine), paclitaxel, epipodophyllotoxins (i.e., etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents; antiproliferative/antimitotic alkylating agents such as nitrogen mustards (mechlorethamine, cyclophosphamide and analogs, melphalan, chlorambucil), ethylenimines and methylmelamines (hexaamethylmelaamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; histone deacetylase (HDAC) inhibitors (trichostatin, sodium butyrate, apicidan, suberoyl anilide hydroamic acid); HSP90 inhibitors (i.e., tanespimycin, retaspimycin, AUY922) hormones (i.e., estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In other embodiments, a composition of the invention is conjointly administered with a cytokine. Cytokines include, but are not limited to, Interferon-γ, -α, and β, Interleukins 1-8, 10 and 12, Granulocyte Monocyte Colony-Stimulating factor (GM-CSF), TNF-α and -β, and TGF-β.

In still other embodiments, a composition of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a composition of the invention is conjointly administered with an immunotherapeutic agent. Suitable immunotherapeutic agents may include, but are not limited to, MDR modulators (verapamil, valspordar, biricodar, tariquidar, laniquidar), cyclosporine, thalidomide, lenalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

In particular embodiments, a composition of the invention is conjointly administered with one or more other proteasome inhibitor(s), in particular inhibitors of the chymotrypsin-like sites. Such inhibitors include, e.g., bortezomib (VELCADE), carfilzomib (PR-171), marizomib (NPI-0052), CEP-18770, MLN-9708, and ONX-0912 (PR-047).

Having demonstrated the selective activity of the instant inhibitors, the present invention features a method for inhibiting the β2/β2i activity of proteasome by contacting a proteasome (either in vivo or in vitro) with a composition described herein. Activity of an inhibitor can be demonstrated using the exemplified cell-free or cell-based assays or any other suitable assay routinely used in the art to assess proteasome activity.

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations containing one or more of the proteasome β2/β2i-selective inhibitors described hereinare of use in the treatment of these proteasome-mediated diseases or conditions. For the purposes of the present invention, a proteasome-mediated disease or condition is a disease or condition in which the activity or overactivity of the proteasome has been directly or indirectly associated with the development or persistence of the disease or condition. In this respect, inhibition of proteasome activity will have a beneficial effect of ameliorating, preventing or treating the disease or condition. In particular embodiments, the proteasome-mediated disease or condition is cancer, allograft rejection, autoimmune disease, parasitic infection or an inflammatory condition.

At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy (Glotzer, et al. (1991) Nature 349:132-138). The fact that epoxomicin was initially identified in a screen for antitumor compounds validates the proteasome as an antitumor chemotherapeutic target. Accordingly, the compositions of the invention are useful for treating cancer.

Proteasome inhibition has also been associated with inhibition of NF-κB activation and stabilization of p53 levels. Thus, compositions of the invention may also be used to inhibit NF-κB activation, and stabilize p53 levels in cell culture. Since NF-κB is a key regulator of inflammation, it is an attractive target for anti-inflammatory therapeutic intervention. Thus, compositions of the invention are of use in the treatment of conditions associated with inflammation, including, but not limited to COPD, psoriasis, bronchitis, emphysema, and cystic fibrosis.

The disclosed compositions can also be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include regulatory proteins such as cyclins and transcription factor NF-κB.

In some embodiment, the invention relates to the treatment of cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver.

Inhibitors of the invention are useful for treating conditions such as chronic infectious diseases, fever, muscle disuse (atrophy) and denervation, nerve injury, fasting, renal failure associated with acidosis, and hepatic failure. See, e.g., U.S. Pat. No. 5,340,736. Embodiments of the invention therefore encompass methods for reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of a pharmaceutical composition disclosed herein.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κB2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB, which translocates from the cytoplasm to the nucleus. Ubiquitinated p105 is also processed by purified proteasomes (Palombella, et al. (1994) Cell 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain K gene, the IL-2 receptor α-chain gene, the class I major histocompatibility complex gene, and a number of cytokine genes encoding, for example, IL-2, IL-6, granulocyte colony-stimulating factor, and IFN-β. (Palombella, et al. (1994) Cell 78:773-785). Thus, some embodiments of the invention include methods of affecting the level of expression of IL-2, MHC-I, IL-6, TNF-α, IFN-β, or any of the other previously-mentioned proteins, each method including administering to a subject an effective amount of a composition disclosed herein.

NF-κB also participates in the expression of the cell adhesion genes that encode E-selectin, P-selectin, ICAM, and VCAM-1 (Collins (1993) Lab. Invest. 68:499-508). Thus, one embodiment of the invention is a method for inhibiting cell adhesion (e.g., cell adhesion mediated by E-selectin, P-selectin, ICAM, or VCAM-1), including contacting a cell with (or administering to a subject) an effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB. It has been demonstrated that the severity of injury resulting in hypoxia can be reduced with the administration of a proteasome inhibitor (Pye, et al. (2003) Am. J. Physiol. 284:H919-H926). Therefore, certain embodiments of the invention relate to a method of treating an ischemic condition or reperfusion injury by administering to a subject in need of such treatment an effective amount of a compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

Overproduction of lipopolysaccharide (LPS)-induced cytokines such as TNF-α is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, indicating that the LPS-induced signal transduction may be an important therapeutic target in the treatment or prevention of sepsis (Qureshi, et al. (2003) *J. Immun.* 171:1515-1525). Therefore, in certain embodiments, compositions of the invention may be used for the inhibition of TNF-α to prevent and/or treat septic shock.

Many autoimmune diseases (e.g., lupus, myasthenia gravis) are mediated by the antibodies against selfproduced by plasma cells. Just like malignant myeloma cells, plasma cells are very sensitive to proteasome inhibitors. Proteasome inhibitors deplete plasma cells in mouse models of these diseases (Neubert, et al. (2008) *Nat. Med.* 14:748-755). Accordingly, in one embodiment, the invention provides a method to treat an autoimmune disease by inducing selective apoptosis of autoantibody-producing plasma cells.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. A further embodiment is a method for suppressing the immune system of a subject (e.g., inhibiting transplant rejection, allergy, asthma), including administering to the subject an effective amount of a composition described herein. Compositions of the invention can also be used to treat autoimmune diseases such as lupus, rheumatoid arthritis, multiple sclerosis, and inflammatory bowel diseases such as ulcerative colitis and Crohn's disease.

Another further embodiment is a method for altering the repertoire of antigenic peptides produced by the proteasome or other N-terminal nucleophile (Ntn) with multicatalytic activity. For example, if the caspase-like (PGPH) activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of trypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. (1994) *Cell* 78:773-785; Traenckner, et al. (1994) *EMBO J.* 13:5433-5441). Thus, one embodiment of the invention is a method for inhibiting IκB-α degradation, including contacting the cell with a composition described herein. A further embodiment is a method for reducing the cellular content of NF-κB in a cell, muscle, organ, or subject, including contacting the cell, muscle, organ, or subject with a composition described herein.

Other embodiments of the invention are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with $\beta 34^{cdc2}$ protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover (1994) *Cell* 79:13-21). Inhibition of the proteasome inhibits cyclin degradation, and therefore inhibits cell proliferation, for example, in cyclin-related cancers (Kumatori, et al. (1990) *Proc. Natl. Acad. Sci. USA* 87:7071-7075). Thus, another embodiment of the invention is a method for treating a proliferative disease in a subject (e.g., cancer, psoriasis, or restenosis), including administering to the subject an effective amount of a composition disclosed herein. The invention also encompasses a method for treating cyclin-related inflammation in a subject, including adminstering to a subject a therapeutically effective amount of a composition described herein.

Additional embodiments are methods for affecting the proteasome-dependent regulation of oncoproteins and methods of treating or inhibiting cancer growth, each method including exposing a cell (in vivo, e.g., in a subject, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a composition disclosed herein.

In another embodiment, the disclosed compositions are useful for the treatment of a parasitic infection, such as infections caused by protozoan parasites. The proteasome of these parasites is considered to be involved primarily in cell differentiation and replication activities (Paugam, et al. (2003) *Trends Parasitol.* 19(2):55-59). Furthermore, *entamoeba* species have been shown to lose encystation capacity when exposed to proteasome inhibitors (Gonzales, et al. (1997) *Arch. Med. Res.* 28, Spec No: 139-140). In certain embodiments, the disclosed compositions are useful for the treatment of parasitic infections in humans caused by a protozoan parasite selected from *Plasmodium* sps. (including *P. falciparum, P. vivax, P. malariae,* and *P. ovale,* which cause malaria), *Trypanosoma* sps. (including *T. cruzi,* which causes Chagas' disease, and *T. brucei* which causes African sleeping sickness), *Leishmania* sps. (including *L. amazonesis, L. donovani, L. infantum, L. mexicana,* etc.), *Pneumocystis carinii* (a protozoan known to cause pneumonia in AIDS and other immunosuppressed patients), *Toxoplasma gondii, Entamoeba histolytica, Entamoeba invadens,* and *Giardia lamblia.* In certain embodiments, the disclosed compositions are useful for the treatment of parasitic infections in animals and livestock caused by a protozoan parasite selected from *Plasmodiumhermani, Cryptosporidium* spp., *Echinococcusgranulosus, Eimeria tenella,* and *Sarcocystis neurona.* Other proteasome inhibitors for co-treatment of parasitic diseases with the inhibitors herein are described in WO 98/10779.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

Furthermore, the disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the β2/β2i subunit and inhibiting the proteolytic activities associated therewith. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

The invention is described in greater detail by the following non-limiting examples.

Example 1

Synthesis of Inhibitors

The synthesis of Boc-Arg(Pbf)-ek is shown in Scheme 1 (Pbf, 2,2,4,6,7-pentamethyldihydrobenzofuran-5-sulfonyl; boc, tert-butoxycarbonyl).

SCHEME 1

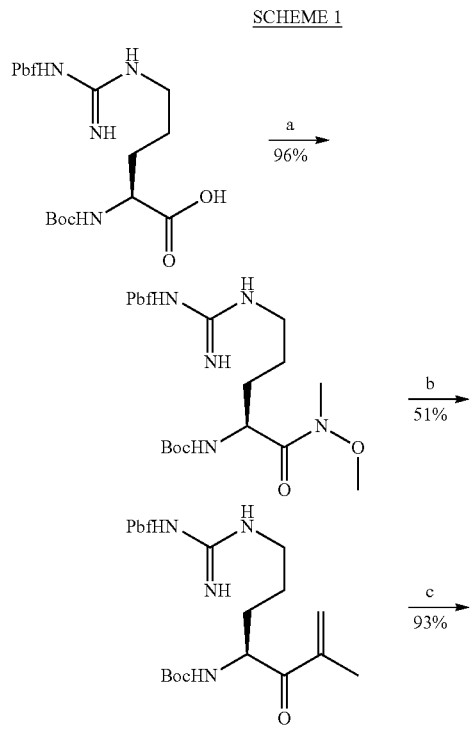

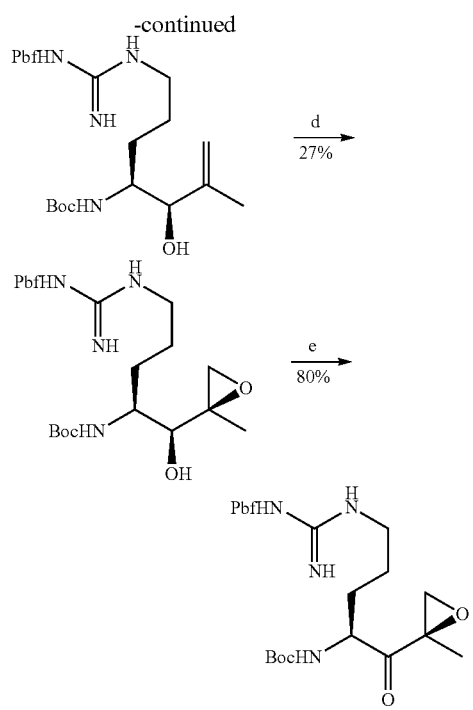

Reagents and Conditions of Scheme 1:
(a) CH₃NH(OCH₃)—HCl, HBTU (O-(benzotriazol-1-yl)-N,N,N',N'-tetramethyluronium hexafluorophosphate), DIPEA (diisopropyethylamine), CH₂Cl₂, room temperature; (b) 2-Bromopropene/t-BuLi, THF, −78° C.; (c) NaBH₄, CeCl₃·7H₂O, methanol, 0° C.; (d) t-BuOOH, VO(acac)₂, CH₂Cl₂, 0° C. to room temperature (acac, acetyacetonate); (e) Dess-Martin periodinane, DMSO, 0° C. to room temperature.

Boc-Arg(Pbf)-N(OCH3)CH₃.

Diisopropylethylamine (5.3 mL, 30.4 mmol) was added to a suspension of Boc-Arg(Pbf)-OH (2 g, 3.8 mmol), N,O-dimethylhydroxylamine hydrochloride (2.23 g, 22.8 mmol) and HBTU (1.58 g, 4.18 mmol) in dichloromethane (10 mL). The resulting solution was stirred at room temperature overnight, diluted with dichloromethane, washed successively with 1N HCl, aq. NaHCO₃, brine, dried over Na₂SO₄ and concentrated. The crude product was purified by column chromatography (EtOAc, SiO₂) to yield 2.07 g (96%) of Boc-Arg(Pbf)-NMe(OMe). ¹H NMR (CDCl₃) δ 1.42 (s, 9H), 1.46 (s, 6H), 1.54-1.76 (m, 4H), 2.09 (s, 3H), 2.53 (s, 3H), 2.59 (s, 3H), 2.96 (s, 2H), 3.10-3.20 (m, 1H), 3.20 (s, 3H), 3.32-3.44 (m, 1H), 3.74 (s, 3H), 4.60-4.70 (m, 1H), 5.49 (br d, 1H, J=8.7 Hz), 6.12 (br s, 2H), 6.32 (br s, 1H). ¹³C NMR (CDCl₃) δ 12.6, 12.7, 14.4, 19.3, 19.6, 25.2, 28.3, 28.4, 28.6, 28.7, 28.9, 41.0, 43:4, 60.6, 80.2, 86.5, 117.6, 124.7, 132.4, 133.2, 138.5, 156.3, 156.4, 158.8.

Boc-Arg(Pbf)-C(CH₃)=CH₂.

1.2M tert-Butyllithium solution in pentane (28.4 mL, 34.13 mmol) was added drop-wise to a solution of 2-bromopropene (1.52 mL, 17.5 mmol) in THF (35 mL) at −78° C. under inert atmosphere. Upon addition, the reaction mixture was stirred for an additional 30 minutes, then transferred drop-wise via canula into a stirred solution of Boc-Arg(Pbf)-NMe(OMe) (1 g, 1.75 mmol) in THF (35 mL) at −78° C. The resulting solution was stirred for another 3 hours at −78° C., after which saturated aq. NH₄Cl was added, the mixture was allowed to warm up to room temperature with stirring and extracted with EtOAc. The combined organic extracts were washed with brine, dried over Na₂SO₄ and concentrated. Column chromatography (1:3 hexanes-EtOAc) afforded 0.49 g (51%) of the target ketone Boc-Arg(Pbf)-C(CH$_3$)=CH$_2$. $^1$H NMR (CDCl$_3$) δ 1.42 (s, 9H), 1.47 (s, 6H), 1.57-1.70 (m, 3H), 1.71-1.78 (m, 1H), 1.89 (s, 3H), 2.10 (s, 3H), 2.52 (s, 3H), 2.58 (s, 3H), 2.96 (s, 2H), 3.10-3.20 (m, 1H), 3.40-3.50 (m, 1H), 5.01 (br t, 1H, J=8.0 Hz), 5.55 (br d, 1H, J=8.0 Hz), 5.91 (s, 1H), 5.98 (s, 1H), 6.14 (br s, 2H), 6.33 (br s, 1H). $^{13}$C NMR (CDCl$_3$) δ 12.2, 13.9, 17.7, 19.1, 25.1, 31.1, 40.5, 43.0, 53.4, 79.6, 86.2, 117.2, 124.4, 126.4, 131.9, 132.8, 138.0, 141.8, 155.6, 156.2, 158.5, 200.4 (two signals missing due to overlap).

1-(2-Propenyl)-αN-Boc,ωN-Pbf-argininol.

Sodium borohydride (48 mg, 1.25 mmol) was added in portions to a stirred solution of Boc-Arg(Pbf)-C(CH$_3$)=CH$_2$ (0.49 g, 0.89 mmol) and cerium(III) chloride heptahydrate (0.5 g, 1.34 mmol) in methanol (10 mL) at 0° C. The reaction mixture was stirred for an additional 30 minutes at 0° C., quenched with several drops of acetic acid for 15 minutes and concentrated. The residue was partitioned between water and EtOAc, aq. layer extracted with additional portions of EtOAc. The combined organic extracts were washed with brine, dried over Na$_2$SO$_4$ and concentrated to afford 0.46 g (93%) of the target allylic alcohol. $^1$H NMR (CDCl$_3$) δ 1.42 (s, 9H), 1.45 (s, 6H), 1.45-1.66 (m, 4H), 1.70 (s, 3H), 2.09 (s, 3H), 2.51 (s, 3H), 2.57 (s, 3H), 2.95 (s, 2H), 3.00-3.16 (m, 1H), 3.26-3.40 (m, 1H), 3.65-3.80 (m, 1H), 4.08 (br s, 1H), 4.91-5.07 (m, 1H), 4.95 (s, 1H), 5.01 (s, 1H), 6.11 (br s, 2H), 6.26 (br s, 1H). $^{13}$C NMR (CDCl$_3$) δ 11.7, 12.3, 17.7, 18.8, 19.2, 25.7, 41.0, 43.1, 77.4, 79.3, 86.2, 112.0, 117.3, 124.5, 132.1, 132.7, 138.2, 144.5, 156.2, 158.6 (four signals missing due to overlap).

1-(2-Methyloxiranyl)-αN-Boc,ωN-Pbf-argininol.

Vanadyl acetylacetonate (20 mg, 0.075 mmol) was dissolved in a solution of 1-(2-propenyl)-αN-Boc,ωN-Pbf-argininol (0.46 g, 0.83 mmol) in dichloromethane (15 mL) at 0° C. 5M tert-Butyl hydroperoxide solution in decane (0.33 mL) was then added at 0° C., cooling was removed, the reaction mixture stirred at room temperature for 15 minutes and quenched with saturated aq. NaHCO$_3$. The aq. layer was further extracted with dichloromethane, the combined organic extracts were washed with brine, dried over Na$_2$SO$_4$ and concentrated. The residue was separated by column chromatography (1:4 hexanes-EtOAc to 100% EtOAc) to afford 53 mg (12%) of unreacted starting material and 0.13 g (27%) of the target epoxyalcohol. $^1$H NMR (CDCl$_3$) δ 1.31 (s, 3H), 1.40-1.50 (m, 3H), 1.41 (s, 9H), 1.46 (s, 6H), 1.56-1.64 (m, 1H), 2.08 (s, 3H), 2.49 (s, 3H), 2.56 (s, 3H), 2.59 (d, 1H, J=4.5 Hz), 2.88 (d, 1H, J=5.0 Hz), 2.95 (s, 2H), 3.10-3.20 (m, 1H), 3.20-3.30 (m, 1H), 3.65 (br m, 1H), 3.76 (br m, 1H), 5.25 (d, 1H, J=4.5 Hz), 6.26-6.35 (br m, 3H). $^{13}$C NMR (CDCl$_3$) δ 12.68, 18.11, 18.31, 19.36, 19.57, 28.32, 28.52, 28.71, 28.91, 43.46, 57.51, 60.62, 74.27, 80.24, 86.56, 117.67, 124.78, 132.52, 133.18, 138.59, 156.39, 156.78, 158.91 (one signal missing due to overlap.

Boc-Arg(Pbf)-ek.

Dess-Martin periodinane (0.23 g, 0.54 mmol) was added to a stirred half-frozen solution of 1-(2-methyloxiranyl)-αN-Boc,ωN-Pbf-argininol (0.13 g, 0.24 mmol) in DMSO (4 mL) at 0° C. The reaction mixture was allowed to warm up to room temperature and stirred overnight, then cooled and quenched with saturated aq. NaHCO$_3$. The resulting aq. solution was extracted with EtOAc, organic extracts were washed with brine, dried over Na$_2$SO$_4$ and concentrated. Column chromatography (EtOAc) afforded 0.11 g (80%) of the target epoxyketone. $^1$H NMR (CDCl$_3$) δ 1.40 (s, 9H), 1.46 (s, 6H), 1.50 (s, 3H), 1.54-1.68 (m, 3H), 1.72-1.82 (m, 1H), 2.10 (s, 3H), 2.52 (s, 3H), 2.58 (s, 3H), 2.89 (d, 1H, J=4.8 Hz), 2.96 (s, 2H), 3.14 (d, 1H, J=4.2 Hz), 3.15-3.25 (m, 1H), 3.30-3.40 (m, 1H), 4.25 (br t, 1H, J=8.4 Hz), 5.31 (d, 1H, J=8.7 Hz), 6.20-6.45 (br s, 3H). $^{13}$C NMR (CDCl$_3$) δ 12.4, 16.6, 17.9, 19.3, 25.5, 28.3, 28.6, 40.6, 43.2, 52.3, 58.9, 80.0, 86.3, 117.4, 124.5, 129.5, 132.2, 132.8, 138.3, 155.9, 156.2, 158.7, 213.4. HRMS (ESI, m/z): calculated for [M+H]$^+$ (C$_{27}$H$_{43}$N$_4$O$_7$S) 567.2847. found 567.2841.

General Procedure for the Synthesis of Active Peptides.

The left-hand dipeptides were synthesized by conventional techniques on solid phase. A mixture of Boc-Arg(Pbf)-ek (10 mg, 0.018 mmol) and toluene (ca. 2 mL) was concentrated in vacuo and the Boc group was removed by stirring the residue in 16% TFA (trifluoroacetic acid) in dichloromethane for 30 minutes at room temperature. The reaction mixture was concentrated in vacuo and dried by azeotropic evaporation of toluene. To the solid residue was added a solution of the appropriate left-hand dipeptide (1.1-2 equiv) and HBTU (1.3-2 equiv) in DMF (2 mL). Diisopropylethylamine (4-5 equiv) was then added, the reaction mixture was stirred at room temperature overnight and concentrated in vacuo. The crude protected peptide was isolated by column chromatography (EtOAc), further purified by RP HPLC (0.06% TFA in water-acetonitrile gradient). The remaining protective groups were removed by stirring in 50% TFA in dichloromethane for 2 hours at room temperature. Upon concentration in vacuo, the residue was triturated with water, filtered through a syringe filter and the filtrate was lyophilized to afford the target active peptide (as a TFA salt), the identity of which was confirmed by $^1$H NMR and HRMS.

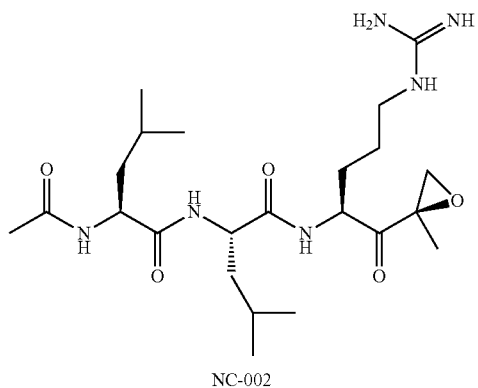 [SMILES: CC(=O)N[C@@H](CC(C)C)C(=O)N[C@@H](CC(C)C)C(=O)N[C@@H](CCCNC(=N)N)C(=O)[C@@]1(C)CO1]

NC-002

Ac-Leu-Leu-Arg-ek was prepared from Ac-Leu-Leu-OH and Boc-Arg(Pbf)-ek. $^1$H NMR (CD$_3$OD) δ 0.91 (br s, 6H), 0.96 (br s, 6H), 1.30-1.90 (m, 12H), 1.46 (s, 3H), 1.97 (s, 3H), 2.95 (d, 1H, J=5.0 Hz), 3.14-3.25 (m, 2H), 4.30-4.40 (m, 2H), 4.40-4.50 (m, 1H), 8.06 (d, 1H, J=8.0 Hz), 8.15 (d, 1H, J=8.0 Hz), 8.42-8.47 (br m, 1H). HRMS (ESI, m/z): calculated for [M+H]$^+$ (C$_{23}$H$_{43}$N$_6$O$_5$) 483.3289. found 483.3285.

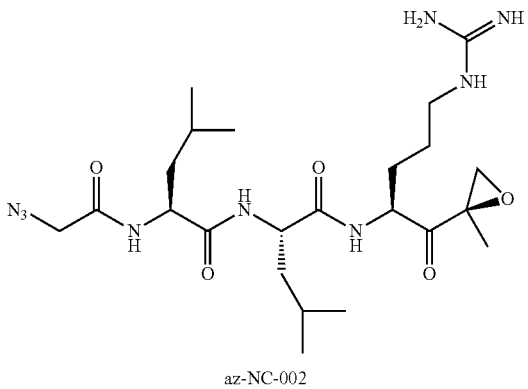 [SMILES: CC(C)C[C@H](NC(=O)CN=[N+]=[N-])C(=O)N[C@@H](CC(C)C)C(=O)N[C@@H](CCCNC(=N)N)C(=O)[C@@]1(C)CO1]

az-NC-002

Az-Gly-Leu-Leu-Arg-ek (SEQ ID NO:3) was prepared from az-Gly-Leu-Leu-OH and Boc-Arg(Pbf)-ek. $^1$H NMR (CD$_3$OD) δ 0.90-1.00 (m, 12H), 1.34-1.38 (m, 6H), 1.47 (s, 3H), 1.49-1.72 (m, 6H), 2.95 (d, 1H, J=5.0 Hz), 3.17-3.22 (m, 1H), 3.22 (d, 1H, J=5.5 Hz), 3.92 (s, 2H), 4.32-4.40 (m, 2H), 4.47 (dd, 1H, J=10.0, 3.5 Hz), 8.14 (d, 1H, J=8.0 Hz), 8.18 (d, 1H, J=8.0 Hz), 8.50-8.55 (m, 1H). HRMS (ESI, m/z): calculated for [M+H]$^+$ (C$_{23}$H$_{42}$N$_9$O$_5$) 524.3303. found 524.3299.

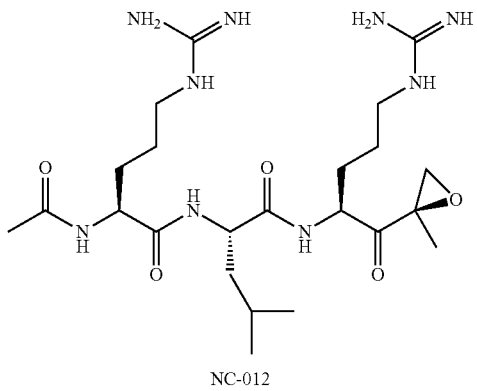 [SMILES: CC(=O)N[C@@H](CCCNC(=N)N)C(=O)N[C@@H](CC(C)C)C(=O)N[C@@H](CCCNC(=N)N)C(=O)[C@@]1(C)CO1]

NC-012

Ac-Arg-Leu-Arg-ek was prepared from Ac-Arg(Pbf)-Leu-OH and Boc-Arg(Pbf)-ek. $^1$H NMR (CD$_3$OD) δ 0.86-1.00 (m, 6H), 1.46 (s, 3H), 1.52-1.90 (m, 11H), 2.01 (s, 3H), 2.92 (d, 1H, J=5.0 Hz), 3.12-3.26 (m, 4H), 3.19 (d, 1H, J=5.0 Hz), 4.30-4.40 (m, 2H), 4.44-4.47 (m, 1H). HRMS (ESI, m/z): calculated for [M+H]$^+$ (C$_{23}$H$_{44}$N$_9$O$_5$) 526.3460. found 526.3458.

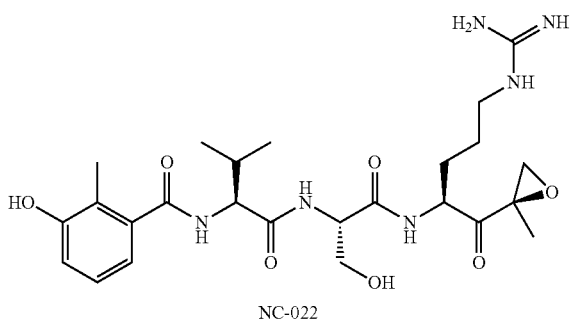 [SMILES: Cc1c(O)cccc1C(=O)N[C@H](C(=O)N[C@@H](CO)C(=O)N[C@@H](CCCNC(=N)N)C(=O)[C@@]1(C)CO1)C(C)C]

NC-022

HMB-Val-Ser-Arg-ek was prepared from HMB-Val-Ser(OtBu)-OH and Boc-Arg(Pbf)-ek. $^1$H NMR (CDCl$_3$) δ 1.01 (d, 3H, J=7.0 Hz), 1.04 (d, 3H, J=7.0 Hz). 1.34-1.40 (m, 1H), 1.47 (s, 3H), 1.46-1.55 (m, 1H), 1.58-1.68 (m, 2H), 1.82-1.91 (m, 1H), 2.10-2.19 (m, 1H), 2.20 (s, 3H), 2.95 (d, 1H, J=5.5 Hz), 3.12-3.20 (m, 2H), 3.23 (d, 1H, J=5.0 Hz), 3.76-3.80 (m, 2H), 4.32-4.35 (m, 1H), 4.44 (t, 1H, J=5.5 Hz), 4.56 (dd, 1H, J=10.0, 4.5 Hz), 6.82-6.85 (m, 2H), 7.05 (t, 1H, J=8.0 Hz). HRMS (ESI, m/z): calculated for [M+H]$^+$ (C$_{25}$H$_{39}$N$_9$O$_7$) 535.2875. found 535.2872.

Example 2

Assays and Cell Culture

Proteasome Purification and Assays.

26S proteasomes were purified from rabbit muscle using known methods (Screen, et al. (2010) supra). To determine inhibition of purified proteasomes, proteasomes were incubated with inhibitors for 30 minutes at 37° C. followed by assay of activity with fluorogenic substrates Suc-LLVY-amc (SEQ ID NO:8; chymotrypsin-like site), Ac-RLR-amc (trypsin-like site), and Ac-nLPnLD-amc (SEQ ID NO:9; caspase-like site) according to established methods (Geurink, et al. (2010) J. Med. Chem. 53:2319-23). NOVEX Bis-Tris gels (12%, Invitrogen) with MOPS running buffer were used for electrophoretic separation of catalytic subunits modified by active-site probes. Inhibition of active sites inside cells was assayed using luminescent PROTEASOMEGLO assay (Promega; Moravec, et al. (2009) Anal. Biochem. 387:294-302) according to known methods (Britton, et al. (2009) supra).

Enzyme activity of yeast 20S core particle was determined by continuously monitoring the hydrolysis of the fluorogenic substrate Suc-LLVY-amc (SEQ ID NO:8), ZLLRamc and ZLLE-amc (Bachem) for chymotrypsin-, trypsin-, and caspase-like activity in 20 mM Tris, 0.01% (w/v) SDS, pH 7.5, for 1 hour at room temperature ([E]$_0$=0.10 nM; [S]$_0$=250 μM). Proteasomes were pre-incubated with inhibitors for minutes, and inhibitors were present during activity assays. Fluorescence was measured at λ$_{exc}$=360, λ$_{em}$=460 nm using a Varian Cary Eclipse Fluorescence Spectrophotometer (Agilent Technologies). IC$_{50}$ values were obtained by plotting the percent inhibition against inhibitor concentration and fitting the experimental data to equation: % inhibition=100 [I]$_0$/(IC$_{50}$+[I]$_0$).

Cathespin Activity Assay.

Cathepsin B, H, L, S activity was measured with pan-cathepsin substrate Z-FR-amc (Kirschke & Wiederanders (1994) Methods Enzymol. 244:500-11) in extracts of cytosol-less cells at pH 6.0 (Screen, et al. (2010) supra). Cathepsin D activity was measured in cytosol-less extracts using SENSOLYTE 520 Cathepsin D Fluorometric Assay Kit (AnaSpec). Combined cathepsin D and E activity was measured using the same kit, in which cathepsin D substrate provided with the kit was replaced with 7-Methoxycoumarin-GKPILFFRLK(Dnp)-X'-NH$_2$ (SEQ ID NO:10; where "X'" stand for D-Arg) internally quenched fluorogenic substrate of cathepsin D and E. In this case, pH 3.0 assay buffer used for cell extraction. All activity observed using both procedures was inhibited by more than 98% by specific inhibitor of aspartic proteases pepstatin A.

Cell Culture.

RPMI-8226 and NCI-H929 cells were cultured in RPMI-1640 supplemented with 10% fetal bovine serum, penicillin, streptomycin, and plasmocin in 5% CO$_2$ humidified incubator. HEK-293T cells were cultured in DMEM containing 10% fetal calf serum, 10 units/mL penicillin, and 10 μg/mL streptomycin in a 7% CO$_2$ humidified incubator. Viability of multiple myeloma cells was measured with ALAMAR BLUE mitochondrial dye conversion assay. Viability of peripheral blood mononuclear cells (PBMNCs) was measured using CELL TITER-GLO luminescent cell viability assay (Promega), which is based on quantification of ATP present in the cells. Caspase-3/7 activity was measured using APO-ONE 3/7 homogeneous assay (Promega). (This assay uses Ac-DEVD-Rhodamine 110 (SEQ ID NO:11) cell-permeable fluorogenic substrate.)

Inhibition of Proteasome in Cultured Cells.

Proteasome inhibition in MM cells was measured with luminogenic substrates using PROTEASOMEGLO assay (Promega). RPMI-8226 or NCI-H929 cells (5×10$^5$/ml) were incubated with inhibitors for times indicated. An aliquot of culture was pelleted and medium was removed and replaced with PBS. The resulting cell suspension was mixed with luminogenic substrates in the manufacturer-provided lysis/ assay buffer. After 3 minutes mixing on an orbital shaker, the plate was incubated in the dark for additional 17 minutes, followed by the measurements of the luminescence, performed in triplicate for each substrate/data point. Data were analyzed as for purified proteasomes. Proteasome inhibition in HEK-293T cells was measured by a competition assays in living cells. Cells ($1\times10^6$ per well of a 6-well plate) were incubated with the inhibitors for 4 hours at 37° C. and this was followed by a 2 hour incubation with 5 µM BODIPY-TMR-epoxomicin. Subsequently, the medium was removed and the cells were washed with PBS and harvested. After flash freezing in liquid nitrogen, the cells were resuspended in 4 volumes of homogenization buffer (50 mM Tris pH 7.5, 250 mM sucrose, 5 mM $MgCl_2$, 1 mM DTT, 2 mM ATP, 0.025% digitonin), sonicated (12 W, 1 minute), and centrifuged at 16,000 rcf at 0° C. for 20 minutes. The supernatant was collected and the protein concentration was determined by the Bradford assay, and used to normalize gel loading. The samples were analysed by SDS-PAGE and fluorescent densitometry as described for competition experiment in cell lysates. $IC_{50}$ values were calculated from three independent experiments using GRAPHPAD PRISM software.

Inhibitors used in the assays included Bortezomib, which was purchased from LC laboratories, and Carfilzomib, which was synthesized using established methods (Demo, et al. (2007) supra; Zhou, et al. (2009) supra; Britton, et al. (2009) supra).

Isolation and Identification of Polypeptides Modified by az-NC-002.

Cells were treated with the activity-based site probe overnight and lysed with 50 mM Tris-HCl, 10% glycerol, 5 mM $MgCl_2$, 0.5 mM EDTA, 0.5% CHAPS, 1 mM ATP. After 1 hour treatment with 100 µM BioP (Verdoes, et al. (2008) *Chem. Biochem.* 9:1735-8), proteins were denatured with 1% SDS, followed by affinity purification of biotinylated polypeptides on streptavidin-coated magnetic beads. After on-beads trypsin digestion, samples were analyzed by LC-MS/MS (Florea, et al. (2010) *Chem. Biol.* 17:795-801). IRDYE 800 CW-conjugated streptavidin was purchased from Rockland, hsc71 antibodies from Abcam (Cat #19136), and β2 antibodies from Abgent (Cat #AP2914b).

Example 3

Design and Characterization of Inhibitors

Peptide epoxyketones were designed to target the trypsin-like site. Peptide epoxyketones are the most specific of the several structural classes of proteasome inhibitors (Kisselev & Goldberg (2001) supra; Groll & Huber (2004) supra; Kisselev (2008) *Chem. Biol.* 15:419-21). By forming a stable morpholino adduct with the proteasome catalytic N-terminal threonine, the inhibitors take specific advantage of the proteasome's unique mechanism for cleaving peptide bonds (Groll, et al. (2000) *J. Am. Chem. Soc.* 122:1237-1238). In more than a decade of research since the discovery of this class of proteasome inhibitors (Meng, et al. (1999) *Proc. Natl. Acad. Sci. USA* 96:10403-10408), no off-target effects of epoxyketones have been found.

Using conventional nomenclature (Britton, et al. (2009) supra), the inhibitors of trypsin-like sites disclosed herein are designated as NC-0X2, where "NC" stands for the Norris Cotton Cancer Center, "2" indicates that the compound inhibits β2 and/or β2i sites, and "X" indicates a variable character. The first compound, NC-002 (Ac-LLR-ek), is the epoxyketone derivative of leupeptin. Leupeptin (Ac-Leu-Leu-Arg-al) is a cell-permeable inhibitor of cysteine proteases. In the context of purified proteasome, this peptide aldehyde is a specific inhibitor of the trypsin-like sites (Kisselev, et al. (2006) supra; McCormack, et al. (1998) *Biochemistry* 37:7792-7800). Peptide aldehydes inhibit serine, cysteine, and threonine proteases. It was reasoned that replacing the aldehyde in leupeptin with a highly proteasome-specific epoxyketone (Groll, et al. (2000) supra) to generate Ac-LLR-amc (NC-002) would eliminate reactivity with lysosomal cysteine proteases, retain specificity to the trypsin-like sites, and not alter cell-permeability of the compound. The design of the second compound, NC-012 (Ac-RLR-ek), is based on the sequence of the best substrate of the trypsin-like site (Ac-RLR-amc; Kisselev & Goldberg (2005) *Methods Enzymol.* 398:364-378). The third inhibitor, NC-022 (Hmb-VSR-ek) has the same left-handed peptide fragment as the peptide vinyl-ester inhibitor of the trypsin-like sites reported in the literature (Marastoni, et al. (2005) supra) that has been shown to lack inhibitory activity (Screen, et al. (2010) supra). This fragment was selected because it was optimized to improve specificity towards these sites.

To enable the synthesis of the epoxyketone derivatives of arginine, the established procedure for the synthesis of leucine epoxyketones (Zhou, et al. (2009) supra) was modified to allow for proper protection of the guanidine functional group during the procedure.

The proteasome inhibitory potential of NC-002, NC-012, and NC-022 was initially determined on purified 26S proteasomes from rabbit muscles. All three compounds were potent and specific inhibitors of the trypsin-like sites. NC-012 was the most potent and specific in the series.

NCI-H929 multiple myeloma (MM) cells were subsequently treated overnight with NC-002, NC-012, and NC-022 and their proteasome inhibition profile was determined. NC-002 and NC-022 specifically inhibited trypsin-like activity at sub-micromolar concentrations, but much higher concentrations of NC-012, the most potent inhibitor of the purified enzyme, were required to achieve inhibition in live cells. This decrease in potency with live cells was attributed to poor cell permeability. For cell-permeable compounds, maximal inhibitory effect was achieved within 6-10 hours after addition of NC-022 or NC-002. Importantly, NC-002, the epoxyketone derivative of the cysteine protease inhibitor leupeptin, did not inhibit lysosomal cysteine proteases.

Multiple myeloma cells express constitutive proteasomes and immunoproteasomes, and substrates used for the measurement of activity were cleaved by both. To determine whether there were any differences in inhibition of constitutive proteasomes or immunoproteasomes by NC-002, NC-012, and NC-022, the fluorescent activity-based probe MV-151 (Verdoes, et al. (2006) *Chem. Biol.* 13:1217-1226) was used in a label-competition experiment. Extracts of RPMI-8226 MM cells (which express more immunoproteasomes than NCI-H929 cells) were treated first with the NC inhibitors and then with the MV-151 probe. This was followed by fractionation on SDS-PAGE to separate proteasome subunits and imaging to reveal those subunits labeled by the probe (i.e., unmodified by the inhibitors). All three inhibitors blocked modification of β2 and β2i sites by the probe to a similar extent. Thus, it was concluded that NC-002, NC-012, and NC-022 were equipotent inhibitors of the trypsin-like sites of constitutive and immunoproteasomes.

Example 4

Inhibitors of Trypsin-Like Sites Sensitize Cells to Inhibitors of Chymotrypsin-Like Sites NC-002, NC-012 and NC-022 were also used to characterize trypsin-likes sites as targets and co-targets of anti-neoplastic agents. For this purpose, NC-022 was used as it was the most potent cell-permeable inhibitor. First, it was determined whether selective inhibition of trypsin-like sites was sufficient to reduce cell viability. NCI-H929 cells were treated with NC-022 for 48 hours and cell viability was assayed with ALAMAR BLUE mitochondrial conversion dye. No loss of viability was detected even at concentrations that completely inhibited the trypsin-like sites. Thus, targeting trypsin-like sites was not sufficient to induce cytotoxicity in multiple-myeloma cells. It should be noted that NCI-H929 is the most sensitive to proteasome inhibitors among myeloma cell lines (Britton, et al. (2009) supra).

It was subsequently determined whether NC-022 sensitizes myeloma cells to inhibitors of the chymotrypsin-like sites. Several peptide epoxyketone inhibitors of the chymotrypsin-like sites have been developed (Britton, et al. (2009) supra; Geurink, et al. (2010) supra) and the most specific of these, a pentafluorophenylalanine-containing compound referred to as LU-005 (Geurink, et al. (2010) supra), was used in the experiments herein.

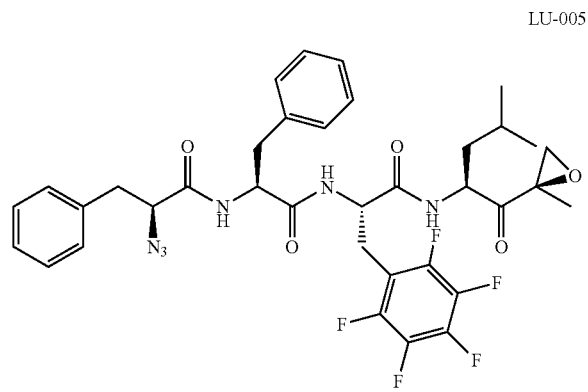 [SMILES: CC(C)C[C@H](NC(=O)[C@H](Cc1c(F)c(F)c(F)c(F)c1F)NC(=O)[C@H](Cc1ccccc1)NC(=O)[C@H](Cc1ccccc1)N=[N+]=[N-])C(=O)[C@@]1(C)CO1]

LU-005

In the first experiment, it was determined whether NC-022 sensitizes cells to LU-005, and what concentrations are needed to achieve this sensitization. Consistent with conventional treatment conditions (Britton, et al. (2009) supra), where it was demonstrated that a specific inhibitor of the caspase-like sites sensitizes myeloma cells to NC-005 (a specific inhibitor of chymotrypsin-like sites; Britton, et al. (2009) supra), cells were treated with LU-005 for 1 hour and then incubated in the presence of different concentrations of NC-022 for 48 hours, whereupon an ALAMAR BLUE assay for cell viability was performed. Dramatic dose-dependent sensitization was observed, with the $IC_{50}$ of LU-005 increasing up to 8.5-fold. This maximal sensitization was achieved at 3 µM NC-022, which caused 90% inhibition of the trypsin-like sites within 4-6 hours after addition of NC-022. NC-002 caused similar sensitization to NC-005. Thus, near-complete inhibition of the trypsin-like sites was needed to achieve maximal sensitization effect.

Example 5

Development of β2-Specific Activity-Based Probe

To further confirm that NC-002, NC-012 and NC-022 were specific for the trypsin-like sites and that the biological activity was not due to off-target effects, az-NC-002 was synthesized as an NC-002-derived, activity-based probe. NC-002 over NC-022 was selected for derivatization because it was easier to introduce an azido group into this molecule. Addition of the azido group did not alter the specificity of the inhibitor. Polypeptides modified by this probe were visualized on western blot after treating extracts of probe-treated NCI-H929 cells with azido-reactive biotinylated phosphane (BioP) in a Staudinger-Bertozzi ligation (Ovaa, et al. (2003) Angew Chem. Int. Ed. Engl. 42:3626-3629). One major az-NC-002-specific streptavidin-reactive band was detected. This matched the size of the band of the β2 subunit, which harbors the catalytic threonines of the trypsin-like sites. A weaker band of slightly lower mobility, matching the mobility of β2i band, was also detected. Corroborating that these bands were of proteasomal subunits, az-NC-002 treatment prevented subsequent modification of β2 and β2i subunits by another proteasome-specific probe (Ada-K(Bio)-Ahx$_3$L$_3$VS). A number of endogenously biotinylated proteins in the 70-100 kDa region were also detected and can serve as a loading control.

To further confirm that the probe covalently modified β2 and β2i subunits, proteasome was denatured after BioP modification, biotinylated polypeptides were isolated on streptavidin beads, and bound polypeptides were identified by mass-spectrometry after on-beads trypsin digestion. Peptides derived from β2 and β2i subunits were present in the samples isolated from extracts of the probe-treated cells but not from extracts of the control cells. No peptides derived from other catalytic subunits were detected. Thus, it was concluded that az-NC-002 was a trypsin-like site-specific activity-based probe.

Unexpectedly, several other polypeptides were also reproducibly identified as specific az-NC-002 targets. These included the aspartic protease cathepsin D (29 kDa), molecular chaperone hsc71 (71 kDa), and thioredoxin domain-containing protein TXNDC5 (48 kDa). Of these, lysosomal aspartic protease cathepsin D (Benes, et al. (2008) Crit. Rev. Oncol. Hematol. 68:12-28) was of greatest concern. It has the same molecular weight as the β2 subunit, so some of the streptavidin-reactive material in the β2-band may have been cathepsin D. To determine the significance of this potential off-target effect, inhibition of cathepsin D was measured by az-NC-002; however no significant inhibition could detected. It was concluded that this probe either reacts with cathepsin D outside of the active site or inhibits a small fraction of the enzyme, detectable in the mass-spectrometry experiment but not in the activity assay. Similarly, NC-022 did not inhibit cathepsin D even at concentrations as high as 27 µM. Thus, chemical modification of cathepsin D is unlikely to contribute to the biological effects of the NC compounds.

There were no major streptavidin-reactive az-NC-002-specific bands in the 45-50 kDa and ~70 kDa region of the gel, where two other targets of az-NC-002, TXNDC5 and hsc71, migrate. Probe modification of these proteins was responsible for one of the background bands. Western blot analysis was used to determine which fraction of cellular hsc71 binds to streptavidin beads in extracts of az-NC-002-treated cells. Under conditions when most of β2-antibody reactive material was detected in streptavidin-bound fraction, the majority of hsc71-antibody reactive material was detected in the streptavidin-unbound fractions. Thus, az-NC-022 modifies a small fraction of hsc71 and is therefore very unlikely to affect the overall protein-folding capacity of the cell.

Example 6

NC-022 as a Potent Sensitizer of Myeloma Cells to LU-005

It was also determined whether NC-022 sensitizes other MM cells to LU-005 and whether it is a more potent sensitizer than a specific inhibitor of caspase-like sites NC-001 (Britton, et al. (2009) supra). In a parallel set of experiments, it was tested whether co-inhibiting caspase-like and trypsin-like sites suffices to induce cytotoxicity in the absence of inhibition of the chymotrypsin-like sites and whether such dual inhibition is a stronger sensitizer to LU-005 than inhibition of the trypsin-like sites alone. Four additional myeloma cell lines, MM1.R, RPMI-8226, KMS-18, and KMS-12-BM, were selected for these experiments. These cell lines vary up to 40-fold in their sensitivity to bortezomib and NC-005 (Britton, et al. (2009) supra). In all experiments, NC-022 was used at a concentration that inhibited trypsin-like activity by more than 90% after a 6-hour incubation.

In all MM cell lines, NC-022 reduced the $IC_{50}$ for LU-005 by 4-10-fold. In three (MM1.R, RPMI-8226, KMS-18), NC-022 caused similar sensitization as NC-001. In two others (NCI-H929 and KMS-12-BM), NC-022 was a more potent sensitizer than NC-001. Thus, the trypsin-like sites are important co-targets of anti-neoplastic drugs in multiple myeloma cells; in fact, they are better co-targets than the caspase-like sites.

To confirm that LU-005 functioned as a specific inhibitor of the chymotrypsin-like sites and to determine whether sensitization occurred upon clinically achievable inhibition of the chymotrypsin-like sites, inhibition of all sites was measured at the end of 1 hour treatment with LU-005 (Table 2). In patients treated with bortezomib, inhibition of the chymotrypsin-like sites that can be achieved at maximal tolerated doses does not exceed 70% (Hamilton, et al. (2005) *J. Clin. Oncol.* 23:6107-16); in patients treated with carfilzomib, it approaches 90% (O'Connor, et al. (2009) supra). As can be seen from Table 2, in all but the KMS-18 cell line, sensitization by NC-022 was observed upon clinically achievable 50-80% inhibition of the chymotrypsin-like sites. Thus, sensitization of myeloma cells to specific inhibitors of the chymotrypsin-like sites by NC-022 is of potential clinical significance.

Cells were treated with LU-005 for 1 hour, followed by measurement of peptidase activities; a fraction of the cells was cultured in the presence of NC-022, of NC-022 and NC-001, or of none of the inhibitors for 48 hours, whereupon cell viability was measured. Values are averages±S.E.M. of two (activity) or three (viability) independent measurements. Negative values indicate activation.

Example 7

Effects of Combined Inhibition of Caspase-Like and Trypsin-Like Sites

Due to the lack of effective, selective, and cell-permeable inhibitors of the trypsin-like sites, the effects of combined inhibition of the trypsin-like and caspase-like sites (in the absence of inhibition of the chymotrypsin-like sites) on growth and viability of mammalian cells could not be studied hitherto. It was observed that continuous exposure to a mixture of NC-022 and NC-001 (at concentrations at which caspase-like and trypsin-like sites are both blocked by more than 90%) reduced cell viability by 20-50%. Proteasome inhibitors block cell proliferation and induce apoptosis. This moderate decrease could be a consequence of inhibition of cell proliferation without cell death. To determine whether apoptosis occurs, caspase activation in the NCI-H929 and MM1.R cell lines was measured. It was found that treatment with a combination of NC-001 and NC-002, in contrast to LU-005 treatment, did not cause any significant increase in caspase activity. Therefore, it was concluded that the moderate decrease in viability in cells co-treated with NC-001 and NC-002 was not due to apoptosis and most likely reflected inhibition of cell proliferation. This is the first example of a biological effect on mammalian cells due to inhibition of the caspase-like and trypsin-like sites in the absence of inhibition of the chymotrypsin-like sites.

TABLE 2

| Cell line | LU-005 (μm) | Viability (% control) | | | Inhibition of active sites (% control) | | |
|---|---|---|---|---|---|---|---|
| | | −NC-022 | +NC-022 | +NC-002 & NC-001 | β5 | β2 | β1 |
| NCI-H929 | 0.11 | 30 ± 2 | 2 ± 1 | 0.65 ± 0.25 | 86 ± 3 | 11 ± 4 | 6 ± 8 |
| | 0.043 | 80 ± 8 | 10 ± 2 | 1.5 ± 0.5 | 72 ± 8 | 6 ± 4 | 15 ± 20 |
| | 0.011 | 94 ± 11 | 48 ± 3 | 10 ± 4 | 48 ± 5 | −6 ± 1 | 5.5 ± 4.5 |
| | 0.004 | 100 ± 13 | 69 ± 0 | 36 ± 14 | 22 ± 11 | −13 ± 7 | −7 ± 10 |
| | 0.0014 | 97 ± 9 | 77 ± 2 | 50 ± 17 | 22 ± 4 | −9 ± 2 | −14 ± 15 |
| MM1.R | 0.11 | 47 ± 42 | 1.7 ± 0.2 | 1.2 ± 1.2 | 76 ± 3 | 23 ± 4 | 27 ± 5 |
| | 0.043 | 88 ± 20 | 18.5 ± 5.5 | 2.8 ± 1.5 | 54 ± 12 | 5 ± 11 | 6 ± 12 |
| | 0.011 | 106 ± 4 | 57 ± 10 | 15 ± 9 | 31 ± 10 | 5 ± 1 | 3 = 16 |
| | 0.004 | 102 ± 4 | 66 ± 1 | 26 ± 6 | 17 ± 4 | 6.5 ± 0.5 | 6 ± 8 |
| RPMI-8226 | 1.0 | 10 ± 10 | 6 ± 3 | 1 ± 0 | 82 ± 16 | 22 ± 19 | 37 ± 4 |
| | 0.33 | 94 ± 1 | 31 ± 9 | 4.6 ± 0.7 | 62 ± 32 | 13 ± 11 | 37 ± 15 |
| | 0.11 | 108 ± 4 | 95 ± 2 | 39 ± 5 | 49 ± 30 | 3 ± 5 | 23 ± 2 |
| | 0.037 | 109 ± 2 | 104 ± 5 | 76 ± 3 | 45 ± 26 | 1 ± 17 | 16 ± 7 |
| | 0.012 | 109 ± 1 | 108 ± 4 | 82 ± 11 | 16 ± 8 | −21 ± 4 | −34 ± 5 |
| KMS-12-BM | 1.0 | 27 ± 6 | 1.5 ± 0.1 | 1 ± 0 | 95 ± 2 | 29 ± 7 | 11 ± 16 |
| | 0.33 | 80 ± 9 | 12 ± 2 | 2 ± 0 | 81 ± 3 | 3 ± 18 | 6 ± 12 |
| | 0.11 | 94 ± 16 | 65 ± 2 | 20 ± 4 | 56 ± 9 | 4.7 ± 1.1 | 3 ± 16 |
| | 0.037 | 89 ± 8 | 90 ± 5 | 50 ± 2 | 48 ± 9 | −12 ± 1 | −1 ± 5 |
| | 0.012 | 101 ± 5 | 104 ± 9 | 79 ± 6 | 16 ± 8 | −21 ± 3.5 | −34 ± 5 |
| KMS-18 | 9.0 | 45 ± 8 | 17.5 ± 7.5 | 0.8 ± 0.2 | 97 ± 1 | 62 ± 5 | 42 ± 2 |
| | 3.0 | 72 ± 2 | 24 ± 8 | 1 ± 0.1 | 94 ± 4 | 50 ± 14 | 39 ± 12 |
| | 1.0 | 88 ± 16 | 29 ± 12 | 8 ± 4 | 85 ± 6 | 38 ± 5 | 32 ± 4 |
| | 0.33 | 108 ± 0 | 106 ± 16 | 33 ± 20 | 69 ± 8 | 24 ± 6 | 29 ± 7 |
| | 0.11 | 108 ± 1 | 106 ± 4 | 56 ± 16 | 47 ± 4 | 12 ± 16 | 21 ± 16 |
| | 0.037 | 108 ± 1 | 104 ± 3 | 79 ± 14 | 14 | −13 ± 13 | 0 ± 8 |

The effects of the mixture of NC-001 and NC-022 on MM cells sensitivity to LU-005 were subsequently determined. As in the previous experiments, cells were treated with LU-005 for 1 hour and then cultured with a NC-001/NC-022 mixture after removal of LU-005. The mixture of NC-001 and NC-022 appeared to be a much stronger sensitizer than NC-022 alone. Notably, there was always a concentration of LU-005 at which a mixture of NC-001 and NC-002 caused a dramatic loss of cell viability as compared to the effect of LU-005 as a single agent (i.e., from 80-100% to 10-20%). At this concentration, LU-005 inhibited chymotrypsin-like sites by a clinically achievable 50-85% (Table 2). A mixture also sensitized cells at much lower concentrations of LU-005 (i.e., upon much smaller inhibition of chymotrypsin-like sites, Table 2) than either NC-001 or NC-002 alone.

Example 8

NC-022 Specifically Sensitizes Myeloma Cells to Bortezomib and Carfilzomib

To further strengthen the clinical relevance of data herein, it was determined whether NC-022 sensitizes MM cells to the FDA-approved proteasome inhibitor bortezomib and to carfilzomib, a second-generation peptide epoxyketone proteasome inhibitor undergoing phase II-III clinical trials (Demo, et al. (2007) supra; O'Connor, et al. (2009) supra). Two cell lines were used in these experiments, one of the most bortezomib-sensitive (NCI-H929), and one of the most bortezomib-resistant (KMS-12-BM) cell lines (Britton, et al. (2009) supra). Both cell lines were sensitized to the two agents (Table 3). In NCI-H929 cells, sensitization to both compounds occurred upon clinically achievable proteasome inhibition (Table 4). In KMS-12-BM cells, sensitization to bortezomib, although more dramatic than in NC-H929 cells, was observed above clinically achievable inhibition of the chymotrypsin-like sites. Sensitization to carfilzomib was observed at clinically achievable levels.

TABLE 3

| Inhibitor | Inhibitor Conc. (nM) | Cell line | Viability (% control) −NC-022 | +NC-022 |
|---|---|---|---|---|
| Bortezomib | 100 | NCI-H929 | 2.9 ± 1.5 | 1.9 ± 1.5 |
|  | 33 |  | 53 ± 17 | 19 ± 19 |
|  | 11 |  | 106 ± 2 | 65 ± 1 |
|  | 3.7 |  | 107 ± 5 | 85 ± 3 |
|  | 900 | KMS-12-BM | 14 ± 12 | 3.8 ± 2.5 |
|  | 300 |  | 66 ± 9 | 14 ± 11 |
|  | 100 |  | 92 ± 9 | 42 ± 10 |
|  | 33.3 |  | 98 ± 13 | 72 ± 1 |
| Carfilzomib | 33 | NCI-H929 | 30 ± 11 | 4 ± 2 |
|  | 11 |  | 78 ± 15 | 14 ± 8 |
|  | 3.7 |  | 99 ± 9 | 36 ± 15 |
|  | 900 | KMS-12-BM | 41 ± 7 | 9 ± 1 |
|  | 300 |  | 71 ± 2 | 15 ± 1 |
|  | 100 |  | 83.5 ± 3 | 27 ± 5 |
|  | 33 |  | 91 ± 3 | 40 ± 3 |
|  | 11 |  | 95 ± 3 | 69 ± 2 |

*Cells were treated with bortezomib and carfilzomib for 1 hour. NC-022 was added and viability was measured 48 hours after the start of the experiment.

TABLE 4

| | | | Inhibition of active sites (% control) | | | | | |
|---|---|---|---|---|---|---|---|---|
| | | | Chymotrypsin-like sites Time after start of experiment | | | Trypsin-like sites Time after start of experiment | | |
| Inhibitor | Conc. (nM) | Cell line | 1 h* | 6 h −NC-022 | 6 h +NC-022 | 1 h | 6 h −NC-022 | 6 h +NC-022 |
| Bortezomib | 100 | NCI-H929 | 96 ± 2 | 86 ± 1 | 93 ± 2 | 36 ± 17 | 45 ± 2 | 96 ± 1 |
|  | 33 |  | 89 ± 2 | 85 ± 4 | 48 ± 35 | 26 ± 15 | 31 ± 0 | 94 ± 1 |
|  | 11 |  | 64 ± 7 | 41 ± 3.5 | 34 ± 29 | 8 ± 11 | 14 ± 2 | 93 ± 2 |
|  | 3.7 |  | 9 ± 7 | 13 ± 1 | 14 ± 13 | 0 ± 7 | 6 ± 4 | 93 ± 2 |
|  | 900 | KMS-12-BM | 93 ± 5 | 84 ± 16 | 88 ± 5 | 28 ± 5 | 26 ± 19 | 93 ± 1 |
|  | 300 |  | 93 ± 3 | 76 ± 18 | 83 ± 6 | 22 ± 12 | 24 ± 18 | 91 ± 2 |
|  | 100 |  | 90 ± 6 | 64 ± 23 | 75 ± 6 | 19 ± 3 | 15 ± 11 | 92 ± 1 |
|  | 33.3 |  | 82 ± 8 | 56 ± 24 | 62 ± 7 | 10 ± 11 | 8 ± 15 | 92 ± 0 |
| Carfilzomib | 33 | NCI-H929 | 75 ± 17 | 95 ± 7 | 71 ± 23 | 17 ± 8 | 46 ± 24 | 94 ± 3 |
|  | 11 |  | 39 ± 35 | 89 ± 11 | 52 ± 32 | 0 ± 14 | 39 ± 36 | 93 ± 2 |
|  | 3.7 |  | 14 ± 43 | 65.5 | 41 ± 29 | −7 ± 18 | 3 | 93 ± 3 |
|  | 900 | KMS-12-BM | 98 ± 3 | 97 ± 0 | 99 ± 4 | 75 ± 14 | 72 ± 2 | 94 ± 3 |
|  | 300 |  | 97 ± 3 | 97 ± 1 | 95 ± 4 | 49 ± 18 | 69 ± 2 | 93 ± 2 |
|  | 100 |  | 95 ± 3 | 97 ± 1 | 90 ± 3 | 18 ± 8 | 62 ± 2 | 94 ± 2 |
|  | 33 |  | 90 ± 3 | 97 ± 1 | 84 ± 6 | 0 ± 11 | 45 ± 4 | 91 ± 2 |
|  | 11 |  | 75 ± 6 | 67 ± 17 | 63 ± 13 | −3 ± 10 | 5 ± 25 | 91 ± 2 |

*Cells were treated with bortezomib and carfilzomib for 1 hour, and activity was measured immediately after washout of the drug. NC-022 was added, and 5 hours after NC-022 addition, proteasome activity was measured again.

Note that trypsin-like activity was inhibited by >90% but inhibition of the chymotrypsin-like activity was not altered by NC-022 treatment.

To assess whether co-inhibition of trypsin-like sites increases toxicity to normal cells, it was determined whether NC-022 increased toxicity of bortezomib and carfilzomib to PBMNCs. NC-022 did not sensitize cells from any of the three donors to either of two agents. This lack of sensitization was unexpected because NC-001 sensitizes PBMNCs to inhibitors of the chymotrypsin-likes sites (Britton, et al. (2009) supra). Thus, NC-022 selectively sensitizes malignant MM cells to bortezomib and carfilzomib.

Example 9

Synthesis of Additional Epoxyketones and Vinyl Sulfones with 4-Aminomethylene-L-Phenylalanine in the P1 Position This Example describes the development of inhibitors targeting the trypsin-like subunits on (β2 and β2i) by modification of the P1 site, which plays a key role in subunit binding, with basic residues. The general structure of these inhibitors is based on the tripeptide vinyl sulfone Z-L₃VS 3, which targets all proteasome active sites (Bogyo, et al. (1997) *Proc. Natl. Acad. Sci. USA* 94:6629-6634). The P1 leucine side chain was replaced by a benzyl amine (Scheme 2). In addition to the vinyl sulfone electrophilic trap, the epoxyketone featured by natural proteasome inhibitor epoxomicin was incorporated as well, since it displays a specific reactivity towards proteasome active sites (Kisselev & Goldberg (2001) *Chem. Biol.* 8:739-758; Kim, et al. (1999) *Bioorg. Med. Chem. Lett.* 9:3335-3340). The N-terminal benzyloxycarbonyl group was replaced by the structurally related azidophenylalanine, which opens the possibility for additional modifications (Ovaa, et al. (2003) *Angew. Chem. Int. Ed.* 42:3626-3629; van Swieten, et al. (2005) *Org. Biomol. Chem.* 3:20-27; Verdoes, et al. (2009) *Eur. J. Org. Chem.* 3301-3313), yet it does not significantly influence the inhibitory properties compared to the benzyloxycarbonyl group.

The inhibitors targeting the trypsin-like subunits are shown below.

General Procedures for Synthesis.

Tetrahydrofuran was distilled over LiAlH₄ prior to use. Acetonitrile (ACN), dichloromethane (DCM), N,N-dimethylformamide (DMF), methanol (MeOH), diisopropylethylamine (DiPEA) and trifluoroacetic acid (TFA) were of peptide synthesis grade, purchased at Biosolve, and used as received. All general chemicals (Fluka, Acros, Merck, Aldrich, Sigma) were used as received. O-(1H-6-Chlorobenzotriazolyl)-1,1,3,3-tetramethyluronium hexafluorophosphate (HCTU) was purchased at Iris Biotech (Marktrewitz, Germany). Traces of water were removed from reagents used in reactions that require anhydrous conditions by co-evaporation with toluene. Solvents that were used in reactions were stored over 4 Å molecular sieves, except methanol and acetonitrile which were stored over 3 Å molecular sieves. Column chromatography was performed on Screening Devices b.v. Silica Gel, with a particle size of 40-63 μm and pore diameter of 60 Å. The eluents toluene, ethyl acetate and petroleum ether (40-60° C. boiling range) were distilled prior to use. TLC analysis was conducted on Merck aluminium sheets (Silica gel 60 F₂₅₄). Compounds were visualized by UV absorption (254 nm), by spraying with a solution of $(NH_4)_6Mo_7O_{24} \cdot 4H_2O$ (25 g/L) and $(NH_4)_4Ce(SO_4)_4 \cdot 2H_2O$ (10 g/L) in 10% sulfuric acid, a solution of KMnO₄ (20 g/L) and K₂CO₃ (10 g/L) in water, or ninhydrin (0.75 g/L) and acetic acid (12.5 mL/L) in ethanol, where appropriate, followed by charring at ca. 150° C. ¹H- and ¹³C-NMR spectra were recorded on a Bruker AV-400 (400 MHz) spectrometer. Chemical shifts are given in ppm (δ) relative to tetramethylsilane, CD₃OD or CDCl₃ as internal standard. High resolution mass spectra were recorded by direct injection (2 μL of a 2 μM solution in water/acetonitrile 50/50 (v/v) and 0.1% formic acid) on a mass spectrometer (Thermo Finnigan LTQ ORBITRAP) equipped with an electrospray ion source in positive mode (source voltage 3.5 kV, sheath gas flow 10, capillary temperature 250° C.) with resolution R=60,000 at m/z 400 (mass range m/z=150-2,000) and dioctylpthalate (m/z=391.28428) as a "lock mass". The high resolution mass spectrometer was calibrated prior to measurements with a

SCHEME 2

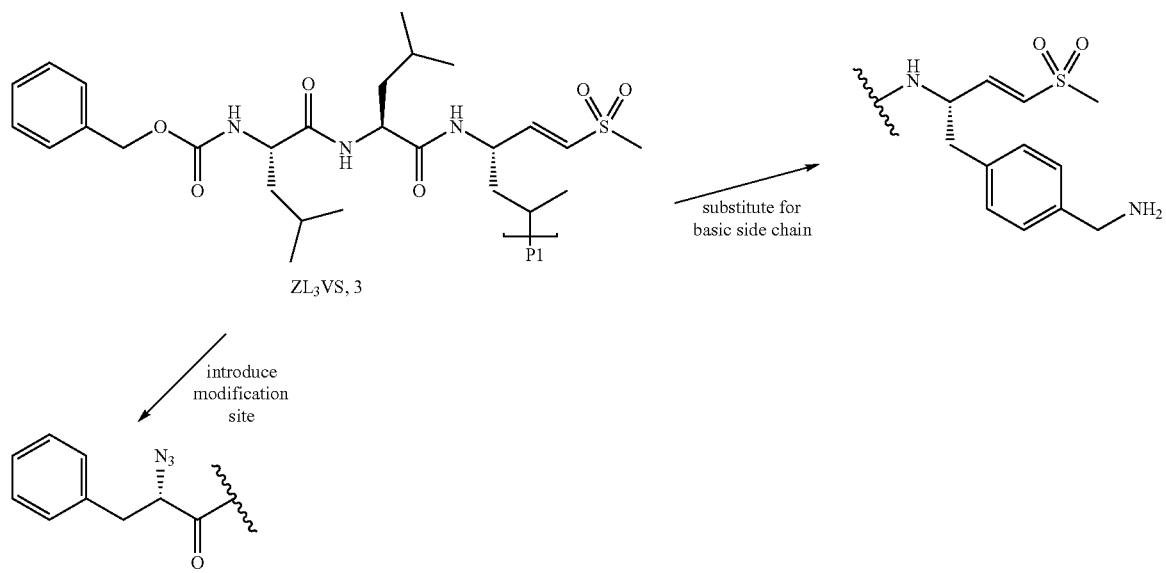

calibration mixture (Thermo Finnigan). Optical rotations $[\alpha]_D^{23}$ were recorded on a Propol automatic polarimeter. LC-MS analysis was performed on a Finnigan Surveyor HPLC system with a Gemini C18 50×4.60 mm column (detection at 200-600 nm), coupled to a Finnigan LCQ Advantage Max mass spectrometer with ESI. The applied buffers were $H_2O$, ACN and 1.0% aq. TFA. HPLC purifications were performed on a Gilson HPLC system coupled to a Phenomenex Gemini 5 μm 250×10 mm column and a GX281 fraction collector. The applied buffers were: 0.1% aq. TFA and ACN.

Procedure I: Azide Coupling of $N_3$Phe-Leu-Leu-NHNH$_2$ or HMB-Val-Ser(tBu)-NHNH to an Amine-Warhead Followed by Acidic Deprotection.

$N_3$Phe-Leu-Leu-NHNH$_2$38 or HMB-Val-Ser(tBu)-NHNH$_2$ (1 eq.) was dissolved in a 9:1 mixture of DCM/DMF (10 mL/mmol) and cooled to −35° C. To this were added tert-butylnitrite (1.1 eq.) and HCl (2.8 eq. as a 4 M solution in 1,4-dioxane) and the mixture was stirred for 3 hours at −35° C. Next, a mixture of the deprotected amine (1.1 eq.) and DiPEA (5 eq.) in DMF (1 mL) were added. The reaction was slowly warmed to room temperature and stirred for another 12 hours before being diluted with DCM and extracted with 1M aq. HCl (2×), saturated aq. $Na_2CO_3$ (2×) and brine. After drying ($MgSO_4$) and concentrating the obtained crude product was dissolved in DCM (2.5 mL/mmol). TFA (2.5 mL/mmol) was added and the mixture was stirred for 30 minutes, after which it was concentrated under reduced pressure in the presence of toluene (3×). The obtained crude product was purified by RP-HPLC.

$N_3$-Phe-Leu-Leu-NHNH$_2$ (38).

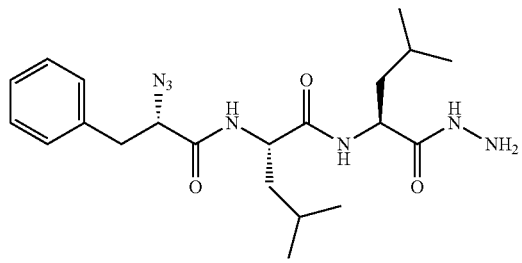 [SMILES: CC(C)C[C@H](NC(=O)[C@H](Cc1ccccc1)N=[N+]=[N-])C(=O)N[C@@H](CC(C)C)C(=O)NN]

This compound was synthesized via general Boc-based peptide coupling procedures using HCTU from H-Leu-OMe, Boc-Leu-H and $N_3$-Phe-H. The last step involved the introduction of the hydrazide by stirring of a mixture containing tripeptide $N_3$-Phe-Leu-Leu-OMe (1.51 g, 3.49 mmol) and hydrazine monohydrate (30 eq., 105 mmol, 5.1 mL) in MeOH (30 mL) for 15 hours at room temperature. Compound 38 was obtained after coevaporation of the mixture with toluene (3×) as a colourless solid (yield: 1.51 g, 3.49 mmol, quant.). LC-MS: $R_t$ (min): 6.87 (ESI-MS (m/z): 432.13 (M+H$^+$)).

(S)-2-(((Benzyloxy)carbonyl)amino)-3-(4-((2,2,2-trichloroacetamido)methyl)phenyl)propanoic acid (9)

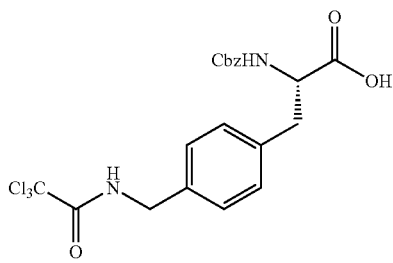

L-Phenylalanine (8, 8.26 g, 50.0 mmol) was added in portions to concentrated $H_2SO_4$ (35 mL) maintaining the temperature at 25° C. N-(hydroxymethyl)trichloroacetamide (1.05 eq., 52.5 mmol, 10.1 g) was added in portions while maintaining the temperature at 20-25° C. The cooling bath was removed and the light-brown cloudy solution was stirred at room temperature for 1 hour. The reaction mixture was added to ice (500 mL) and the pH was adjusted to pH 5.5 with 8 M aq. NaOH solution while maintaining the quench temperature at 15-20° C. The white solid was filtered off and washed with ice-cold $H_2O$. The residue was dissolved in a 1:1 mixture of $H_2O$/dioxane (100 mL) and the pH was adjusted to pH 9 by addition of $Na_2CO_3$. Next, benzyl chloroformate (7.32 mL, 50.0 mmol) was added and the mixture was stirred for 4 hours. Concentrated aq. HCl was added until pH 1 and the mixture was extracted twice with EtOAc. The combined organic layers were extracted with brine, dried ($MgSO_4$) and concentrated under reduced pressure. The resulting crude product was purified by column chromatography (25%->60% EtOAc/PE) and the title compound was obtained as a colourless solid (yield: 8.29 g, 17.5 mmol, 35%). $^1$H NMR (400 MHz, CDCl$_3$): δ=10.16 (s, 1H), 7.31-7.21 (m, 6H), 7.13 (d, J=7.88 Hz, 2H), 7.09 (d, J=7.97 Hz, 2H), 5.58 (d, J=8.21 Hz, 1H), 5.05-4.97 (m, 2H), 4.60 (dd, J=13.68, 6.42 Hz, 1H), 4.40 (d, J=5.54 Hz, 2H), 3.14 (dd, J=13.57, 4.65 Hz, 1H), 3.01 (dd, J=13.81, 6.53 Hz, 1H) ppm. $^{13}$C NMR (100 MHz, CDCl$_3$): δ=174.70, 162.06, 155.85, 135.68, 135.31, 135.15, 129.57, 128.31, 128.28, 127.76, 127.57, 92.30, 66.91, 54.41, 44.54, 36.99 ppm.

(S)-2-(((Benzyloxy)carbonyl)amino)-3-(4-(((tert-butoxycarbonyl)amino)methyl)phenyl)propanoic acid (10)

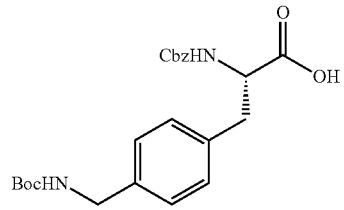 [SMILES: CC(C)(C)OC(=O)NCc1ccc(C[C@H](NC(=O)OCc2ccccc2)C(=O)O)cc1]

Compound 9 (2.82 g, 5.94 mmol) was treated with 20% w/w NaOH in $H_2O$/EtOH (1:1) for 1 hour after which TLC analysis indicated complete conversion of starting material. Next, 3 M aq. HCl was added until pH 7 and the mixture was concentrated under reduced pressure. The resulting crude compound was dissolved in THF (40 mL) and cooled to 0° C. Boc$_2$O (1.5 eq., 8.91 mmol, 2.0 g) was added and the solution was basified by addition of $Na_2CO_3$ until pH 9. The mixture was stirred at room temperature for 3 hours, after which it was acidified with 10% w/v aq. HCl until pH and extracted with EtOAc (3×). The combined organic layers were extracted with brine, dried over $MgSO_4$ and concentrated under reduced pressure. The resulting crude mixture was purified by column chromatography (20%->100% EtOAc/PE) and the title compound was obtained as a colourless solid (yield: 1.90 g, 4.45 mmol, 75%). $^1$H NMR (400 MHz, CDCl$_3$): δ=9.32 (s, 1H), 7.36-7.28 (m, 5H), 7.16-7.02 (m, 4H), 5.33 (d, J=7.64 Hz, 1H), 5.09 (q, J=12.32, 12.32, 12.29 Hz, 2H), 4.95 (s, 1H), 4.65 (d, J=6.41 Hz, 1H), 4.26-4.19 (m, 2H), 3.20-3.04 (m, 2H), 1.45 (s, 9H) ppm. $^{13}$C NMR (100 MHz, CDCl$_3$): δ=174.79, 156.16, 155.77, 137.47, 136.15, 134.80, 129.61, 128.46, 128.14, 128.03, 127.69, 79.85, 66.99, 54.52, 44.31, 37.30, 28.36 ppm.

(S)-2-(((Benzyloxy)carbonyl)amino)-3-(4-(((tert-butoxycarbonyl)amino)methyl)phenyl)-N-methoxy-N-methylpropionamide (11)

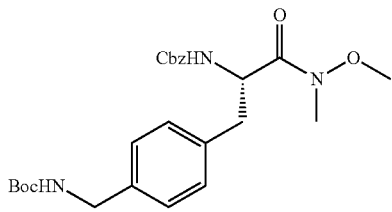 [SMILES: CON(C)C(=O)[C@H](Cc1ccc(CNC(=O)OC(C)(C)C)cc1)NC(=O)OCc1ccccc1]

Carboxylic acid 10 (4.45 g, 10.4 mmol) was dissolved in DCM (75 mL). To this were added NH(Me) OMe.HCl (1.5 eq., 15.6 mmol, 1.55 g), HCTU (1.5 eq., 15.6 mmol, 6.45 g) and DiPEA (4.5 eq., 46.7 mmol, 7.72 mL) and the mixture was stirred for 2 hours until TLC analysis indicated a completed reaction. The solvent was evaporated under reduced pressure and the residue was dissolved in EtOAc. This was extracted with 1 M aq. HCl (2×), saturated aq. Na$_2$CO$_3$ (2×) and brine, dried over MgSO$_4$ and concentrated under reduced pressure. The product was purified by column chromatography (10%->75% EtOAc/PE) and obtained as colourless oil (yield: 4.81 g, 10.2 mmol, 98%). $^1$H NMR (400 MHz, CDCl$_3$): δ=7.29-7.22 (m, 5H), 7.14 (d, J=8.12 Hz, 2H), 7.09 (d, J=8.17 Hz, 2H), 6.02 (d, J=8.49 Hz, 1H), 5.35 (s, 1H), 5.00 (dd, J=28.51, 12.34 Hz, 2H), 4.96-4.94 (m, 1H), 4.21 (d, J=5.20 Hz, 2H), 3.62 (s, 3H), 3.10 (s, 3H), 3.02 (dd, J=13.63, 5.63 Hz, 1H), 2.85 (dd, J=13.27, 7.70 Hz, 1H), 1.43 (s, 9H) ppm. $^{13}$C NMR (100 MHz, CDCl$_3$): δ=171.54, 155.50, 137.23, 136.02, 135.04, 129.04, 127.92, 127.48, 127.42, 126.98, 78.64, 66.11, 61.01, 51.78, 43.76, 37.46, 31.52, 27.96 ppm. [α]$_D^{23}$=+10.1 (c=1, CHCl$_3$). HRMS: calcd. for C$_{25}$H$_{33}$N$_3$O$_6$ 472.24421 [M+H]$^+$. found 472.24402.

(S)-Benzyl (1-(4-((tert-butyloxycarbonyl)amino)methyl)phenyl)-4-methyl-3-oxopent-4-en-2-yl)carbamate (12)

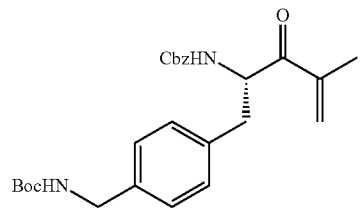 [SMILES: C=C(C)C(=O)[C@H](Cc1ccc(CNC(=O)OC(C)(C)C)cc1)NC(=O)OCc1ccccc1]

2-Bromopropene (3.5 eq., 14.0 mmol, 1.25 mL) was dissolved in THF (50 mL) and cooled to −78° C. tBuLi (6.5 eq., 26.0 mmol, 16.3 mL; 1.6 M in hexane) was added slowly and the mixture was stirred for 1 hour at −78° C. after which Weinreb amide 11 (1 eq., 4.0 mmol, 1.89 g) was added in THF (5 mL). The mixture was allowed to warm to −20° C. in 6 hours after which TLC analysis indicated complete consumption of the Weinreb amide. A saturated aqueous NH$_4$Cl solution and EtOAc were added and the layers were separated. The organic layer was extracted with brine, dried over MgSO$_4$ and concentrated under reduced pressure. The title compound was obtained after column chromatography (20%->50% EtOAc/PE) as a colourless oil (yield: 1.71 g, 3.77 mmol, 94%). $^1$H NMR (400 MHz, CDCl$_3$): δ=7.33-7.24 (m, 5H), 7.11 (d, J=7.87 Hz, 2H), 6.97 (d, J=8.00 Hz, 2H), 6.03 (s, 1H), 5.85 (s, 1H), 5.77 (d, J=8.18 Hz, 1H), 5.30 (dd, J=14.10, 6.11 Hz, 1H), 5.12-5.08 (m, 1H), 5.04 (dd, J=26.54, 12.35 Hz, 2H), 4.21 (d, J=5.41 Hz, 2H), 3.09 (dd, J=13.79, 5.88 Hz, 1H), 2.89 (dd, J=13.76, 5.97 Hz, 1H), 1.84 (s, 3H), 1.44 (s, 9H) ppm. $^{13}$C NMR (100 MHz, CDCl$_3$): δ=199.28, 155.66, 155.34, 141.99, 137.40, 136.13, 134.60, 129.27, 128.17, 127.80, 127.71, 126.50, 79.01, 66.45, 55.13, 43.96, 38.76, 28.14, 17.44 ppm. HRMS: calcd. for C$_{26}$H$_{32}$N$_2$O$_5$ 453.23840 [M+H]$^+$. found 453.23818.

Benzyl ((2S,3R)-1-(4-((tert-butyloxycarbonylamino)methyl)phenyl)-3-hydroxy-4-methylpent-4-en-2-yl)carbamate (13)

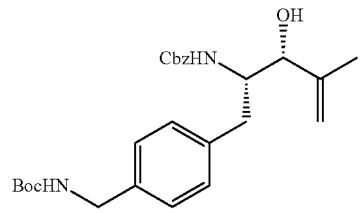 [SMILES: C=C(C)[C@@H](O)[C@H](Cc1ccc(CNC(=O)OC(C)(C)C)cc1)NC(=O)OCc1ccccc1]

Ketone 12 (2.81 g, 4.30 mmol) was dissolved in MeOH (25 mL) and cooled to 0° C. To this were added CeCl$_3$.7H$_2$O (1.5 eq., 6.45 mmol, 2.43 g) and NaBH$_4$ (1.4 eq., 6.0 mmol, 227 mg) portion-wise and the mixture was stirred for 5 minutes. after which TLC analysis indicated a complete conversion. Glacial acetic acid (10 mL) was added and the mixture was concentrated under reduced pressure. The resulting residue was dissolved in EtOAc and extracted with half saturated aq. NaHCO$_3$ (2×) and brine, dried over MgSO$_4$ and concentrated in vacuo. The title compound was obtained as a colourless oil (yield: 1.79 g, 3.94 mmol, 92%). $^1$H NMR (400 MHz, CDCl$_3$): δ=7.31-7.01 (m, 9H), 5.30 (d, J=9.18 Hz, 1H), 5.06 (s, 1H), 5.00 (d, J=5.19 Hz, 1H), 4.96-4.91 (m, 3H), 4.21 (d, J=4.41 Hz, 1H), 4.16-4.11 (m, 1H), 4.07-3.98 (m, 1H), 2.85 (d, J=12.55 Hz, 1H), 2.65 (dd, J=13.60, 10.41 Hz, 1H), 1.77 (s, 3H), 1.44 (s, 9H) ppm. $^{13}$C NMR (100 MHz, CDCl$_3$): δ=155.96, 155.85, 144.44, 137.34, 136.44, 129.34, 128.19, 127.77, 127.66, 127.25, 112.17, 79.25, 76.65, 66.27, 54.06, 44.15, 33.69, 28.22, 18.73 ppm. [α]$_D^{23}$=−18.7 (c=1, CHCl$_3$). HRMS: calcd. for C$_{26}$H$_{34}$N$_2$O$_5$ 455.25405 [M+H]$^+$. found 455.25392.

Benzyl ((S)-3-(4-((tert-butyloxycarbonylamino)methyl)phenyl)-1-((R)-2-methyloxiran-2-yl)-1-oxopropan-2-yl)carbamate (14)

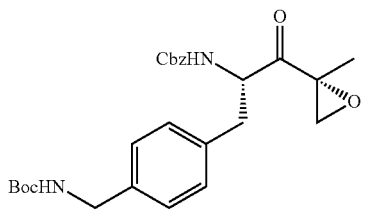 [SMILES: CC(C)(C)OC(=O)NCc1ccc(C[C@H](NC(=O)OCc2ccccc2)C(=O)[C@@]2(C)CO2)cc1]

Allylic alcohol 13 (1.79 g, 3.94 mmol) was dissolved in DCM (25 mL) and cooled to 0° C. after which vanadyl acetylacetonate (0.1 eq., 0.4 mmol, 107 mg) and tBuOOH (3 eq., 12.0 mmol, 2.18 mL; 5.5 M in decane) were added and the mixture was stirred at 0° C. until TLC analysis indicated complete consumption of starting material after 2 hours. The mixture was concentrated under reduced pressure, redissolved in EtOAc and extracted with half sat. aq. NaHCO$_3$, H$_2$O and brine, dried over MgSO$_4$ and concentrated under reduced pressure. The resulting product was quickly purified by column chromatography (20%->60% EtOAc/PE) and immediately subjected to the next step because of the possible instability of the intermediate. The compound was dissolved in DCM (25 mL) and Dess-Martin periodinane (3 eq., 11.0 mmol, 4.50 g) was added. The mixture was stirred at room temperature for 12 hours after which TLC analysis indicated complete conversion. Next, a 1:4 (v/v) mixture (150 mL) of NaHCO$_3$ (sat. aq.)/Na$_2$S$_2$O$_3$ (1 M aq.) and the resulting emulsion was stirred vigorously for 30 minutes after which the layers were separated and the aqueous layer extracted with DCM. The combined organic layers were extracted with sat. aq. NaHCO$_3$, dried over MgSO$_4$ and concentrated under reduced pressure. The title compound was obtained after column chromatography (20%->30% EtOAc/PE) as a colourless oil (yield: 1.03 g, 2.20 mmol, 56%). $^1$H NMR (400 MHz, CDCl$_3$): δ=7.33-7.22 (m, 5H), 7.16 (d, J=7.94 Hz, 2H), 7.08 (d, J=7.95 Hz, 2H), 5.51 (d, J=8.19 Hz, 1H), 5.06-5.01 (m, 1H), 4.97 (d, J=4.39 Hz, 2H), 4.60 (dd, J=12.65, 7.86 Hz, 1H), 4.24 (d, J=4.36 Hz, 2H), 3.26 (d, J=4.62 Hz, 1H), 3.08 (dd, J=13.96, 4.48 Hz, 1H), 2.87 (d, J=4.53 Hz, 1H), 2.70 (dd, J=13.88, 8.12 Hz, 1H), 1.49 (s, 3H), 1.44 (s, 9H) ppm. $^{13}$C NMR (100 MHz, CDCl$_3$): δ=207.77, 155.74, 155.66, 137.61, 135.97, 134.62, 129.32, 128.26, 127.91, 127.76, 127.44, 79.15, 66.62, 58.99, 54.07, 52.12, 44.07, 36.61, 28.21, 16.34 ppm. $[α]_D^{23}$=+82.2 (c=1, CHCl$_3$).

tert-Butyl 4-((S)-2-amino-3-((R)-2-methyloxiran-2-yl)-3-oxopropyl)benzylcarbamate TFA salt (15)

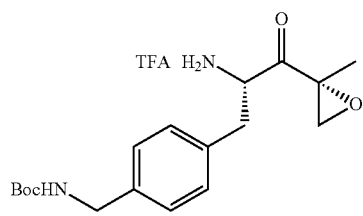 [SMILES: CC(C)(C)OC(=O)NCc1ccc(C[C@H](N)C(=O)[C@@]2(C)CO2)cc1 ; "TFA"]

Cbz-protected amine 14 (107 mg, 0.23 mmol) was dissolved in MeOH (5 mL) and to this was added TFA (1.2 eq., 0.27 mmol, 21 µL). Argon was bubbled through the solution for 15 minutes, after which Pd black (10 mg) was added and the flask was charged with hydrogen gas. After 10 minutes, TLC analysis indicated complete conversion of starting material and all solids were removed by filtration over CELITE. Toluene (10 mL) was added and the mixture was concentrated under reduced pressure followed by coevaporation with toluene (2×) in order to remove excess TFA. The purity of the deprotected amine (as TFA salt) was confirmed by LC-MS analysis and the compound was subjected to the next step without further purification.

(S)-tert-butyl 4-(3-(methoxy(methyl)amino)-3-oxo-2-(tritylamino)propyl)benzylcarbamate (16)

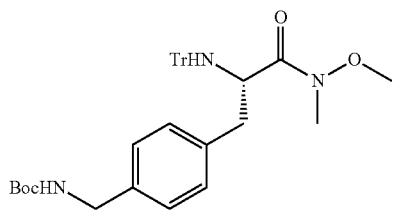

Compound II (1.43 g, 3.04 mmol) was dissolved in a 50:1 mixture EtOH/AcOH (25 mL) and argon was bubbled through this solution for 15 minutes. Next, Pd/C (10% w/w, 0.1 g) was added and hydrogen was bubbled through the mixture until TLC indicated complete consumption of starting material after 4 hours. Argon was bubbled through for another 15 minutes after which the mixture was filtered over CELITE and the filtrate concentrated under reduced pressure. The deprotected amine (as AcOH salt) was obtained in a crude yield of 1.21 g (max. 3.04 mmol) and was subsequently dissolved in DCM (20 mL). To this were added Et$_3$N (2 eq., 6.08 mmol, 0.85 mL), DMAP (0.1 g) and tritylchloride (1.5 eq., 4.56 mmol, 1.30 g). The mixture was stirred for 6 hours after which it was concentrated under reduced pressure, redissolved in EtOAc and extracted with 10 mM aq. HCl and brine, dried over MgSO$_4$ and concentrated under reduced pressure. The resulting mixture was purified by column chromatography (10%->50% EtOAc/PE) and the title compound was obtained as colourless foam (yield: 0.68 g, 1.17 mmol, 38%). $^1$H NMR (400 MHz, CDCl$_3$): δ=7.47 (s, 1H), 7.34 (d, J=7.33 Hz, 6H), 7.26-7.20 (m, 4H), 7.18-7.05 (m, 9H), 5.10 (s, 1H), 4.28 (s, 2H), 4.00 (t, J=5.60, 5.60 Hz, 1H), 3.18 (s, 3H), 2.92 (dd, J=13.24, 5.63 Hz, 1H), 2.77 (dd, J=12.93, 7.51 Hz, 1H), 2.63 (s, 3H), 1.44 (s, 9H) ppm. $^{13}$C NMR (100 MHz, CDCl$_3$): δ=174.80, 155.74, 145.92, 137.18, 137.13, 130.25, 128.70, 127.33, 127.15, 125.86, 79.07, 70.59, 60.00, 54.09, 44.19, 41.86, 31.96, 28.20 ppm. $[α]_D^{23}$=+58.6 (c=1, CHCl$_3$).

(S,E)-tert-butyl 4-(4-(methylsulfonyl)-2-(tritylamino)but-3-en-1-yl)benzylcarbamate (17)

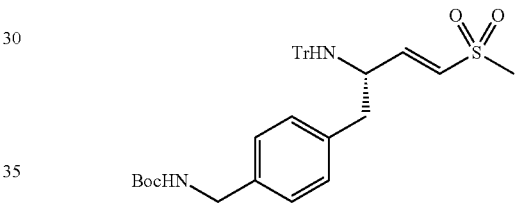

Weinreb amide 16 (0.65 g, 1.12 mmol) was dissolved in Et$_2$O (15 mL), put under an argon atmosphere and cooled to 0° C. LiAlH$_4$ (2 eq., 2.25 mmol, 0.56 mL of a 4 M solution in Et$_2$O) was added slowly and the mixture was stirred at 0° C. for 1 hour after which TLC analysis indicated complete conversion of the starting compound. 0.1 M aq. HCl (15 mL) was slowly added and the layers were separated. The organic layer was extracted with 0.1 M aq. HCl and brine, dried over MgSO$_4$ and concentrated under reduced pressure. Diethyl ((methylsulfonyl)methyl)phosphonate (1.5 eq., 1.68 mmol, 0.39 g) was dissolved in THF (20 mL) and cooled to 0° C. under an argon atmosphere. NaH (1.5 eq., 1.68 mmol, 67.2 mg, 60% w/w in mineral oil) was slowly added and the mixture was stirred at 0° C. for 30 minutes. Next, the freshly obtained aldehyde (in THF (2 mL)) was slowly added and the mixture was stirred for 2 hours while slowly warming it to room temperature. After this time TLC analysis indicated complete conversion of the aldehyde. EtOAc (20 mL) was added and the mixture was extracted with mM aq. HCl (2×) and brine, dried over MgSO$_4$ and concentrated under reduced pressure. The title compound was obtained after column chromatography (20%->50% EtOAc/PE) as a colourless foam (yield: 0.57 g, 0.95 mmol, 85%). $^1$H NMR (400 MHz, CDCl$_3$): δ=7.46 (d, J=7.6 Hz, 6H), 7.28 (t, J=7.20, 6.80 Hz, 6H), 7.20 (t, J=7.20, 7.20 Hz, 3H), 7.13 (d, J=7.60 Hz, 2H), 6.87 (d, J=8.00 Hz, 2H), 6.57 (dd, J=14.80, 7.00 Hz, 1H), 5.96 (d, J=14.80 Hz, 1H), 4.80 (s, 1H), 4.24 (d, J=5.60 Hz, 2H), 3.49 (q, J=6.00 Hz, 1H), 2.61 (s, 3H), 2.54 (dd, J=13.20, 5.20 Hz, 1H), 2.33 (dd, J=13.20, 8.20 Hz, 1H), 1.44 (s, 9H) ppm. $^{13}$C NMR (100 MHz, CDCl$_3$): δ=155.59, 150.21, 145.74, 137.42, 135.28, 129.53, 128.35, 128.02, 127.70, 127.14, 126.44, 78.91, 71.05, 55.33, 43.79, 42.43, 41.86, 28.09 ppm.

$[\alpha]_D^{23}$=−21.3 (c=1, CHCl$_3$). HRMS: calcd. for C$_{36}$H$_{40}$N$_2$O$_4$S 619.26010 [M+Na]$^+$. found 619.26001.

(S,E)-tert-butyl 4-(4-(methylsulfonyl)-2-aminobut-3-en-1-yl)benzylcarbamate (18)

Trityl protected amine 17 (0.54 g, 0.90 mmol) was treated with 1% v/v TFA/DCM (15 mL) at room temperature. To this yellow solution was added H$_2$O (1 mL) which resulted in a colourless suspension. After stirring the mixture for 30 minutes, 10 mM aq. HCl (20 mL) was added and DCM was removed under reduced pressure. The aqueous layer was extracted with Et$_2$O (3×) and basified with NaHCO$_3$ until pH 9, after which it was extracted with DCM (3×). The latter combined organic layers were dried over MgSO$_4$ and concentrated under reduced pressure. The resulting deprotected amine proved to be pure on LC-MS analysis and was subjected to the next step without further purification.

N$_3$Phe-Leu-Leu-Phe (4-CH$_2$NH$_2$) VS (SEQ ID NO: 4) TFA salt (4a)

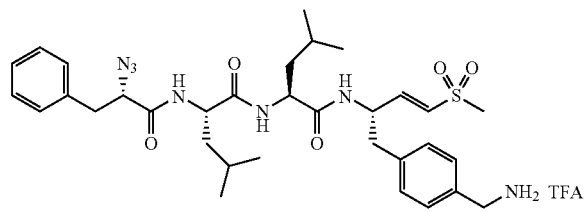 [SMILES: CC(C)C[C@H](NC(=O)[C@H](Cc1ccccc1)N=[N+]=[N-])C(=O)N[C@@H](CC(C)C)C(=O)N[C@H](/C=C/S(C)(=O)=O)Cc1ccc(CN)cc1]

This compound was synthesized according to General procedure I on a 100 μmol scale by addition of amine 18. The title compound was obtained after RP-HPLC purification (gradient: 20%->60% MeOH/0.1% aq. TFA) as a colourless solid (yield: 15.4 mg, 20.1 mmol, 20%). $^1$H NMR (400 MHz, CD$_3$OD): δ=7.39-7.21 (m, 9H), 6.78 (dd, J=15.20, 5.34 Hz, 1H), 6.55 (dd, J=15.21, 1.52 Hz, 1H), 4.82-4.77 (m, 1H), 4.36-4.27 (m, 2H), 4.17 (dd, J=8.61, 4.80 Hz, 1H), 4.07 (s, 2H), 3.19 (dd, J=14.05, 4.75 Hz, 1H), 3.02-2.95 (m, 3H), 2.92 (s, 3H), 1.63-1.43 (m, 6H), 0.93 (t, J=5.65, 5.65 Hz, 6H), 0.88 (d, J=6.24 Hz, 6H) ppm. $^{13}$C NMR (100 MHz, CD$_3$OD): δ=174.45, 174.27, 171.95, 146.65, 139.63, 137.85, 133.01, 131.90, 131.30, 130.47, 130.26, 129.67, 128.13, 65.56, 53.74, 53.49, 52.46, 44.11, 42.83, 41.80, 41.61, 40.29, 38.71, 25.95, 25.86, 23.47, 23.46, 21.96, 21.94 ppm. LC-MS: R$_t$ (min): 6.99 (ESI-MS (m/z): 654.20 (M+H$^+$)). HRMS: calcd. for C$_{33}$H$_{17}$N$_7$O$_5$S 654.34321 [M+H]$^+$. found 654.34322.

N$_3$Phe-Leu-Leu-Phe(4-CH$_2$NH$_2$)EK (SEQ ID NO:5) TFA salt (4b)

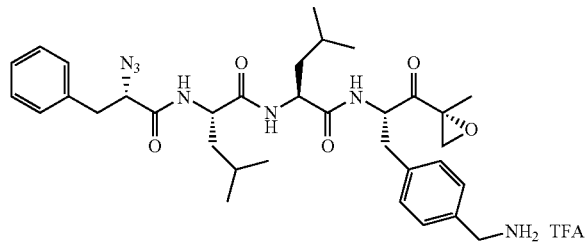 [SMILES: CC(C)C[C@H](NC(=O)[C@H](Cc1ccccc1)N=[N+]=[N-])C(=O)N[C@@H](CC(C)C)C(=O)N[C@@H](Cc1ccc(CN)cc1)C(=O)[C@@]1(C)CO1]

This compound was synthesized according to General procedure I on a 100 μmol scale by addition of amine 15. The title compound was obtained after RP-HPLC purification (gradient: 20%->60% MeOH/0.1% aq. TFA) as a colourless solid (yield: 17.6 mg, 23.5 μmol, 24%). $^1$H NMR (400 MHz, CD$_3$OD): δ=7.36-7.20 (m, 9H), 4.68 (dd, J=9.34, 4.20 Hz, 1H), 4.38-4.28 (m, 2H), 4.12 (dd, J=8.58, 4.79 Hz, 1H), 4.05 (s, 2H), 3.21 (d, J=4.97 Hz, 1H), 3.15 (dd, J=14.18, 4.69 Hz, 1H), 3.08 (dd, J=13.84, 4.06 Hz, 1H), 2.95-2.87 (m, 2H), 2.72 (dd, J=13.90, 9.34 Hz, 1H), 1.52-1.43 (m, 6H), 1.41 (s, 3H), 0.94-0.83 (m, 12H) ppm. $^{13}$C NMR (100 MHz, CD$_3$OD): δ=208.54, 174.48, 174.13, 171.69, 139.71, 137.87, 132.95, 131.15, 130.47, 130.14, 129.65, 128.10, 65.59, 60.25, 54.51, 53.40, 53.15, 52.79, 44.14, 42.13, 41.79, 38.73, 37.11, 25.83, 23.49, 22.03, 21.94, 16.81 ppm. LC-MS: R$_t$ (min): 7.36 (ESI-MS (m/z): 634.20 (M+H$^+$)). HRMS: calcd. for C$_{34}$H$_{47}$N$_7$O$_5$ 634.37114 [M+H]$^+$. found 634.37090.

(Val-Ser-Phe (4-CH$_2$NH$_2$)-methyl vinyl sulfone)-3-hydroxy-2-methylbenzamide (40)

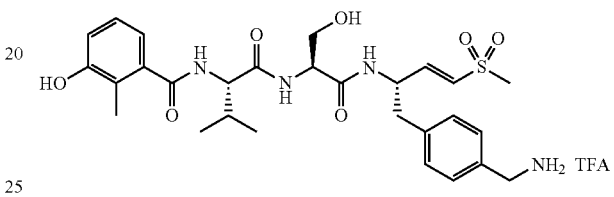

This compound was synthesized according to General procedure I on a 245 μmol scale by addition of amine 18. The title compound was obtained after RP-HPLC purification (gradient: 10%->25% ACN/0.1% aq. TFA) as a colorless solid (yield: 57.3 mg, 83.2 μmol, 34%). $^1$H NMR (400 MHz, CD$_3$OD): δ=7.22 (d, J=8.48 Hz, 2H), 7.19 (d, J=8.45 Hz, 2H), 6.95 (t, J=7.80 Hz, 1H), 6.77-6.69 (m, 3H), 6.65 (dd, J=15.17, 1.46 Hz, 1H), 4.81-4.76 (m, 1H), 4.29 (t, J=5.53 Hz, 1H), 4.17 (d, J=7.16 Hz, 1H), 3.90 (d, J=5.45 Hz, 2H), 3.69 (dd, J=10.78, 5.01 Hz, 1H), 3.60 (dd, J=10.76, 6.19 Hz, 1H), 2.92 (dd, J=13.83, 6.47 Hz, 1H), 2.84-2.80 (m, 1H), 2.82 (s, 3H), 2.10-2.01 (m, 1H), 2.06 (s, 3H), 0.89 (dd, J=6.67, 4.95 Hz, 6H) ppm. $^{13}$C NMR (100 MHz, CD$_3$OD): δ=174.00, 173.61, 171.83, 157.08, 146.95, 139.62, 139.11, 132.93, 131.78, 131.18, 130.18, 127.60, 123.26, 119.16, 117.19, 62.90, 61.62, 56.49, 52.60, 44.04, 42.84, 40.16, 31.40, 19.89, 19.06, 13.06 ppm. LC-MS: R$_t$ (min): 4.19 (ESI-MS (m/z): 575.20 (M+H$^+$)). HRMS: calcd. for C$_{28}$H$_{38}$N$_4$O$_7$S [M+H]$^+$ 575.25340. found 575.25336.

Biological Evaluation: Competition Assays in Cell Lysate.

Whole cell lysates of HEK-293T or EL-4 cells were made by sonication in 3 volumes of lysis buffer containing 50 mM Tris pH 7.5, 1 mM DTT, 5 mM MgCl$_2$, 250 mM sucrose, 2 mM ATP, 0.025% digitonin. Protein concentration was determined by the Bradford assay. Cell lysates (13.5 μg total protein for HEK lysates and 9 μg total protein for EL-4 lysates) were exposed to the inhibitors for 1 hour at 37° C. prior to incubation with MV151 (0.5 μM) or BODIPY-TMR-epoxomicin (0.5 μM) for an additional 1 hour at 37° C. Reaction mixtures were boiled with Laemmli's buffer containing β-mercaptoethanol for 5 minutes before being resolved by 12.5% SDS-PAGE. In-gel detection of residual proteasome activity was performed in the wet gel slabs directly on the TYPHOON Variable Mode Imager (Amersham Biosciences) using the Cy3/Tamra settings ($\lambda_{ex}$ 532 nm, $\lambda_{em}$ 560 nm) to detect MV151, BODIPY-TMR-epoxomicin and Cy2/Fam settings ($\lambda_{ex}$ 488 nm, $\lambda_{em}$ 520 nm) to detect compounds 39 and 59.

Biological Evaluation: Competition Assays in Living Cells.

Human embryonic kidney cells (some 1×10$^6$) were cultured in 6-well plates in DMEM containing 10% fetal calf serum, 10 units/mL penicillin and 10 μg/mL streptomycin in a 7% $CO_2$ humidified incubator at 37° C. overnight. Part of the medium was taken and to this was added the appropriate inhibitor in DMSO (1 μL of a 1,000× stock solution), after which the medium was added to the cells. The cells were incubated with the inhibitors for 4 hours at 37° C. and this was followed by addition of MV151 (1 μL of a 5 mM stock solution in DMSO) and incubation for 2 hours at 37° C. Next, the medium was removed and the cells were washed with PBS and harvested. After flash freezing in liquid $N_2$, the cells were resuspended in 4 volumes of homogenation buffer (50 mM Tris pH 7.5, 250 mM sucrose, 5 mM $MgCl_2$, 1 mM DTT, 2 mM ATP, 0.025% digitonin) containing 10 μM AdaKBio, sonicated (12 W, 1 minute) and centrifuged at 16,000 rcf at 0° C. for 20 minutes. The supernatant was collected and the protein concentration was determined by the Bradford assay. All samples were normalized to the same protein concentration with lysis buffer. After boiling the samples with Laemmli's buffer containing p-mercaptoethanol for 5 minutes and resolving by 12.5% SDS-PAGE the residual proteasome activity was detected as described above.

Example 10

Evaluation of Epoxyketones and Vinyl Sulfones with 4-Aminomethylene-L-Phenylalanine in the P1 Position Retro-synthetically, the modified oligopeptides can be prepared from tripeptide hydrazide $N_3$Phe-Leu-Leu-NHNH$_2$ and the properly protected warhead amines in an (epimerization free) azide coupling. The synthesis of P1-benzyl amine containing vinyl sulfone and epoxyketone warheads leading to inhibitors 4a and 4b is shown in Scheme 3. The synthetic scheme commenced with the introduction of the aminomethylene substituent on L-phenylalanine 8, by performing an electrophilic aromatic substitution with N-(hydroxymethyl) trichloroacetamide under acidic conditions. In this reaction both the ortho and the para substituted isomers were formed, which could be separated by column chromatography. The desired para substituted isomer was obtained in 35% yield. After Cbz-protection of the α-amine, compound 9 was obtained. Basic removal of the trichloroacetamide group followed by Boc protection of the formed amine gave 10, which was coupled to N,O-dimethylhydroxylamine to give Weinreb-amide 11. Upon a reaction with 2-lithiumpropene the α',β'-unsaturated ketone 12 was obtained. Stereoselective reduction to the allylic alcohol 13 and subsequent asymmetric epoxidation and Dess-Martin oxidation resulted in epoxyketone 14. This compound was α-amine deprotected by hydrogenation, which finalized the synthesis of compound 15. The vinylsulfone analogue was created by α-amine deprotection of compound II, followed by tritylation (16). Reduction of the Weinreb-amide, followed by a Horner-Wadworth-Emmons reaction and de-tritylation finally resulted in compound 18.

SCHEME 3

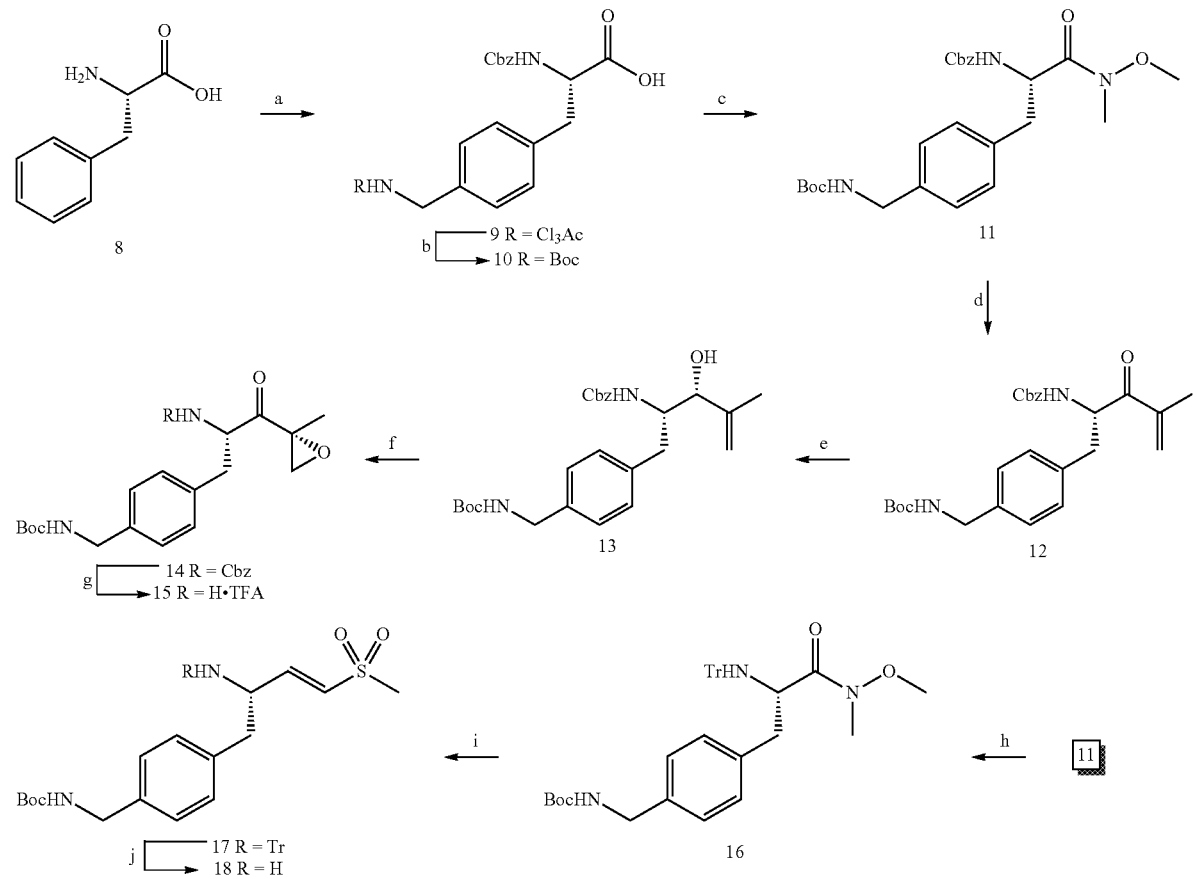

Reagents and conditions in Scheme 3 are as follows: (a) i) N-(hydroxymethyl)trichloroacetamide, H$_2$SO$_4$, H$_2$O; ii) benzyl chloroformate, Na$_2$CO$_3$, H$_2$O, 1,4-dioxane, 35%; (b) i) 20% NaOH, EtOH/H$_2$O 1:1; ii) Boc$_2$O, Na$_2$CO$_3$, THF, H$_2$O, 75%; (c) NH(Me)OMe.HCl, HCTU, DiPEA, DCM, 98%; (d) 2-bromopropene, tBuLi, THF, −78° C., 94%; (e) NaBH$_4$, CeCl$_3$.7H$_2$O, MeOH, 0° C., 92%; (f) i) tBuOOH, VO(Acac)$_2$, DCM, 0° C.; ii) Dess-Martin periodinane, DCM, 56%; (g) H$_2$, Pd black, TFA, MeOH; (h) i) H$_2$, Pd/C, AcOH, EtOH; ii) TrCl, Et$_3$N, DMAP, DCM, 38%; (i) i) LiAlH$_4$, Et$_2$O, 0° C.; ii) diethyl ((methylsulfonyl)methyl)phosphonate, NaH, THF, 0° C., 85%; (j) 1% TFA/DCM.

Scheme 4 shows the azide coupling of amine warheads 18 and 24 with tripeptide hydrazide 38, giving, after TFA-mediated deprotection and RP-HPLC purification, inhibitor 4a. The other inhibitors were made in a similar reaction from the appropriate amines in varying yields of 7-48% after RP-HPLC. LC-MS and NMR analysis showed for neither compound any sign of epimerization of the final products.

SCHEME 4

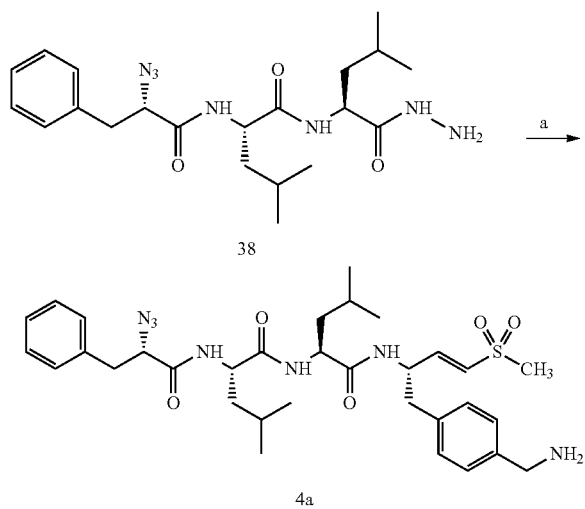

Reagents and conditions in Scheme 4 are as follows: (a) i) tBuONO, HCl, DMF, DCM, −30° C.; ii) compound 18 or 24, DiPEA; iii) TFA, DCM, then RP-HPLC, yields: 7-48%.

The inhibition potential of the inhibitors for each of the catalytically active subunits was assessed in competition assays employing extracts of human embryonic kidney cells (HEK-293T) and mouse lymphoma cells (EL-4) in combination with the fluorescent broad spectrum proteasome probe MV151 (Verdoes, et al. (2006) Chem. Biol. 13:1217-1226). Competitive inhibition of a proteasome active site is reflected by the disappearance of the corresponding band on a gel.

Compound 4a was tested for their capability to cross the cell membrane. Living HEK-293T cells were incubated with each of the three inhibitors at 0.5, 5 and 50 µM final concentrations for 4 hours, after which all residual proteasome activity was labelled with cell permeable probe MV151. The cells were lysed, all proteins denatured and resolved by SDS-PAGE. As a control the broad-spectrum proteasome inhibitor AdaAhx$_3$L$_3$VS (Kessler, et al. (2001) Chem. Biol. 8:913-929), which is known to be able to cross the cell membrane, was used. The results indicated that the primary amine in compound 4a does not result in inpermeability toward the cell membrane and is still able of inhibiting (almost) all β2 activity at 5 µM.

For direct labeling of β2, a new fluorescent probe was made by reacting compound 4a with a green fluorescent BODIPY-alkyne (Verdoes, et al. (2007) Bioorg. Med. Chem. Lett. 17:6169-6171) in a 'click' reaction. This reaction however was not as straightforward as could be expected from earlier results. Upon reaction of both compounds with CuSO$_4$ and sodium ascorbate in an aqueous medium, compound 4a was completely consumed, however the formed product had a mass of one Dalton less compared to the expected product mass and it was dramatically more hydrophobic compared to the starting material, as evidenced from LC-MS measurements. It was reasoned that the free benzylic amine was oxidized and hydrolyzed into its corresponding benzaldehyde. This reaction has been previously observed (Srogl & Voltrova (2009) Org. Lett. 11:843-845), wherein a copper/ascorbic acid dyad catalytic system for the selective aerobic oxidation of amines (both benzylic and aliphatic). Indeed, upon addition of ammonium acetate and NaCNBH$_3$ a reductive amination took place, resulting in the desired product 39.

The ability of compound 39 to label proteasome actives both in HEK-293T cell lysate and living cells was assessed in a competition assay as described herein. A dual-wavelength fluorescence read-out was performed allowing visualisation of one of the two fluorescent dyes at a time. From this analysis it becomes clear that the introduction of the bulky, hydrophobic BODIPY moiety results in the loss of the inhibitor's selectivity for β2 over β5. Both subunits are inhibited equally well, leaving only β1 untouched. It is likely that the large hydrophobic moiety is too close to the active site and introduction of a spacer between tag and warhead may reinstall β2 selectivity. Interestingly, introduction of the BODIPY had a detrimental effect on cell permeability. At a concentration of 5 µM, both subunits (β2 and β5) seemed not to be competed away at all, although a faint band for each subunit was visible in the lower gel. Even at a concentration of 50 µM, not all proteasome activity was silenced. This observation likely comes from the cell penetrating properties of the probe, since all β2 and β5 proteasomal activity was inhibited at a 5 µM concentration in cell lysate.

As discussed, vinyl ethyl ester tripeptide HMB-VSL-VE 2 has been identified as a potent, cell permeable β2 selective inhibitor (Marastoni, et al. (2005) J. Med. Chem. 48:5038-5042; Baldisserotto, et al. (2007) Eur. J. Med. Chem. 42:586-592). Other inhibitors containing the vinyl ethyl ester warhead have been made, which are known to target other subunits as well (Baldisserotto, et al. (2009) Bioorg. Med. Chem. 17:5535-5540). It is therefore likely that the majority of the β2 selectivity comes from the unique HMB-Val-Ser peptide sequence. For this reason, a combination of the HMB-Val-Ser peptide sequence and the P1-functionalized warheads discussed so far may result in inhibitors with an even enhanced preference for the β2i subunit. To this end compounds 40 and 41 were synthesized via the method outlined above from HMB-Val-Ser(tBu)-NHNH$_2$. First, both compounds were tested for their inhibitory activity in HEK-293T cell lysate in a competition assay as discussed earlier. When comparing compound 40 and 4a, it became clear that substitution of the N$_3$PheLeu$_2$ for the HMB-Val-Ser motif decreased the general potency by a factor two. In addition, the selectivity for β2 over β5 was substantially increased. Only a part of the β5 activity was inhibited at 50 µM by 40, whereas compounds 4a completely blocked β5 at this concentration. This difference was even more pronounced for the inhibition in living cells by 40. The β2 band had almost disappeared at a concentration of 5 µM and β5 was not affected at all at concentrations up to 50 µM. The most striking result from this assay was the apparent selectivity of compound 40 for β2 over β2i in EL-4 lysate. At a concentration of 0.5 µM, β2 was almost completely blocked, whereas the compound started to inhibit β2i only at 5 µM. The characteristics in terms of selectivity remained unchanged (it still targeted both β2 and β5). These observations indicate that the HMB-Val-Ser sequence on its own is not enough to provide β2 selectivity.

Example 11

PR-671A Overcomes Bortezomib Resistance

The activity of compound 4a (as referred to as PR671A or LU-102) was further tested in combination with β5-selective proteasome inhibitors, bortezomib or PR523 (i.e., LU-005). Using myeloma cells, U266 and AMO-1, it was found that the combination of PR671A and either bortezomib or PR523 resulted in synergistic cytotoxicity against the myeloma cells (FIG. 1A-1D).

Figure 2A:
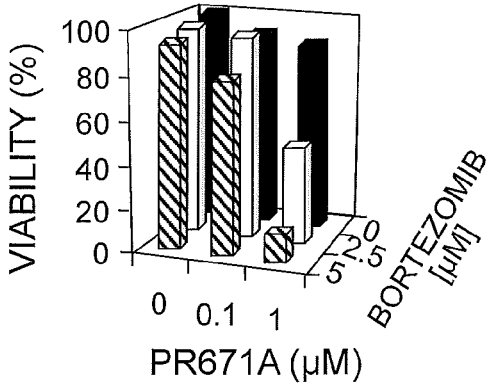
FIG. 2 shows that compound 4a (PR671A) in combination with 135-selective proteasome inhibitors, bortezomib (FIGS. 2A and 2C) or PR523 (i.e., LU-005.
FIGS. 2B and 2D) overcomes bortezomib resistance in bortezomib-adapted myeloma cell lines, AMO-1a (FIGS. 2A and 2B) and HL-60a (FIGS. 2C and 2D), and bortezomib-refractory primary myeloma cells from three different patients (FIGS. 2E-2G).
Figure 2C:
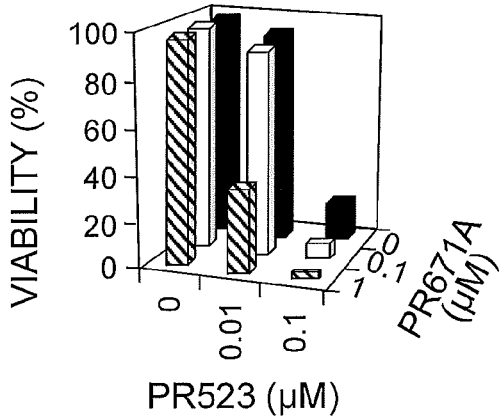
Figure 2B:
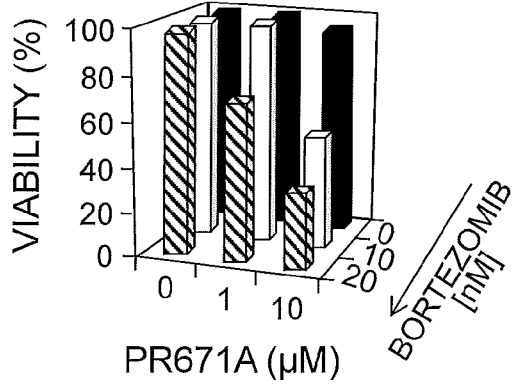
Figure 2D:
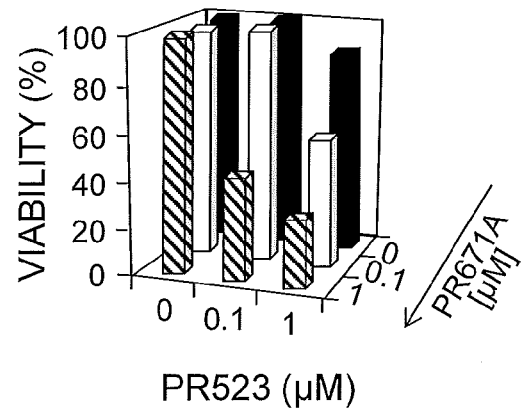
Figure 2E:
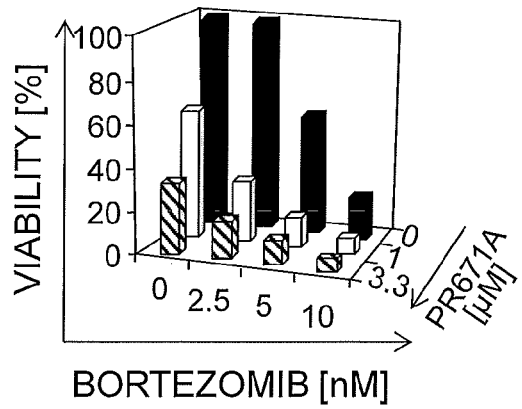
Figure 2F:
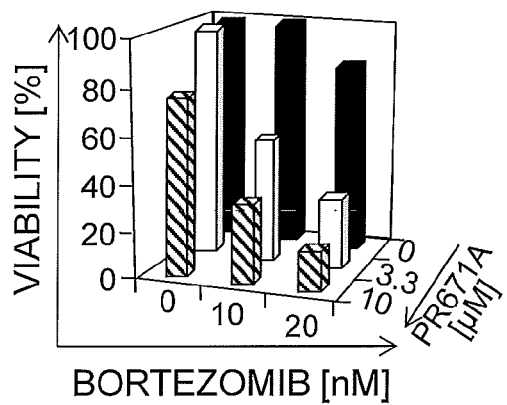
Figure 2G:
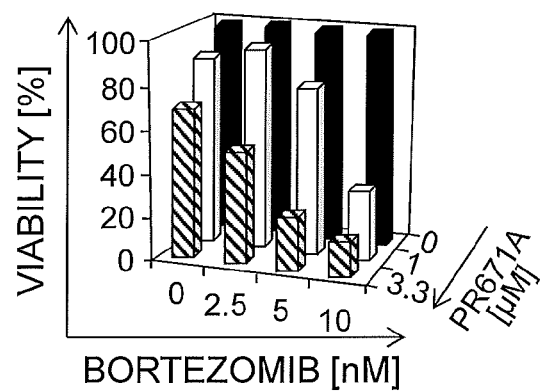

Furthermore, compound 4a (PR671A) in combination with β5-selective proteasome inhibitors, bortezomib (FIGS. 2A and 2C) or PR523 (i.e., LU-005; FIGS. 2B and 2D) was shown to overcomes bortezomib resistance in bortezomib-adapted myeloma cell lines, AMO-1a (FIGS. 2A and 2B) and HL-60a (FIGS. 2C and 2D), and bortezomib-refractory primary myeloma cells from three different myeloma patients exhibiting resistance to bortezomib (FIGS. 2E-2G).

Example 12

Incorporation of Non-Natural Amino Acids Improves Cell Permeability and Potency of Specific Inhibitors of Proteasome Trypsin-Like Sites Design, Synthesis and Initial Characterization of Inhibitors.

As described herein, compounds NC-002, NC-012, NC-022, and az-NC-002 are N-terminally capped epoxyketones with an arginine in the P1 position. The guanido group of the arginine side chain may perform a nucleophilic attack on the epoxyketone electrophile, leading to cyclization and inactivation of the inhibitor. To improve the chemical stability of these inhibitors, the guanidine was replaced with other functional groups, such as para-substituted phenylalanine derivatives because these derivatives would not cyclize. Using these substitutions, the influence of basicity and length of the side chain on the activity of the inhibitor could also be analyzed. In this analysis, benzylamino (pKa=9.3), pyridiyl-(pKa=5.2), and aniline-(pKa=4.6) were used as arginine mimics for the P1 side chain (Table 5).

TABLE 5

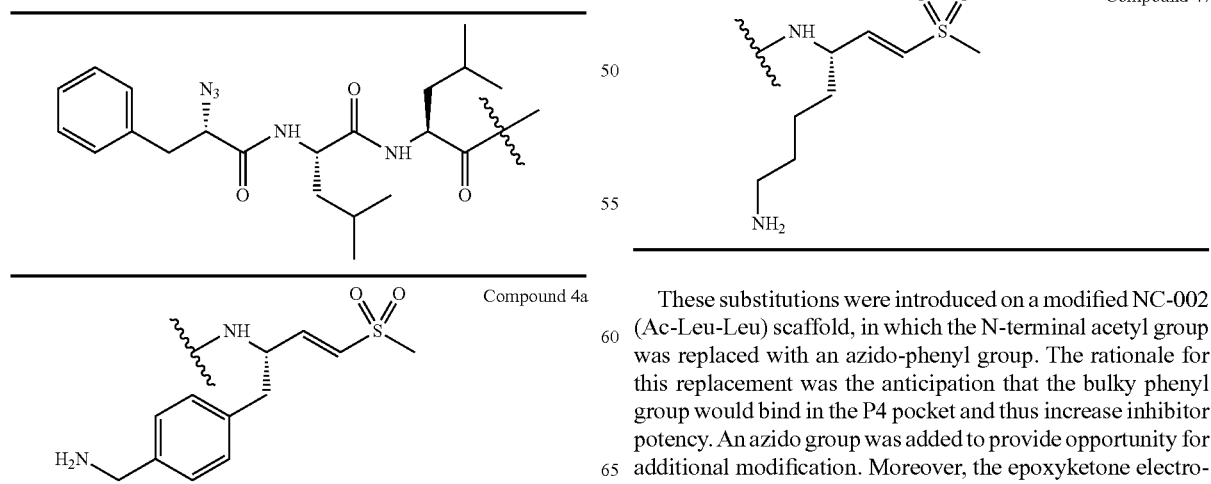

These substitutions were introduced on a modified NC-002 (Ac-Leu-Leu) scaffold, in which the N-terminal acetyl group was replaced with an azido-phenyl group. The rationale for this replacement was the anticipation that the bulky phenyl group would bind in the P4 pocket and thus increase inhibitor potency. An azido group was added to provide opportunity for additional modification. Moreover, the epoxyketone electrophile was replaced with a vinyl sulfone to determine if specificity of inhibitors could be increased.

The initial evaluation of compounds was performed on extracts from HEK293 cells and purified 26S proteasomes from rabbit muscles (Table 6).

TABLE 6

| Cmpd | P1- Electrophile | IC$_{50}$ (μM) for sites in 26S proteasomes: | | | IC$_{50}$ (Chym-L)/ IC$_{50}$ (Tr-L) |
|---|---|---|---|---|---|
| | | Tr-L | Chym-L | Casp-L | |
| 4a | Benzylamino-vs | 0.0038 | 1.7 | 16 | 447 |
| 4b | Benzylamino-ek | 0.25 | 2.7 | 11 | 10.8 |
| 45a | Anilino-vs | 0.11 | 0.04 | 23 | 0.36 |
| 45b | Anilino-ek | 1.8 | 0.01 | >30 | 0.0056 |
| 46 | Pyridino-vs | 0.42 | <0.1 | >>30 | <0.23 |
| 47 | Lys-vs | 0.74 | 22 | >>30 | 30 |
| NC-002 | Arg-ek | 1 | >30 | >>30 | >30 |

>>30, no inhibition at 30 μM; >30, inhibition between 10 and 50% at 30 μM.

Two trends emerged from these experiments. First, vinyl sulfones were more potent and more trypsin-like site-selective inhibitors than epoxyketones with the same peptide sequence (e.g., compare compounds 4a and 4b, 45a and 45b).

Second, potency and specificity for the trypsin-like sites decreased from benzylamine to aniline to pyridine side chain. The vinyl sulfone with benzylamine side chain in the P1 position (compound 4a) was the most potent and specific inhibitor of trypsin-like sites. Compound 45a (anilino-vs) was an equipotent inhibitor of trypsin-like and capsize-like sites, and anilino-ek (45b) and pyridino-vs (46) residues in the P1 position generated inhibitors of the chymotrypsin-like sites. Notably, compound 4a was more potent than any of the first-generation compounds or a vinyl sulfone with a natural lysine side chain in the P1 (compound 47).

Because vinyl sulfones were more potent and specific than epoxyketones, all other inhibitors were synthesized using a vinyl sulfone as warhead. Given that NC-022 is a more potent inhibitor of trypsin-like sites than NC-002, compound 48, with the NC-022 scaffold, benzylamine as P1 substituent and vinyl sulfone as the warhead was prepared. Although compound 48 was more potent than NC-022 (Table 7), it was less potent than compound 4a. Replacing benzylamino with aniline side chain in the P1 position (compound 49) generated an inhibitor of the chymotrypsin-like site (Table 7).

TABLE 7

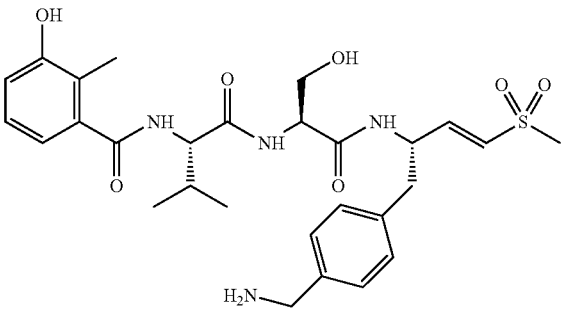 [SMILES: Cc1c(O)cccc1C(=O)N[C@H](C(=O)N[C@@H](CO)C(=O)N[C@H](/C=C/S(C)(=O)=O)Cc1ccc(CN)cc1)C(C)C]

48

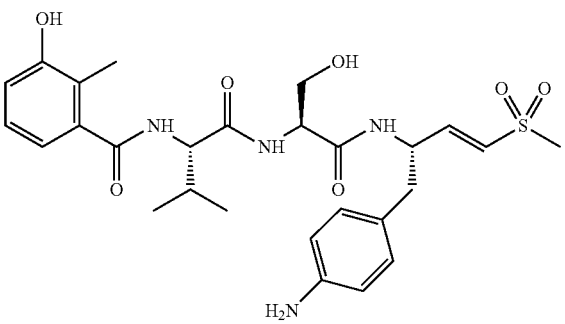 [SMILES: Cc1c(O)cccc1C(=O)N[C@H](C(=O)N[C@@H](CO)C(=O)N[C@H](/C=C/S(C)(=O)=O)Cc1ccc(N)cc1)C(C)C]

49

| Cmpd | IC$_{50}$ (μM) for sites in 26S proteasomes: | | | IC$_{50}$ (Chym-L)/ IC$_{50}$ (Tr-L) |
|---|---|---|---|---|
| | Tr-L | Chym-L | Casp-L | |
| NC-022 | 0.0038 | 1.7 | 16 | 447 |
| 48 | 0.25 | 2.7 | 11 | 10.8 |
| 49 | 0.11 | 0.04 | 23 | 0.36 |

>>30, no inhibition at 30 μM;
>30, inhibition between 10 and 50% at 30 μM.

It has been demonstrated that basic residues in the P1 and P3 positions are important elements of specific inhibitors of the trypsin-like sites (Groll, et al. (2002) *Chem. Biol.* 9:655-62). In this respect, it was found that the most potent inhibitor (NC-012) has basic (Arg) residues in the P1 and P3 positions. Therefore, the aliphatic side chain in the P3 position was replaced with pyridyl (50), aniline (51), and benzylamine (52) side chains (Table 8).

TABLE 8

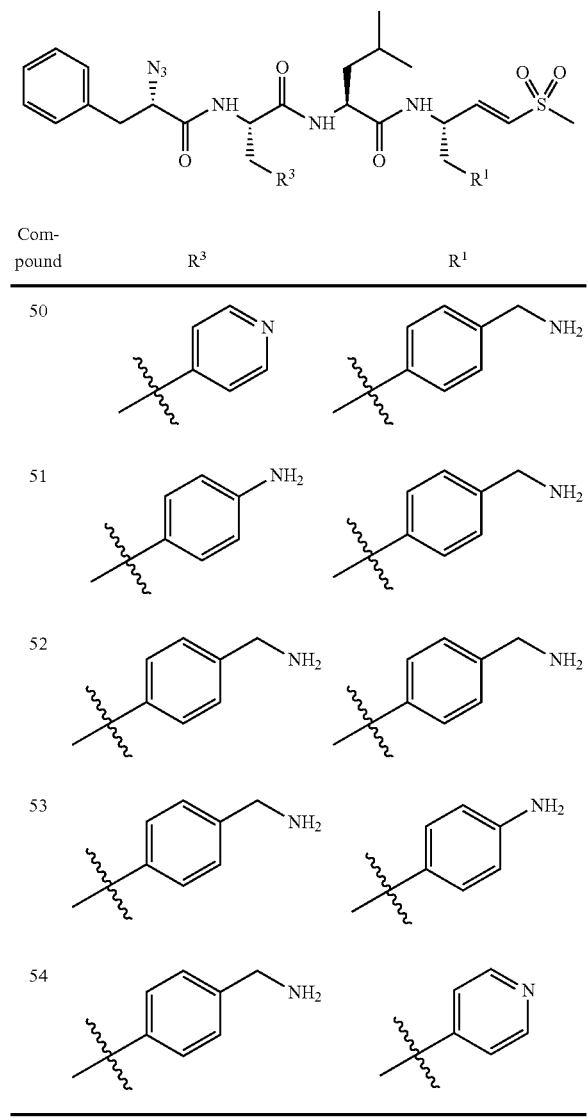

TABLE 9

| Cmpd | IC$_{50}$ (µM) for sites: | | | IC$_{50}$ (Chym-L)/ IC$_{50}$ (Tr-L) |
| --- | --- | --- | --- | --- |
| | Tr-L | Chym-L | Casp-L | |
| 4a | 0.0038 | 1.7 | 16 | 447 |
| 50 | 0.012 | 1.05 | 30 | 87.5 |
| 51 | 0.030 | 3.4 | 30 | 113 |
| 52 | 0.0066 | 3.9 | 18 | 1348 |
| 53 | 0.0063 | 0.19 | >>30 | 59 |
| 54 | 0.045 | 0.41 | >30 | 9.1 |

>>30, no inhibition at 30 µM; >30, inhibition between 10 and 50% at 30 µM.

To complete the structure-activity relationship studies, the effects of replacing basic P1 residues with leucine in the P1 position were analyzed using para-substituted phenylalanines in the P3 as scaffold (Table 10).

TABLE 10

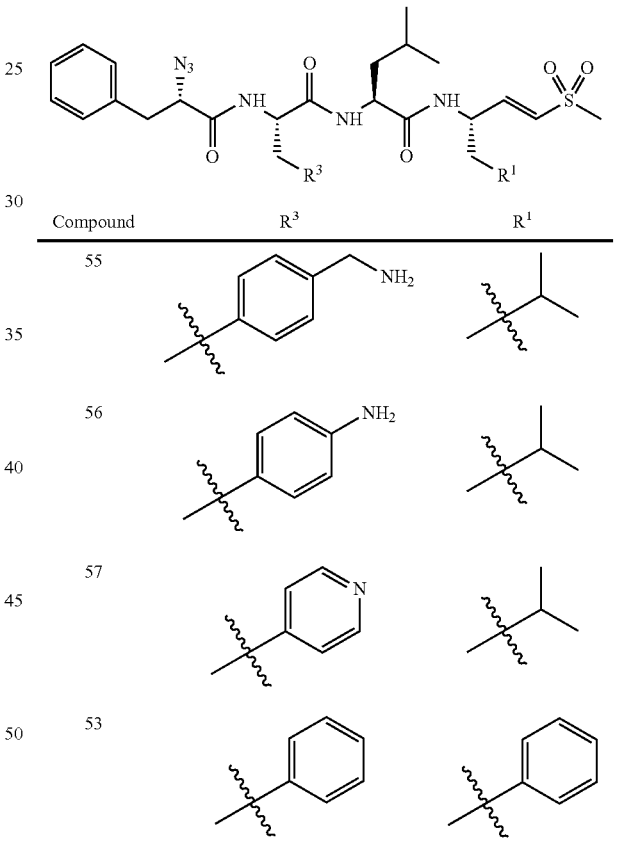

While compounds 50 and 51 had comparable potency and specificity to 4a (Table 9) compound 52 was more specific and potent than 4a. Replacing the P1 benzylamino side chain in compound 52 with an aniline side chain led to a loss of specificity (compound 53; Table 9) and replacing it with a pyridiyl side chain led to further loss of selectivity and to loss of potency (compound 54; Table 9). However, these compounds still retained specificity for the trypsin-like site and were more potent than compounds 45a and 46, which had leucine in the P3 position and the same P1 residues. Thus, we confirm the important role of basic residues in the P3 position for the selectivity of inhibitors of trypsin-like sites.

This analysis identified an equipotent inhibitor of chymotrypsin-like and trypsin-like sites (compound 55), wherein the P3 position was occupied by a benzylamine side chain (Table 11). Peptide vinyl sulfones with aniline and pyridyl side chains in the P3 and Leu in P1 (compounds 56 and 57) acted as inhibitors of chymotrypsin-like sites. Further, a compound with unsubstituted phenylalanines in both P1 and P3 (compound 58) was generated. This compound specifically inhibited the chymotrypsin-like sites. Thus, at least one strongly basic side chain in either P3 or P1 is needed to target these inhibitors on the trypsin-like sites.

TABLE 11

| Cmpd | IC$_{50}$ (μM) for sites: | | | IC$_{50}$ (Chym-L)/ IC$_{50}$ (Tr-L) |
|---|---|---|---|---|
| | Tr-L | Chym-L | Casp-L | |
| 55 | 0.18 | 0.01 | | 0.057 |
| 56 | 24 | <0.004 | >>30 | <0.00017 |
| 57 | 24 | 0.005 | >>30 | 0.00021 |
| 58 | >>30 | 1 | >>30 | n. d. |

>>30, no inhibition at 30 μM; >30, inhibition between 10 and 50% at 30 μM.

When comparing results obtained using activity assays in extracts of human cells and in purified rabbit 26S proteasomes, it was noted that inhibition of purified 26S was stronger than inhibition of proteasome in extracts. It was also noted that compound 52 behaved as the most potent inhibitor in extracts but was a less potent inhibitor of purified proteasome than compound 4a and compound 53. Furthermore, certain inhibitors of chymotrypsin-like sites (e.g., compounds 46, 56, and 57) inhibited these sites less potently and selectively in extracts than in purified proteasomes. Not wishing to be bound by theory, it is believed that a mixed population of proteasomes (e.g., presence of latent 20S (Kohler, et al. (2001) *Mol. Cell.* 7:1143-1152) or of 20S particles activated by PA200 or PA28), post-translational modifications, or association with proteasome-interacting proteins in extracts could be responsible for these differences.

Using click chemistry, a BODIPY-FL dye was attached to compounds 4a and 52 to generate activity-based probes for the s2 site. However, this modification reduced the specificity of 52 (compound 59) and led to complete loss of specificity of 4a (compound 39).

inhibitors, 4a, 48 and 52, were soaked in 20S yeast proteasome crystals. Data sets were collected for these three compounds and processed to 2.9, 2.7 and 3.1 Å with an R$_{free}$=0.230, 0.231, 0.238 for complexes with 4a, 48 and 52, respectively. The refined crystal structures revealed clear electron densities of all three compounds in the trypsin- and chymotrypsin-like active sites. In addition, the vinyl sulfone formed a covalent bond with to the Thr1 through a 1,4-Michael addition reaction and the peptide backbone was shown to adopt an antiparallel β-sheet conformation typical for peptide-based inhibitors.

The benzylamine group in P1 of all three compounds protruded into the spacious and hydrophilic S1 pocket of the trypsin-like site and was further stabilized through hydrogen bonding to the amine group of the Glu53 residue in P2. The P2 groups were solvent-exposed, whereas the P3 groups had a major effect in the binding profile. In the case of compound 52, the benzylamino group formed a tight hydrogen bond with Asp120 and accommodated the aromatic group perfectly in the S3 pocket through a series of van der Waals interactions, thereby profoundly stabilizing this moiety in the trypsin-like site. For compounds 4a and 48, the P3 moiety also protruded into the S3 side pocket, but there were no favorable interactions with the protein.

The aromatic capping group of 48 and the azide and phenyl groups of 4a and 52 protruded nicely into the S4 pocket. These residues were stabilized by van der Waals interactions with Leu115 and Ile116. The azido group of 4a and 48 was not clearly defined in the electron density, though weak hydrogen bonds with Gln22 in β2 and Asp114 in β3 most likely further stabilized this moiety.

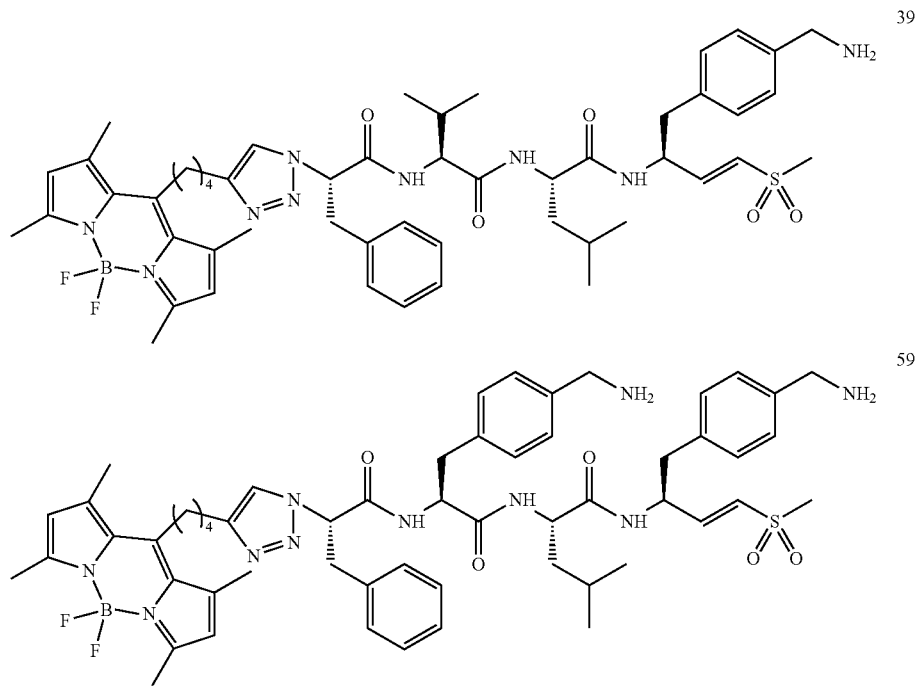

Compound 39 reacted with s2 and s5 subunits and equipotently inhibited trypsin- and chymotrypsin-like activities.

X-Ray Structure of Inhibitors Complexed with Yeast 20S Proteasomes.

To characterize the binding modes of inhibitors in the 20S proteasome, a structurally diverse set of the most potent To fully understand the molecular basis of specificity, interaction of inhibitors in the chymotrypsinlike site were analyzed. The benzylamino group in P1 protruded into the hydrophobic S1 pocket and was hydrogen bonded to Glu122 of β6 subunit. Similar to the trypsin-like site, the P2 side chains of the ligands were solvent exposed. The S3 pocket in the chymotrypsin-like site was so large that the Val, Leu, and benzylamino groups in 4a, 48, and 52, respectively, did not form significant interactions. The $N_3$ group in 4a and 52 was well defined in the electron density and formed strong hydrogen bonds with β6 Asp116, thus contributing to the stabilization of both inhibitors. The more flexible benzyl group of 4a and 52 protruded into the S4 pocket and fit better than the P4 group of 48.

To better correlate these structures of inhibitor complexes with yeast proteasomes with the specificity of these compounds in mammalian proteasomes, a superposition of both bovine and mouse constitutive proteasome (Huber, et al. (2012) *Cell* 148:727-38; Unno, et al. (2002) *Structure* 10:609-18) with all three yeast structures was performed. The structures of human proteasome subunits β2, β3, and β5, β6, which form the trypsin- and chymotrypsin-like sites, were not available; however, these proteins are 94-100% identical to their bovine and mouse counterparts. In yeast subunits, only 45-67% of residues are identical. The superposition revealed similar conformation of side chains, but with some notable differences.

Most of the differences were found in the chymotrypsin-like site. The most notable was the replacement Glu122 in the β5 subunit of yeast proteasome, which forms a hydrogen bond with the P1-benzylamine group, by Gln122 in bovine/mouse/human constitutive proteasome, which cannot form a tight bond to the amine group of the benzylamine. Furthermore, the azido group and phenyl ring fit adequately into the S4 pocket formed by His98 and Tyr98 of 136 in yeast, but in constitutive mouse, bovine and human proteasomes His98 is replaced by a larger Tyr98 that repels the benzyl group and does not allow its correct positioning. This leads to the conclusion that all three inhibitors are stronger inhibitors of chymotrypsin-like sites in the yeast proteasomes, resulting in lower selectivity for the trypsin-like sites. In this respect, the inhibition of yeast proteasomes by these inhibitors was measured (Table 12) and it was found that the ratio of $IC_H$ (Chym-L sites)/$IC_H$(Tr-L sites) was 400-fold higher for 4a and 8-fold higher for 48 in mammalian 26S proteasomes than for yeast 20S particles.

TABLE 12

| | $IC_{50}$ (µM) for yeast 20S proteasome: | | | $IC_{50}$ (Chym-L)/ $IC_{50}$ (Tr-L) | |
|---|---|---|---|---|---|
| Cmpd | Tr-L | Chym-L | Casp-L | Yeast | Rabbit |
| 4a | 2.6 | 2.7 | — | 1.04 | 447 |
| 48 | 1.6 | 19.3 | | 12.1 | 100 |
| 52 | 0.00055 | 6.1 | | 11090 | 1348 |

No inhibition of caspase-like sites was observed at 200 µM. Dose-response curves were used for determination of $IC_{50}$.

Compound 52 was a more selective inhibitor of trypsin-like sites in yeast proteasomes than in their mammalian counterparts (Table 12). This higher selectivity was likely a consequence of a completely different binding pattern of the P3 side chain in the trypsin-like site. In particular, the hydrogen bonding that precisely stabilizes the P3 side chain in the yeast 52 cannot be formed in mammalian proteasomes since Ala120 in yeast is replaced by Met120. However, the amine of the benyzlamine group is stabilized by other residues, including Ser112, and Tyr136 of subunit β3, which are more hydrophobic in yeast (Gly112, and Phe136, respectively). As the result, compound 52 is >4000-fold more potent inhibitor of yeast trypsin-like sites than is 4a (Table 12), while in mammalian proteasomes the potencies of 52 and 4a are comparable (Tables 7 and 9).

Effects of Compounds on Cells.

The five most potent compounds were assessed for their ability to inhibit proteasomes in a variety of cell lines. Given that the cell permeability of NC-022 varies from cell line to cell line, e.g., the $IC_{50}$ for inhibition of trypsin-like activity in the MM cell lines NCI-H929 and RPMI-8226 differ by 25-fold (Table 13), NCI-H929 and RPMI-8226 cells lines were used to evaluate proteasome inhibition by the five most potent and β2-specific inhibitors. All five inhibited proteasomes in MM cells (Table 13). Most importantly, the difference in proteasome inhibition between NCI-H929 and RPMI-8226 cells was only three-fold for 4a, 2.5-fold for 52, and five-fold for 51. Only compound 48 showed greater than ten-fold difference between cell lines. However, when the analysis was expanded to HEK-293 cells, only 4a showed good inhibition ($IC_{50}$=2.7 µM).

TABLE 13

| | | $IC_{50}$ (µM) for sites: | | |
|---|---|---|---|---|
| Compound | MM Cell Line | Tr-L | Chym-L | Casp-L |
| NC-022 | NCI-H929 | 0.9 | >>30 | >>30 |
| | RPMI-8226 | 24 | >>30 | >30 |
| 4a | NCI-H929 | 0.05 | 1.7 | 2.2 |
| | RPMI-8226 | 0.17 | 1.2 | 1.6 |
| 48 | NCI-H929 | 0.2 | 13 | >>30 |
| | RPMI-8226 | 3.2 | 15 | >30 |
| 52 | NCI-H929 | 0.17 | 10.5 | 17.4 |
| | RPMI-8226 | 0.42 | 27 | >30 |
| 51 | NCI-H929 | 0.11 | 3.6 | 22 |
| | RPMI-8226 | 0.58 | 7.2 | >30 |
| 50 | NCI-H929 | 0.27 | 10.5 | >30 |

Cells were treated with inhibitors for 6 hours followed by measurement of proteasome activities with PROTEASOME-GLO assay. >>30, no inhibition at 30 µM; >30, inhibition between 10 and 50% at 30 µM. Dose-response curves were used to calculate $IC_{50}$.

Compounds with two basic side chains, i.e., 51, 50, and especially 52, were much less permeable (Table 14).

TABLE 14

| | $IC_{50}$ (µM) for sites: | | |
|---|---|---|---|
| Compound | Tr-L | Chym-L | Casp-L |
| 4a | 2.7 | ~50 | >>50 |
| 52 | 50 | >50 | >>50 |
| 51 | 10 | >50 | >>50 |
| 50 | 27 | >50 | >>50 |

Cells were treated for 4 hours, followed by assessment of inhibition with the activity-based probe. >>50, no inhibition at 30 µM; >50, inhibition between 10 and 50% at 50 µM.

Although the vinyl sulfones were clearly more potent than the epoxyketones, they could potentially inhibit cathepsins (Screen, et al. (2010) *J. Biol. Chem.* 285:40125-34). To determine if this was the case, activity of cathepsins was measured in NCI-H929 cells with the most potent and specific vinyl sulfones (i.e., 4a, 52, 48, 50 and 51). For this purpose Z-FR-amc was used, which is cleaved by most cellular cathepsins (Kirschke, et al. (1994) *Methods Enzymol.* 244:500-11). Partial inhibition of cathepsins was observed in cells treated with 4a. Following an identical 6 hour treatment of cells, cathepsin inhibition occurred at a higher concentration than inhibition of trypsin-like activity and approximately at the same concentration as inhibition of caspase-like and chymotrypsin-like sites. Compound 52 was a slightly more potent inhibitor of cathepsins. Compound 48 did not cause any inhibition of cathepsins. Compound 51 behaved similarly to 4a. Compound 50-treated cells showed partly reduced cathepsin activity, but at concentrations lower than those that inhibit trypsin-like activity. These data showed that 4a, 52, 51, and 50 inhibit one or two cathepsins; that 4a and 51 are less potent inhibitors of these enzymes than of proteasome trypsin-like sites; that 52 inhibits cathepsins and proteasomes with a similar potency, and that 50 is a more potent inhibitor of cathepsin.

Based on the potency, cell permeability, and selectivity, compound 4a serves as a lead compound for additional analysis. It inactivates proteasome in RPMI-8226 cells at much faster rate than NC-022. In 4a-treated cells, steady-state inhibition is achieved after a 1 hour treatment, whereas in NC-022-treated cells, it was not achieved even after 6 hours. As described herein, NC-022 sensitizes myeloma cells to specific inhibitors of the chymotrypsin-like sites and to proteasome inhibitors bortezomib and carfilzomib. Similarly, compound 4a sensitized RPMI-8226 cells to bortezomib and was a slightly more potent sensitizer to carfilzomib than was NC-022. Inhibition of cathepsin(s) is unlikely to contribute to sensitization by 4a because E-64d, an inhibitor of all intracellular thiol proteases, did not sensitize cells to carfilzomib and did not significantly increase sensitization by NC-022. E-64d was used at 10 μM concentration, which completely inhibits thiol proteases (Screen, et al. (2010) supra). The sensitizing effect of 4a on carfilzomib was stronger than the additive effects of doxorubicin and dexamethasone and the synergistic effects of carfilzomib with histone deacetylase (HDAC) inhibitors. Thus, inhibitors of trypsin-like sites in combination with bortezomib or carfilzomib are more potent than the bortezomib combinations currently used clinically.

Example 13

Synthesis of Compounds

Synthesis of Para-Substituted Anilino Phenylalanine Epoxyketone and Vinyl Sulfone Warheads.

SCHEME 5

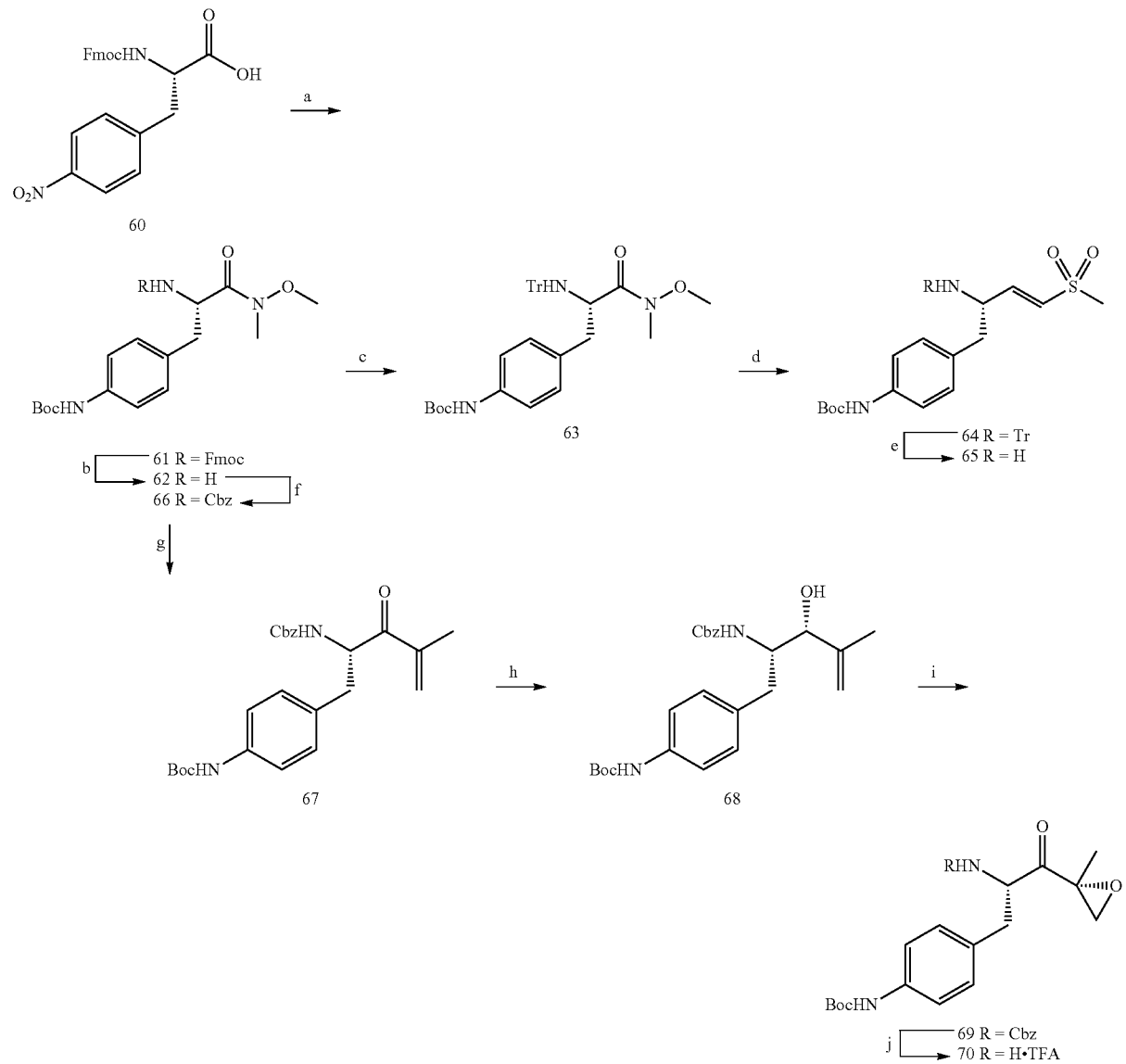

Reagents and conditions: (a) i) NH₄HCO₂H, Pd/C, MeOH; ii) Boc₂O, NaHCO₃, H₂O, 1,4-dioxane; iii) NH(Me)OMe.HCl, HCTU, DiPEA, DCM, 99%; (b) DBU, THF, 85%; (c) TrCl, Et₃N, DMAP, DCM, 96%; (d) i) LiAlH₄, Et₂O, 0° C.; ii) diethyl ((methylsulfonyl)methyl)phosphonate, NaH, THF, 0° C., 85%; (e) 1% TFA/DCM; (f) benzyl chloroformate, DiPEA, THF, 85%; (g) 2-bromopropene, tBuLi, THF, −78° C., 94%; (h) NaBH₄, CeCl₃.7H₂O, MeOH, 0° C., 92%; (i) i) tBuOOH, VO(Acac)₂, DCM, 0° C.; ii) Dess-Martin periodinane, DCM, 56%; (j) H₂, Pd black, TFA, MeOH.

(S)-(9H-fluoren-9-yl)methyl (3-(4-(tert-butyloxycarbonylamino)phenyl)-1-(methoxy(methyl)amino)-1-oxopropan-2-yl)carbamate (61)

To a suspension of Emoc-Phe(4-NO₂)—OH (60, 1.27 g, 2.93 mmol) in MeOH (60 mL) was added ammonium formate (10 eq., 30.0 mmol, 1.95 g) which resulted in a clear solution. Pd/C (10% w/w, 0.5 g) was added and the mixture was stirred at room temperature for hours after which TLC analysis indicated complete consumption of starting material. All solids were removed by filtration over CELITE and the filtrate was concentrated under reduced pressure. In order to remove excess ammonium formate the resulting product was coevaporated with a 3:1 (v/v) mixture of NeOH/H₂O (5×). Next, the residue was dissolved in H₂O (40 mL) containing NaHCO₃ (11.7 mmol, 0.99 g) and cooled to 0° C. To this was added Boc₂O (4.40 mmol, 0.99 g) in 1,4-dioxane (20 mL) and the mixture was allowed to stir at room temperature for 14 hours. The mixture was acidified with 10% w/v aq. HCl until pH 1 and extracted three times with EtOAc. The combined organic layers were dried over MgSO₄ and concentrated under reduced pressure. Finally the Weinreb amide was created in a peptide couplings procedure. The title compound was obtained after column chromatography (10%->50% EtOAc/PE) as a colorless oil (yield: 1.59 g, 2.91 mmol, 99%). ¹H NMR (400 MHz, CDCl₃): δ=7.70-7.66 (m, 2H), 7.53 (dd, J=12.68, 7.49 Hz, 2H), 7.33 (dd, J=13.74, 6.75 Hz, 4H), 7.27-7.21 (m, 2H), 7.11 (d, J=8.33 Hz, 2H), 6.17 (d, J=8.85 Hz, 1H), 5.06-4.98 (m, 1H), 4.32 (dd, J=10.25, 7.60 Hz, 1H), 4.25-4.19 (m, 1H), 4.14 (t, J=7.25, 7.25 Hz, 1H), 3.60 (s, 3H), 3.13 (s, 3H), 3.05 (dd, J=13.68, 5.45 Hz, 1H), 2.90 (dd, J=13.46, 7.49 Hz, 1H), 1.47 (s, 9H) ppm. ¹³C NMR (100 MHz, CDCl₃): δ=171.76, 155.65, 152.62, 143.49, 143.42, 140.78, 137.22, 130.36, 129.47, 127.25, 126.67, 124.85, 124.81, 119.51, 118.14, 79.76, 66.61, 61.13, 51.93, 46.66, 37.40, 31.64, 27.96 ppm.

(S)-tert-butyl (4-(2-amino-3-(methoxy(methyl)amino)-3-oxopropyl)phenyl)carbamate (62)

To a solution of compound 61 (1.50 g, 2.75 mmol) in THF (20 mL) was added DBU (1.5 mmol, 229 μL). After 10 minutes, TLC analysis indicated complete consumption of starting material. 1 M aq. HCl (30 mL) and EtOAc (25 mL) were added and the layers were separated. The organic layer was extracted with 1 M aq. HCl and the combined aqueous layers were basified with Na₂CO₃ until pH 10. This layer was extracted with EtOAc (3×) and the latter combined organic layers were dried over MgSO₄ and concentrated under reduced pressure. The title compound was obtained as a colorless oil (yield: 0.75 g, 2.34 mmol, 85%). ¹H NMR (400 MHz, CDCl₃) δ=7.62 (s, 1H), 7.33 (d, J=8.14 Hz, 2H), 7.09 (d, J=8.43 Hz, 2H), 4.02-3.95 (m, 1H). 3.57 (s, 3H), 3.16 (s, 3H), 2.98 (dd, J=13.30, 5.56 Hz, 1H), 2.65 (dd, J=13.25, 7.71 Hz, 1H), 1.93 (s, 2H), 1.49 (s, 9H) ppm. ¹³C NMR (100 MHz, CDCl₃) δ=175.13, 152.66, 137.04, 131.64, 129.29, 118.28, 79.54, 60.96, 52.38, 40.41, 31.82, 27.94 ppm. [α]_D²³=+19.6 (c=1, CHCl₃). HRMS: calcd. for C₁₆H₂₅N₃O₄ 324.19178 [M+H]⁺. found 324.19193.

(S)-tert-butyl (4-(3-(methoxy(methyl)amino)-3-oxo-2-(tritylamino)propyl)phenyl)carbamate (63)

To a solution of amine 62 (0.38 g, 1.16 mmol) in DCM (15 mL) was added Et₃N (1.2 eq., 1.40 mmol, 195 μL), and tritylchloride (1.2 eq., 1.40 mmol, 0.40 g) and the mixture was stirred for 14 hours. DCM was evaporated under reduced pressure and the residue was dissolved in EtOAc, extracted with 10 mM aq. HCl (2×) and brine, dried over MgSO₄ and concentrated under reduced pressure. The title compound was obtained after column chromatography (10%->50% EtOAc/PE) as a colorless foam (yield: 0.61 g, 1.11 mmol, 96%). ¹H NMR (400 MHz, CDCl₃): δ=7.46 (s, 1H), 7.36 (d, J=7.55 Hz, 6H), 7.22-7.02 (m, 13H), 6.95 (s, 1H), 4.01-3.95 (m, 1H), 3.10 (s, 3H), 2.88 (dd, J=13.31, 5.95 Hz, 1H), 2.73 (dd, J=13.03, 7.26 Hz, 1H), 2.61 (s, 3H), 1.49 (s, 9H) ppm. ¹³C NMR (100 MHz, CDCl₃): δ=174.86, 152.68, 145.93, 136.93, 132.49, 130.36, 128.66, 127.31, 125.82, 118.18, 79.91, 70.58, 59.93, 41.63, 31.92, 28.15 ppm. [α]_D²³=+75.8 (c=1, CHCl₃). HRMS: calcd. for C₃₅H₃₉N₃O₄ 566.30133 [M+H]⁺. found 566.30120.

(S,E)-tert-butyl (4-(4-(methylsulfonyl)-2-(tritylamino)but-3-en-1-yl)phenyl)carbamate (64)

This compound was prepared from Weinreb amide 63 (0.61 g, 1.11 mmol) in a synthetic procedure similar to that for compound and obtained after column chromatography (10%->40% EtOAc/PE) as a colorless foam (yield: 0.24 g, 0.41 mmol, 37%). ¹H NMR (400 MHz, CDCl₃): δ=7.45 (d, J=7.49 Hz, 6H), 7.28-7.15 (m, 12H), 6.81 (d, J=8.38 Hz, 2H), 6.58 (s, 1H), 6.56 (dd, J=15.04, 6.90 Hz, 1H), 5.92 (d, J=15.11 Hz, 1H), 3.45 (dd, J=12.80, 6.98 Hz, 1H), 2.58 (s, 3H), 2.51 (dd, J=13.36, 5.25 Hz, 1H), 2.28 (dd, J=13.33, 7.86 Hz, 1H), 1.49 (s, 9H) ppm. ¹³C NMR (100 MHz, CDCl₃): δ=152.59, 150.70, 145.91, 137.06, 130.81, 130.06, 128.55, 127.91, 126.64, 118.38, 80.34, 71.26, 55.55, 42.73, 41.68, 28.22 ppm. [α]_D²³=−14.8 (c=1, CHCl₃).

(S,E)-tert-butyl (4-(4-(methylsulfonyl)-2-aminobut-3-en-1-yl)phenyl)carbamate (65)

This compound was prepared from trityl protected amine 64 in a synthetic procedure similar to that for compound 60. The purity was checked by LC-MS analysis and the amine was subjected to the next step without further purification.

(S)-benzyl (3-(4-(tert-butyloxycarbonylamino) phenyl)-1-(methoxy(methyl)amino)-1-oxopropan-2-yl) carbamate (66)

To a solution of amine 62 (0.79 g, 2.43 mmol) in THF (20 mL) was added DiPEA (1.2 eq., 2.91 mmol, 482 μL), and benzylchloroformate (1.1 eq., 2.67 mmol, 392 μL) and the mixture was stirred for 4 hours in which a colorless solid precipitated. EtOAc was added and the mixture was extracted with 1 M aq. HCl (2×), sat. aq. NaHCO₃ and brine, dried over MgSO₄ and concentrated under reduced pressure. The title compound was obtained after column chromatography (10%->75% EtOAc/PE) as a colorless foam (yield: 0.95 g, 2.06 mmol, 85%). ¹H NMR (400 MHz, CDCl₃): δ=7.33-7.23 (m, 7H), 7.14 (s, 1H), 7.05 (d, J=8.21 Hz, 2H), 5.80 (d, J=8.71 Hz, 1H), 5.04 (dd, J=26.77, 12.39 Hz, 2H), 4.98-4.94 (m, 1H), 3.62 (s, 3H), 3.13 (s, 3H), 3.01 (dd, J=13.65, 5.91 Hz, 1H), 2.85 (dd, J=13.58, 7.35 Hz, 1H), 1.49 (s, 9H) ppm. $^{13}$C NMR (100 MHz, CDCl$_3$): δ=171.72, 155.64, 152.64, 137.21, 136.07, 130.35, 129.52, 128.13, 127.69, 127.64, 118.18, 79.88, 66.41, 61.21, 51.95, 37.53, 31.73, 28.05 ppm. [α]$_D^{23}$=+8.1 (c=1, CHCl$_3$). HRMS: calcd. for C$_{24}$H$_{31}$N$_3$O$_6$ 458.22856 [M+H]$^+$. found 458.22845.

(S)-benzyl (1-(4-(tert-butyloxycarbonylamino)phenyl)-4-methyl-3-oxopent-4-en-2-yl)carbamate (67)

This compound was prepared from Weinreb amide 66 (0.90 g, 1.96 mmol) in a synthetic procedure similar to that for compound 12 and obtained after column chromatography (10%->25% EtOAc/PE) as a colorless oil (yield: 0.70 g, 1.58 mmol, 81%). $^1$H NMR (400 MHz, CDCl$_3$): δ=7.37-7.20 (m, 7H), 6.92 (d, J=8.47 Hz, 2H), 6.81 (s, 1H), 6.00 (s, 1H), 5.86 (d, J=1.20 Hz, 1H), 5.66 (d, J=8.15 Hz, 1H), 5.30 (dd, J=14.10, 6.04 Hz, 1H), 5.07 (q, J=12.28, 12.28, 12.25 Hz, 2H), 3.07 (dd, J=13.85, 6.11 Hz, 1H), 2.89 (dd, J=13.86, 5.86 Hz, 1H), 1.84 (s, 3H), 1.49 (s, 9H) ppm. $^{13}$C NMR (100 MHz, CDCl$_3$): δ=199.48, 155.44, 152.61, 142.11, 137.24, 136.17, 129.91, 129.69, 128.31, 127.92, 127.84, 126.73, 118.22, 80.17, 66.63, 55.33, 38.83, 28.16, 17.54 ppm. [α]$_D^{23}$=+77.1 (c=1, CHCl$_3$). HRMS: calcd. for C$_{25}$H$_{30}$N$_2$O$_5$ 439.22275 [M+H]$^+$. found 439.22276.

Benzyl ((2S,3R)-1-(4-(tert-butyloxycarbonylamino) phenyl)-3-hydroxy-4-methylpent-4-en-2-yl)carbamate (68)

This compound was prepared from ketone 67 (0.70 g, 1.85 mmol) in a synthetic procedure similar to that for compound and obtained after column chromatography (10%->25% EtOAc/PE) as a colorless oil (yield: 0.71 g, 1.85 mmol, quant.). $^1$H NMR (400 MHz, CDCl$_3$): δ=7.32-7.18 (m, 7H), 7.04 (d, J=8.15 Hz, 2H), 6.77 (s, 1H), 5.17 (d, J=9.01 Hz, 1H), 5.05-4.91 (m, 4H), 4.14-4.10 (m, 1H), 4.05-3.97 (m, 1H), 3.01 (s, 1H), 2.86-2.78 (m, 1H), 2.64 (dd, J=14.18, 9.64 Hz, 1H), 1.76 (s, 3H), 1.50 (s, 9H) ppm. $^{13}$C NMR (100 MHz, CDCl$_3$): δ=156.03, 152.82, 144.45, 136.48, 136.33, 132.60, 129.65, 128.24, 127.79, 127.70, 118.49, 112.28, 80.17, 76.61, 66.37, 54.06, 33.46, 28.20, 18.71 ppm. [α]$_D^{23}$=-13.8 (c=1, CHCl$_3$). HRMS: calcd. for C$_{25}$H$_{32}$N$_2$O$_5$ 441.23840 [M+H]$^+$. found 441.23843.

Benzyl ((S)-3-(4-(tert-butyloxycarbonylamino)phenyl)-1-((R)-2-methyloxiran-2-yl)-1-oxopropan-2-yl) carbamate (69)

This compound was prepared from allylic alcohol 68 (0.70 g, 1.58 mmol) in a synthetic procedure similar to that for compound 14 and obtained after column chromatography (10%->30% EtOAc/PE) as a colorless oil (yield: 0.35 g, 0.76 mmol, 48%). $^1$H NMR (400 MHz, CDCl$_3$): δ=7.28-7.17 (m, 7H), 7.10 (s, 1H), 6.96 (d, J=8.42 Hz, 2H), 6.50 (s, 1H), 5.27 (d, J=8.21 Hz, 1H), 5.00-4.87 (m, 2H), 4.51 (dt, J=7.98, 7.96, 4.96 Hz, 1H), 3.19 (d, J=4.85 Hz, 1H), 2.98 (dd, J=14.06, 4.82 Hz, 1H), 2.82 (d, J=4.81 Hz, 1H) 2.62 (dd, J=14.04, 7.84 Hz, 1H), 1.47 (s, 3H), 1.43 (s, 9H) ppm. $^{13}$C NMR (100 MHz, CDCl$_3$): δ=207.87, 155.70, 155.61, 137.34, 136.02, 129.93, 129.78, 128.40, 128.04, 127.91, 118.53, 112.31, 82.57, 66.80, 59.12, 54.15, 52.24, 36.62, 28.25, 16.47 ppm. [α]$_D^{23}$=+91.3 (c=1, CHCl$_3$).

Tert-butyl (4-((S)-2-amino-3-((R)-2-methyloxiran-2-yl)-3-oxopropyl)phenyl)carbamate TFA salt (70)

This compound was prepared from Cbz protected amine 69 in a synthetic procedure similar to that for compound 15. The purity was checked by LC-MS analysis and the amine (as TFA salt) was subjected to the next step without further purification.

Synthesis of Para-Substituted 4-Pyridinoalanine and Lysine Vinyl Sulfone Warheads.

SCHEME 6

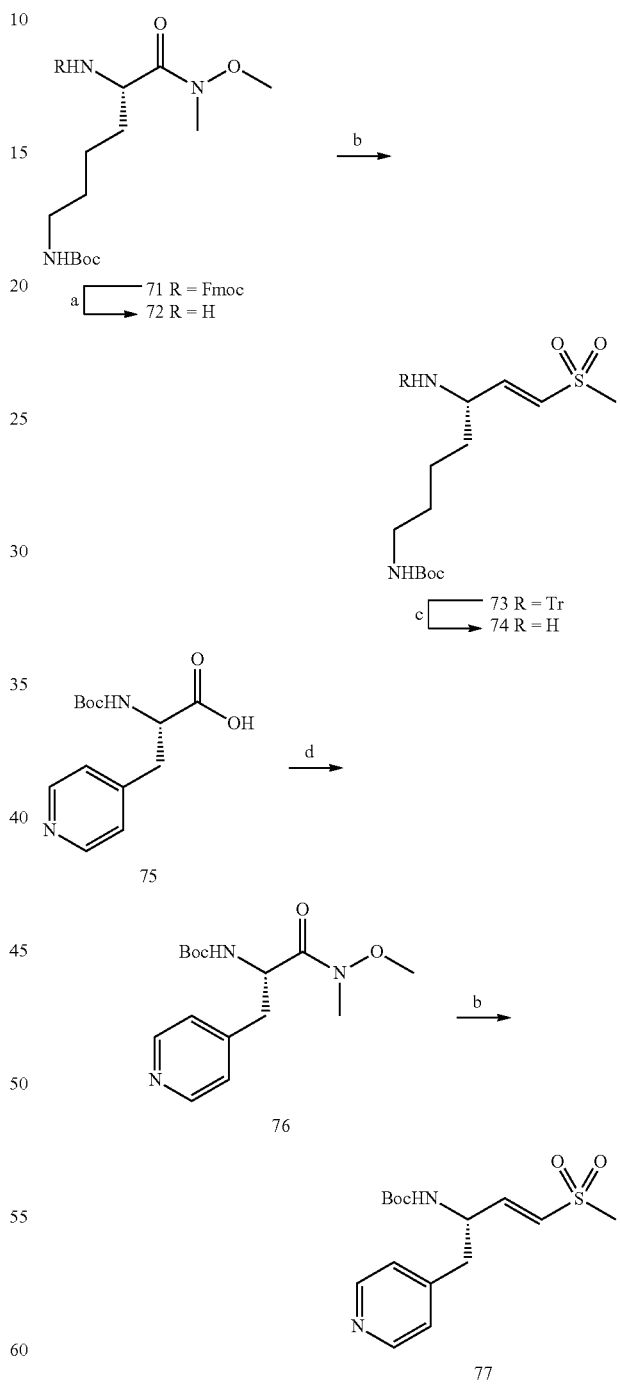

Reagents and conditions: (a) TrCl, DiPEA, DCM, 68%; (b) i) LiAlH$_4$, Et$_2$O, 0° C.; ii) diethyl ((methylsulfonyl)methyl) phosphonate, NaH, THF, 0° C., 64%; (c) 1% TFA/DCM; (d) NH(Me) OMe.HCl, HCTU, DiPEA, DCM, quant.

((S)-5-(trityl-amino)-5-(methoxy-methyl-carbamoyl)-pentyl)-carbamic acid tert-butyl ester (72)

H-Lys(Boc)-N(Me) OMe (71) (2.72 g, 6.44 mmol) was dissolved in DCM (40 mL) and to this were added DiPEA (2 eq., 12.9 mmol, 2.13 mL) and tritylchloride (1.1 eq., 7.08 mmol, 1.97 g). The reaction mixture was stirred for 15 hours, after which TLC analysis indicated complete consumption of starting material, extracted with $H_2O$ (4×) and dried over $MgSO_4$. The title compound was obtained after purification by column chromatography (DCM->3% MeOH/DCM) as a colorless foam (yield: 2.30 g, 4.32 mmol, 68%). $^1H$ NMR (400 MHz, $CDCl_3$): δ=7.49 (d, J=7.47 Hz, 6H), 7.23 (t, J=7.60, 7.60 Hz, 6H), 7.14 (t, J=7.25 Hz, 3H), 4.63 (s, 1H), 3.81 (s, 1H), 3.31 (s, 3H), 3.15-3.03 (m, 2H), 2.70 (s, 3H), 1.81-1.68 (m, 1H), 1.61-1.29 (m, 14H) ppm. $^{13}C$ NMR (100 MHz, $CDCl_3$): δ=175.06, 155.58, 145.92, 128.52, 127.17, 125.77, 78.26, 70.68, 59.98, 51.52, 40.00, 34.85, 31.77, 29.92, 28.04, 21.55 ppm.

(S,E)-tert-butyl (5-(trityl-amino)-7-(methylsulfonyl)hept-6-en-1-yl)carbamate (73)

This compound was prepared from Weinreb amide 72 (0.81 g, 1.52 mmol) in a synthetic procedure similar to that for compound and obtained after column chromatography (0%->30% EtOAc/PE) as a colorless foam (yield: 0.53 g, 0.97 mmol, 64%). $^1H$ NMR (400 MHz, $CDCl_3$): δ=7.51-7.46 (m, 6H), 7.29-7.23 (m, 6H), 7.20-7.14 (m, 3H), 6.62 (dd, J=15.05, 6.98 Hz, 1H), 6.22 (d, J=15.06 Hz, 1H), 4.68-4.61 (m, 1H), 3.28-3.20 (m, 1H), 2.98-2.89 (m, 2H), 2.71-2.67 (m, 3H), 1.42 (s, 9H), 1.30-0.81 (m, 6H) ppm. $^{13}C$ NMR (100 MHz, $CDCl_3$): δ=155.64, 150.93, 145.89, 128.38, 128.01, 127.69, 126.42, 78.62, 71.06, 53.72, 42.56, 39.77, 35.29, 29.54, 28.14, 22.08 ppm.

(S,E)-tert-butyl (5-amino-7-(methylsulfonyl)hept-6-en-1-yl)carbamate (74)

This compound was prepared from trityl protected amine 73 in a synthetic procedure similar to that for compound 18. The purity was checked by LC-MS analysis and the amine was subjected to the next step without further purification.

(S)-tert-butyl (1-(methoxy(methyl)amino)-1-oxo-3-(pyridin-4-yl)propan-2-yl)carbamate (76)

To a mixture of Boc-β-(4-pyridyl)-L-alanine (75, 300 mg, 1.08 mmol) and NH(Me) OMe.HCl (1.2 eq., 1.30 mmol, 129 mg) in DCM (10 mL) was added HCTU (1.2 eq., 1.30 mmol, 536 mg) and DiPEA (3.5 eq., 3.78 mmol, 625 μL) and the mixture was stirred for 1 hour after which TLC analysis indicated complete conversion of starting material. The solvent was evaporated under reduced pressure en the residue was taken up in EtOAc, extracted with sat. aq. $NaHCO_3$ (2×) and brine, dried over $MgSO_4$ and concentrated in vacuo. The title compound was obtained after purification by column chromatography (EtOAc->2% MeOH/EtOAc) as a pale yellow solid (yield: 334 mg, 1.08 mmol, quant.). $^1H$ NMR (400 MHz, $CD_3OD$): δ=8.40 (d, J=4.59 Hz, 2H), 7.29 (d, J=4.88 Hz, 2H), 6.97 (d, J=7.26 Hz, 1H), 4.77-4.68 (m, 1H), 3.76 (s, 3H), 3.15 (s, 3H), 3.02 (dd, J=13.59, 4.85 Hz, 1H), 2.83-2.77 (m, 1H), 1.32 (s, 9H) ppm. $^{13}C$ NMR (100 MHz, $CD_3OD$): δ=173.49, 157.58, 149.88, 149.50, 126.48, 80.55, 62.25, 52.71, 38.03, 32.49, 28.66 ppm. $[α]_D^{23}$=−2.9 (c=1, MeOH). HRMS: calcd. for $C_{15}H_{43}N_3O_4$ $[M+H]^+$310.17613. found 310.17615.

(S,E)-tert-butyl (4-(methylsulfonyl)-1-(pyridin-4-yl)but-3-en-2-yl)carbamate (77)

Weinreb amide 76 (0.33 g, 1.08 mmol) was dissolved in THF (15 mL), put under an argon atmosphere and cooled to 0° C. $LiAlH_4$ (1.5 eq., 1.68 mmol, 1.68 mL of a 1 M solution in THF) was added slowly and the mixture was stirred at 0° C. for 1 hour after which TLC analysis indicated complete conversion of the starting compound. 0.1 M aq. HCl (1 mL) was slowly added and the mixture was stirred vigorously for 5 minutes. The organic layer was extracted with sat. aq. $NaHCO_3$ (2×) and brine, dried over $MgSO_4$ and concentrated under reduced pressure. Diethyl ((methylsulfonyl)methyl) phosphonate (1.5 eq., 1.68 mmol, 0.39 g) was dissolved in THF (20 mL) and cooled to 0° C. under an argon atmosphere. NaH (1.3 eq., 1.46 mmol, 58.0 mg, 60% w/w in mineral oil) was slowly added and the mixture was stirred at 0° C. for 30 minutes. Next, the freshly obtained aldehyde (in THF (2 mL)) was slowly added and the mixture was stirred for 2 hours while slowly warming it to room temperature. After this time, TLC analysis indicated complete conversion of the aldehyde. The reaction was quenched by addition of 1 M aq. HCl (1 mL) after which the mixture was diluted with EtOAc and extracted with sat. aq. $NaHCO_3$ (2×) and brine, dried over $MgSO_4$ and concentrated under reduced pressure. The title compound was obtained after column chromatography (40%->80% Acetone/PE) as a colorless solid (yield: 117 mg, 0.36 mmol, 32%). $^1H$ NMR (400 MHz, $CDCl_3$): δ=8.50 (d, J=5.28 Hz, 2H), 7.15 (d, J=5.90 Hz, 2H), 6.92 (dd, J=15.10, 4.76 Hz, 1H), 6.53 (d, J=15.10 Hz, 1H), 5.56 (d, J=8.99 Hz, 1H), 4.80-4.72 (m, 1H), 3.02-2.84 (m, 2H), 2.93 (s, 3H), 1.39 (s, 9H) ppm. $^{13}C$ NMR (100 MHz, $CDCl_3$): δ=154.87, 149.59, 146.40, 145.41, 130.04, 124.51, 80.10, 51.10, 42.58, 39.48, 28.06 ppm. $[α]_D^{23}$=−6.0 (c=1, MeOH). HRMS: calcd. for $C_{15}H_{22}N_2O_4S$ $[M+H]^+$327.13730. found 327.13741.

Azide Coupling Towards the Target Inhibitors.

SCHEME 6

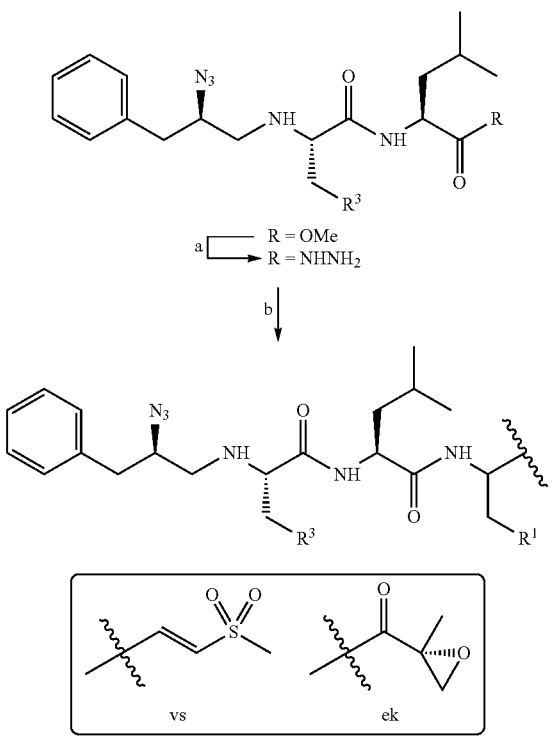

Reagents and Conditions:

(a) NH$_2$NH$_2$·H$_2$O, MeOH; (b) i) tBuONO, HCl, DMF, DCM, −30° C.; ii) amine (15, 18, 65, 70, 73, 77), DiPEA.

N$_3$-Phe-Leu-Leu-NHNH$_2$ (78).

This compound was synthesized via general Boc-based peptide coupling procedures using HCTU from H-Leu-OMe, Boc-Leu-H and N$_3$-Phe-H. The last step involved the introduction of the hydrazide by stirring of a mixture containing tripeptide N$_3$-Phe-Leu-Leu-OMe (1.51 g, 3.49 mmol) and hydrazine monohydrate (30 eq., 105 mmol, 5.1 mL) in NeOH (30 mL) for 15 hours at room temperature. The title compound was obtained after coevaporation of the mixture with toluene (3×) as a colorless solid (yield: 1.51 g, 3.49 mmol, quant.). LC-MS: R$_t$ (min): 6.87 (ESI-MS (m/z): 432.13 (M+H)$^+$.

Cbz-Phe(4-CH$_2$NHBoc)-Leu-OMe (79).

Cbz-Phe(4-CH$_2$NHBoc)-OH (214 mg, 0.5 mmol, 1 equiv.) was dissolved in DCM. HBTU (228 mg, 0.6 mmol, 1.2 equiv.), HCl.H-Leu-OMe (100 mg, 0.55 mmol, 1.1 equiv.) and DiPEA (0.29 ml, 1.75 mmol, 3.5 equiv.) were added and the mixture was stirred for 2 hours before being concentrated. The residue was dissolved in ethyl acetate (EA) and washed with 1M HCl (2×), sat. aq. NaHCO$_3$ (4×), brine and dried over MgSO$_4$. Column chromatography (tol->30% EA:tol) yielded the title compound (282 mg, 508 µmol, quant.). $^1$H NMR (400 MHz, CDCl$_3$): δ ppm 7.35-7.22 (m, 5H), 7.19-7.04 (m, 4H), 6.81 (d, J=6.7 Hz, 1H), 5.76 (d, J=8.4 Hz, 1H), 5.16-4.94 (m, 2H), 4.69-4.45 (m, 2H), 4.26-4.11 (m, 2H), 3.67 (s, 3H), 3.13-2.88 (m, 2H), 1.64-1.47 (m, 3H), 1.44 (s, 9H), 0.94-0.81 (m, 6H). $^{13}$C NMR (101 MHz, CDCl$_3$): δ ppm 172.83, 170.76, 155.81, 137.23, 136.04, 135.30, 129.37, 128.28, 127.92, 127.70, 127.57, 79.13, 66.70, 55.73, 52.06, 50.51, 44.19, 41.08, 37.94, 28.23, 24.51, 22.52, 21.69.

H-Phe(4-CH$_2$NHBoc)-Leu-OMe (80). Cbz-Phe(4-CH$_2$NHBoc)-Leu-OMe 79 (282 mg, 508 µmol) was dissolved in MeOH. TFA (45 µl, 607 µmol, 1.2 equiv.) was added and the mixture was bubbled through with Ar for 20 minutes. 10% Pd/C was added (50 mg) and the flask was filled with an H$_2$ atmosphere for 3 hours. The mixture was filtered over CELITE and concentrated. The residue was dissolved in DCM and sat. aq. NaHCO$_3$ and the aqueous layer was extracted with DCM (3×). The organic layers were dried over Na$_2$SO$_4$ and concentrated to yield the title compound (221 mg, quant.), which was used without further purification. $^1$H NMR (400 MHz, CDCl$_3$): δ ppm 7.67 (d, J=8.6 Hz, 1H), 7.22 (d, J=8.0 Hz, 2H), 7.17 (d, J=8.1 Hz, 2H), 5.11 (s, 1H), 4.61 (td, J=8.9, 5.0 Hz, 1H), 4.28 (d, J=5.6 Hz, 2H), 3.72 (s, 3H), 3.61 (dd, J=9.0, 4.0 Hz, 1H), 3.19 (dd, J=13.7, 3.9 Hz, 1H), 2.72 (dd, J=13.7, 9.0 Hz, 1H), 1.70-1.48 (m, 3H), 1.45 (s, 9H), 1.03-0.89 (m, 6H). $^{13}$C NMR (101 MHz, CDCl$_3$): δ ppm 173.91, 173.25, 155.77, 137.47, 136.49, 129.35, 127.56, 79.21, 56.06, 52.03, 50.13, 44.07, 41.22, 40.26, 28.23, 24.64, 22.69, 21.68.

N$_3$-Phe-Phe(4-CH$_2$NHBoc)-Leu-OMe (81).

H-Phe(4-CH$_2$NHBoc)-Leu-OMe 80 (68 mg, 161 µmol, 1 equiv.) was dissolved in DCM (5 ml) and N$_3$-Phe-OH (37 mg, 193 µmol, 1.2 equiv.), HBTU (79 mg, 209 µmol, 1.3 equiv.) and DiPEA (67 µl, 403 µmol, 2.5 equiv.) were added and the mixture was stirred for 90 minutes before being washed with 1M HCl (2×), sat aq. NaHCO$_3$ (3×) and dried over Na$_2$SO$_4$. Column chromatography (10% EA:tol->35% EA:tol) yielded the title compound (71 mg, 119 µmol, 74%). $^1$H NMR (400 MHz, CDCl$_3$): δ ppm 7.40-7.20 (m, 5H), 7.17 (d, J=7.8 Hz, 2H), 7.04 (d, J=7.9 Hz, 2H), 6.97 (d, J=8.1 Hz, 1H), 6.34 (d, J=7.5 Hz, 1H), 4.93 (s, 1H), 4.67 (dd, J=14.3, 7.1 Hz, 1H), 4.51 (td, J=8.2, 5.4 Hz, 1H), 4.26 (d, J=5.2 Hz, 2H), 4.16 (dd, J=8.2, 4.2 Hz, 1H), 3.70 (s, 3H), 3.24 (dd, J=14.1, 4.1 Hz, 1H), 3.08-2.82 (m, 3H), 1.62-1.46 (m, 3H), 1.45 (s, 9H), 0.88 (d, J=6.1 Hz, 6H). $^{13}$C NMR (101 MHz, CDCl$_3$): δ ppm 172.71, 169.82, 168.38, 155.80, 137.63, 135.83, 135.00, 129.51, 129.42, 128.60, 127.81, 127.24, 79.36, 65.13, 54.03, 52.25, 50.80, 44.37, 41.36, 38.33, 37.89, 28.33, 24.70, 22.58, 21.91.

N$_3$-Phe-Phe (4-CH$_2$NHBoc)-Leu-NHNH2 (82).

Methyl ester (71 mg, 119 µmol) was dissolved in MeOH (5 ml). Hydrazine hydrate (350 µl, 7.1 mmol, 60 equiv.) was added and the mixture was stirred overnight before being coevaporated with tol (3×). The residue was used without further purification. LC/MS: R$_t$ 7.52 min (linear gradient 10->90% MeCN+0.1% TFA, 15 minutes), (ESI-MS (m/z): 595.00 (M+H)$^+$). $^1$H NMR (400 MHz, CD$_3$OD): δ ppm 7.26 (ddd, J=19.9, 13.4, 7.9 Hz, 7H), 7.15 (d, J=8.0 Hz, 2H), 4.63 (t, J=7.2 Hz, 1H), 4.36 (dd, J=9.0, 6.0 Hz, 1H), 4.21 (s, 2H), 4.10 (dd, J=8.7, 5.1 Hz, 1H), 3.13 (dd, J=13.9, 5.1 Hz, 1H), 3.06 (dd, J=13.7, 6.5 Hz, 1H), 2.96-2.80 (m, 2H), 1.70-1.51 (m, 3H), 1.46 (s, 9H), 0.96 (d, J=6.4 Hz, 3H), 0.92 (d, J=6.3 Hz, 3H).

Fmoc-Phe(4-NHBoc)-Leu-OMe (83).

Fmoc-Phe(4-NHBoc)-OH (210 mg, 418 µmol, 1 equiv.) was dissolved in DCM and HCl.H-Leu-OMe (77 mg, 460 µmol, 1.1 equiv.), HBTU (190 mg, 502 µmol, 1.2 equiv.) and DiPEA (242 µl, 1.46 mmol, 3.5 equiv.) were added and the mixture stirred for 1 hour. after which it was washed with 1M HCl (2×), sat. aq. NaHCO$_3$ (4×) and brine and dried over MgSO$_4$. Column chromatography (10% acetone:PE->20% acetone:PE) yielded the title compound (206 mg, 294 µmol, 70%). $^1$H NMR (400 MHz, CDCl$_3$): δ ppm 7.76 (d, J=7.5 Hz, 2H), 7.54 (t, J=6.9 Hz, 2H), 7.39 (t, J=7.4 Hz, 2H), 7.35-7.20 (m, 4H), 7.11 (d, J=7.1 Hz, 2H), 6.54 (s, 1H), 6.29 (d, J=6.6 Hz, 1H), 5.44 (d, J=7.2 Hz, 1H), 4.55 (td, J=8.4, 5.4 Hz, 1H), 4.41 (dd, J=10.3, 7.2 Hz, 1H), 4.32 (s, 1H), 4.18 (t, J=6.9 Hz, 1H), 3.68 (s, 3H), 3.15-2.94 (m, 2H), 1.65-1.39 (m, 3H), 1.51 (s, 9H), 0.97-0.78 (m, 6H). $^{13}$C NMR (101 MHz, CDCl$_3$): δ ppm 172.74, 170.69, 155.89, 152.64, 143.67, 143.60, 141.16, 137.31, 130.58, 129.83, 127.64, 127.01, 124.98, 119.88, 118.55, 80.41, 67.11, 55.88, 52.17, 50.75, 46.95, 41.31, 37.78, 28.25, 24.63, 22.58, 21.81.

H-Phe(4-MHBoc)-Leu-OMe (84)

Fmoc-Phe(4-NHBoc)-Leu-OMe 83 (181 mg, 294 µmol, 1 equiv.) was dissolved in THF and EtSH (220 µl, 2.94 mmol, 10 equiv.) and DBU (one drop) were added and the mixture stirred for 30 minutes. After concentration, column chromatography (50% EA:PE->EA->10% MeOH:EA) yielded the title compound (120 mg, 294 µmol, quant). $^1$H NMR (400 MHz, CDCl$_3$:CD$_3$OD 1:1): δ ppm 7.35 (d, J=7.8 Hz, 2H), 7.13 (d, J=8.2 Hz, 2H), 4.48 (t, J=5.3 Hz, 1H), 3.71 (s, 3H), 3.68-3.61 (m, 1H), 3.04 (dd, J=13.6, 4.8 Hz, 1H), 2.77 (dd, J=13.6, 7.9 Hz, 1H), 1.66-1.56 (m, 3H), 1.52 (s, 9H), 1.08-0.81 (m, 6H). $^{13}$C NMR (101 MHz, CDCl$_3$ CD$_3$OD): δ ppm 173.84, 172.56, 153.26, 137.23, 130.17, 128.88, 118.11, 81.21, 55.02, 51.11, 49.95, 39.73, 39.23, 27.10, 23.88, 21.59, 20.30.

N$_3$-Phe-Phe (4-NHBoc)-Leu-OMe (85).

H-Phe (4-NHBoc)-Leu-OMe 84 (120 mg, 294 µmol, 1 equiv.) was dissolved in DCM. N$_3$-Phe-OH (82 mg, 430 µmol, 1.5 equiv.), HBTU (163 mg, 430 µmol, 1.5 equiv.) and DiPEA (161 µl, 975 µmol, 3.3 equiv.) were added and the mixture stirred for 2 hours before being washed with 1M HCl (2×), sat. aq. NaHCO$_3$ (4×) and brine and dried over MgSO$_4$. Column chromatography (10% EA:tol->40% EA:tol) yielded the title compound (160 mg, 276 µmol, 94%). $^1$H-NMR (400 MHz, CDCl$_3$): δ ppm 7.55-7.20 (m, 7H), 7.01 (d, J=8.4 Hz, 2H), 6.92 (d, J=8.0 Hz, 1H), 6.60 (s, 1H), 6.26 (d, J=7.9 Hz, 1H), 4.62 (dd, J=14.3, 7.2 Hz, 1H), 4.50 (td, J=8.3, 5.5 Hz, 1H), 4.18 (dd, J=8.2, 4.1 Hz, 1H), 3.70 (s, 3H), 3.25 (dd, J=14.1, 4.1 Hz, 1H), 3.02-2.75 (m, 3H), 1.68-1.37 (m, 3H), 1.51 (s, 9H), 0.88 (d, J=6.1 Hz, 6H). $^{13}$C NMR (101 MHz, CDCl$_3$): δ ppm 172.67, 170.14, 168.53, 152.70, 137.36, 135.86, 130.22, 129.80, 129.36, 128.54, 127.15, 118.50, 80.40, 65.02, 53.99, 52.19, 50.86, 41.17, 38.30, 37.60, 28.22, 24.66, 22.53, 21.86.

N$_3$-Phe-Phe(4-NHBoc)-Leu-NHNH$_2$ (86).

N$_3$-Phe-Phe(4-NHBoc)-Leu-OMe (160 mg, 276 μmol) was dissolved in MeOH and hydrazine hydrate (800 μl, 16.6 mmol, 60 equiv.) was added and the mixture was stirred overnight. Co-evaporation with toluene (3×) yielded the title compound which was used without further purification. LC/MS: R$_t$ 7.54 minutes (linear gradient 10->90% MeCN+ 0.1% TFA, 15 minutes), (ESI-MS (m/z): 581.13. $^1$H NMR (400 MHz, CD$_3$OD): δ ppm 7.40-7.17 (m, 7H), 7.02 (d, J=8.5 Hz, 2H), 4.61 (t, J=7.0 Hz, 1H), 4.35 (t, J=7.3 Hz, 1H), 4.13 (dd, J=8.6, 4.8 Hz, 1H), 3.15 (dd, J=14.0, 4.7 Hz, 1H), 3.00-2.81 (m, 3H), 1.60-1.45 (m, 3H), 1.51 (s, 9H), 0.93 (d, J=6.0 Hz, 3H), 0.89 (d, J=5.9 Hz, 3H).

Boc-Ala(4-pyridine)-Leu-OMe (87).

Boc-Ala(4-pyridine)-OH (133 mg, 500 μmol, 1 equiv.) was dissolved in DMF and HCl.H-Leu-OMe (92 mg, 550 μmol, 1.1 equiv.), HBTU (228 mg, 600 μmol, 1.2 equiv.) and DiPEA (290 μl, 1.75 mmol, 3.5 equiv.) were added and the mixture stirred for 2 hours. The mixture was diluted with EA and washed with sat. aq. NaHCO$_3$. The aqueous layer was extracted with DCM and the combined organic fractions were dried over Na$_2$SO$_4$ and concentrated. Column chromatography (1:1 tol:EA->1:2->1:4 tol:EA) yielded the title compound (164 mg, 417 μmol, 83%). $^1$H NMR (400 MHz, CDCl$_3$:CD$_3$OD 1:1): δ ppm 8.43 (d, J=4.4 Hz, 2H), 8.14 (d, J=7.7 Hz, 1H), 7.29 (d, J=5.1 Hz, 2H), 6.37 (d, J=8.7 Hz, 1H), 4.57-4.49 (m, 1H), 4.49-4.41 (m, 1H), 3.72 (s, 3H), 3.18 (dd, J=13.8, 5.5 Hz, 1H), 2.90 (dd, J=13.8, 8.7 Hz, 1H), 1.77-1.57 (m, 3H), 1.38 (s, 9H), 0.94 (dd, J=9.7, 6.0 Hz, 6H). $^{13}$C NMR (101 MHz, CDCl$_3$:CD$_3$OD 1:1): δ ppm 172.70, 171.29, 155.41, 148.08, 147.07, 124.75, 79.47, 53.90, 51.53, 50.40, 50.30, 48.39, 48.18, 47.97, 47.75, 47.54, 39.99, 39.94, 37.07, 27.39, 24.13, 22.02, 20.73.

N$_3$-Phe-Ala(4-pyridine)-Leu-OMe (88).

Boc-Ala-(4-pyridine)-Leu-OMe 87 (164 mg, 417 μmol) was dissolved in 1:1 DCM:TFA and stirred for 30 minutes before being co-evaporated with toluene (3×). In a separate flask, N$_3$-Phe-OH (88 mg, 459 μmol, 1.1 equiv.) was dissolved in DCM and HBTU (174 mg, 459 μmol, 1.1 equiv.), DiPEA (310 μl, 1.88 mmol, 4.5 equiv.) were added. After 5 minutes of stirring, this mixture was added to the flask containing TFA salt of H-Ala(4-pyridine)-Leu-OMe and this mixture was stirred for 1 hour before being washed with H$_2$O (2×). Column chromatography (DCM->2% MeOH:DCM) yielded the title compound (148 mg, 317 μmol, 76%). $^1$H NMR (400 MHz, CDCl$_3$): δ ppm 8.44 (d, J=5.4 Hz, 2H), 7.39-7.10 (m, 7H), 7.00 (d, J=5.7 Hz, 2H), 4.82 (dd, J=14.7, 6.7 Hz, 1H), 4.62-4.47 (m, 1H), 4.18 (dd, J=8.1, 4.3 Hz, 1H), 3.71 (s, 3H), 3.23 (dd, J=14.0, 4.2 Hz, 1H), 3.08-2.87 (m, 3H), 1.75-1.37 (m, 3H), 0.89 (d, J=6.1 Hz, 6H). $^{13}$C NMR (101 MHz, CDCl$_3$): ppm 172.70, 169.52, 168.56, 149.45, 145.23, 135.63, 129.36, 128.56, 127.26, 124.71, 64.85, 52.85, 52.25, 50.87, 40.94, 38.12, 37.50, 24.71, 22.54, 21.73.

N$_3$-Phe-Ala(4-pyridine)-Leu-NHNH$_2$ (89).

Methyl ester (113 mg, 242 μmol) was dissolved in MeOH and hydrazine hydrate (700 μl, 14.5 mmol, 60 equiv.) was added and the mixture was stirred overnight. Co-evaporation with toluene (3×) yielded the title compound which was used without further purification. LC/MS: R$_t$ 4.86 min (linear gradient 10->90% MeCN+0.1% TFA, 15 minutes), (ESI-MS (m/z): 467.20. $^1$H NMR (400 MHz, CD$_3$OD): δ ppm 8.40 (d, J=5.7 Hz, 2H), 7.35-7.17 (m, 5H), 7.14 (d, J=5.9 Hz, 2H), 4.75 (dd, J=8.3, 5.6 Hz, 1H), 4.40-4.29 (m, 1H), 4.10 (dd, J=8.3, 4.9 Hz, 1H), 3.22-3.05 (m, 2H), 2.92 (ddd, J=14.0, 10.7, 8.5 Hz, 2H), 1.67-1.51 (m, 3H), 0.95 (d, J=6.1 Hz, 3H), 0.91 (d, J=6.0 Hz, 3H).

General Procedure: Azide Couplings and De-Protection.

Compounds 45-58 were prepared via azide coupling of properly protected tripeptide hydrazide (e.g., N$_3$-Phe-Leu-Leu-NHNH$_2$ for compounds 45-48) and properly protected vinyl sulfone amines and epoxyketone amines. The appropriate hydrazide was dissolved in 1:1 DMF:DCM (v/v) and cooled to −30° C. tBuONO (1.1 eq.) and HCl (4M solution in 1,4-dioxane, 2.8 eq.) were added and the mixture was stirred for 3 hours at −30° C., after which TLC analysis (10% MeOH/DCM, v/v) showed complete consumption of the starting material. The epoxyketone or vinyl sulfone as a free amine was added to the reaction mixture as a solution in DMF. DiPEA (5 eq.) was added to the reaction mixture, which was allowed to warm to room temperature slowly overnight. The mixture was diluted with ethyl acetate and extracted with H$_2$O (3×). The organic layer was dried over MgSO$_4$ and purified by flash column chromatography. For deprotection, the product was dissolved in dichloromethane (2.5 mL/mmol). TFA (2.5 mL/mmol) was added and the mixture was stirred for 30 minutes, after which it was concentrated under reduced pressure in the presence of toluene (3×). The obtained crude product was purified by RP-HPLC. Tripeptide hydrazide were prepared by hydrazynolysis of tripeptide methyl esters (Verdoes, et al. (2007) *Bioorg. Med. Chem. Lett.* 17:6169-71) synthesized by standard procedures of solution peptide chemistry.

N$_3$-Phe-Leu-Leu-Phe(4-NH$_2$)-VS (45a)

(SEQ ID NO:12). $^1$H NMR (400 MHz, CD$_3$OD): δ=8.25 (d, J=8.29 Hz, 1H), 7.93 (d, J=7.42 Hz, 1H), 7.32 (d, J=8.47 Hz, 2H), 7.26-7.19 (m, 8H), 6.77 (dd, J=15.20, 5.35 Hz, 1H), 6.53 (dd, J=15.21, 1.52 Hz, 1H), 4.81-4.73 (m, 1H), 4.33-4.27 (m, 1H), 4.27-4.22 (m, 1H), 4.14 (dd, J=8.58, 4.82 Hz, 1H), 3.16 (dd, J=14.07, 4.83 Hz, 1H), 2.99-2.90 (m, 3H), 2.89 (s, 3H), 1.59-1.38 (m, 6H), 0.89 (dd, J=6.13, 3.43 Hz, 6H), 0.85 (d, J=6.11 Hz, 6H) ppm. $^{13}$C NMR (100 MHz, CD$_3$OD): δ=174.55, 174.47, 171.98, 146.53, 138.54, 137.85, 132.22, 132.01, 130.48, 129.68, 128.14, 123.43, 65.57, 53.73, 53.70, 52.53, 42.79, 41.83, 41.60, 39.97, 38.72, 25.94, 25.86, 23.48, 23.46, 21.94 ppm. LC-MS: R$_t$ (min): 6.95 (ESI-MS (m/z): 640.0 (M+H$^+$)). HRMS: calcd. for C$_{32}$H$_{45}$N$_7$O$_5$S [M+H]$^+$ 640.32756. found 640.32756.

N$_3$-Phe-Leu-Leu-Phe(4-NH$_2$)-EK (45b)

(SEQ ID NO:13). $^1$H NMR (400 MHz, CD$_3$OD): δ=7.36 (d, J=8.47 Hz, 2H), 7.28-7.16 (m, 9H), 4.66 (dd, J=9.33, 4.29 Hz, 1H), 4.35-4.27 (m, 2H), 4.10 (dd, J=8.46, 4.68 Hz, 1H), 3.19 (d, J=4.88 Hz, 1H), 3.15-3.10 (m, 2H), 2.98-2.88 (m, 2H), 2.73 (dd, J=8.77, 5.04 Hz, 1H), 1.56-1.42 (m, 8H), 1.38 (s, 3H), 0.90-0.82 (m, 12H) ppm. LC-MS: R$_t$ (min): 7.37 (ESI-MS (m/z): 620.20 (M+H$^+$)). HRMS: calcd. for C$_{33}$H$_{45}$N$_7$O$_5$ [M+H]$^+$ 620.35549. found 620.35532.

N$_3$-Phe-Leu-Leu-Ala(4-pyridine)-VS (46)

(SEQ ID NO:14). $^1$H NMR (400 MHz, CD$_3$OD): δ=8.62 (d, J=6.12 Hz, 2H), 7.85 (d, J=6.16 Hz, 2H), 7.21-7.06 (m, 5H), 6.81 (dd, J=15.13, 5.03 Hz, 1H), 6.62 (dd, J=15.23, 1.46 Hz, 1H), 5.00-4.93 (m, 1H), 4.20-4.14 (m, 1H), 4.10-4.04 (m, 2H), 3.31 (dd, J=13.99, 4.46 Hz, 1H), 3.11-3.03 (m, 2H), 2.88 (s, 3H), 2.86-2.82 (m, 1H), 1.51-1.08 (m, 6H), 0.80 (dd, J=7.81, 6.26 Hz, 6H), 0.75 (d, J=6.00 Hz, 6H) ppm. $^{13}$C NMR (100 MHz, CD$_3$OD): δ=174.63, 174.48, 171.74, 160.53, 145.75, 142.38, 137.86, 132.60, 130.47, 129.63, 129.45, 128.07, 65.49, 53.64, 53.55, 50.74, 42.76, 41.57, 41.45, 40.32, 38.64, 25.92, 25.80, 23.49, 23.37, 21.86, 21.80 ppm. LC-MS: $R_t$ (min): 6.86 (ESI-MS (m/z): 626.2 (M+H$^+$)). HRMS: calcd. for $C_{31}H_{43}N_7O_5S$ [M+H]$^+$626.31191. found 626.31172.

$N_3$-Phe-Leu-Leu-Lys-VS TFA salt (47)

(SEQ ID NO:15). $^1$H NMR (400 MHz, CD$_3$OD): δ=7.16-7.04 (m, 5H), 6.65 (dd, J=15.20, 5.10 Hz, 1H), 6.46 (dd, J=15.21, 1.40 Hz, 1H), 4.44 (td, J=9.60, 4.87, 4.87 Hz, 1H), 4.17 (td, J=9.78, 4.95, 4.95 Hz, 2H), 4.04 (dd, J=8.56, 4.80 Hz, 1H), 3.05 (dd, J=14.05, 4.77 Hz, 1H), 2.82 (dd, J=16.0, 8.00 Hz, 1H), 2.82 (s, 3H), 2.76 (t, J=7.42, 7.42 Hz, 2H), 1.65-1.22 (m, 12H), 0.81 (d, J=6.25 Hz, 3H), 0.76 (d, J=6.04 Hz, 6H), 0.72 (d, J=5.77 Hz, 3H) ppm. $^{13}$C NMR (100 MHz, CD$_3$OD): δ=174.72, 174.64, 171.90, 147.77, 137.79, 131.19, 130.46, 129.64, 128.10, 65.47, 53.82, 53.67, 50.53, 42.83, 41.56, 41.44, 40.54, 38.66, 33.76, 27.89, 25.97, 25.80, 23.77, 23.42, 21.99, 21.93 ppm. LC-MS: $R_t$ (min): 5.73 (ESI-MS (m/z): 606.5 (M+H$^+$)). HRMS: calcd. for $C_{29}H_{47}N_7O_5S$ [M+H]$^+$606.34321. found 606.34299.

HMB-Val-Ser-Phe (4-CH$_2$NH$_2$)-VS (48). $^1$H NMR (400 MHz, CD$_3$OD): S=7.22 (d, J=8.48 Hz, 2H), 7.19 (d, J=8.45 Hz, 2H), 6.95 (t, J=7.80 Hz, 1H), 6.77-6.69 (m, 3H), 6.65 (dd, J=15.17, 1.46 Hz, 1H), 4.81-4.76 (m, 1H), 4.29 (t, J=5.53 Hz, 1H), 4.17 (d, J=7.16 Hz, 1H), 3.90 (d, J=5.45 Hz, 2H), 3.69 (dd, J=10.78, 5.01 Hz, 1H), 3.60 (dd, J=10.76, 6.19 Hz, 1H), 2.92 (dd, J=13.83, 6.47 Hz, 1H), 2.84-2.80 (m, 1H), 2.82 (s, 3H), 2.10-2.01 (m, 1H), 2.06 (s, 3H), 0.89 (dd, J=6.67, 4.95 Hz, 6H) ppm. $^{13}$C NMR (100 MHz, CD$_3$OD): δ=174.00, 173.61, 171.83, 157.08, 146.95, 139.62, 139.11, 132.93, 131.78, 131.18, 130.18, 127.60, 123.26, 119.16, 117.19, 62.90, 61.62, 56.49, 52.60, 44.04, 42.84, 40.16, 31.40, 19.89, 19.06, 13.06 ppm. LC-MS: $R_t$ (min): 4.19 (ESI-MS (m/z): 575.20 (M+H$^+$)). HRMS: calcd. for $C_{28}H_{38}N_4O_7S$ [M+H]$^+$ 575.25340. found 575.25336.

HMB-Val-Ser-Phe(4-NH$_2$)-VS (49). $^1$H NMR (400 MHz, CD$_3$OD): δ=7.33 (d, J=8.45 Hz, 2H), 7.19 (d, J=8.46 Hz, 2H), 7.00 (t, J=7.81 Hz, 1H), 6.84-6.70 (m, 4H), 4.88-4.80 (m, 1H), 4.33 (dd, J=6.11, 5.13 Hz, 1H), 4.22 (d, J=7.14 Hz, 1H), 3.72 (dd, J=10.74, 5.01 Hz, 1H), 3.64 (dd, J=10.75, 6.27 Hz, 1H), 3.03 (dd, J=13.89, 5.94 Hz, 1H), 2.90-2.85 (m, 1H), 2.88 (s, 3H), 2.11 (s, 3H), 2.10-2.06 (m, 1H), 0.94 (t, J=6.28 Hz, 6H) ppm. $^{13}$C NMR (100 MHz, CD$_3$OD): δ=174.12, 173.55, 171.89, 157.13, 146.75, 139.97, 139.12, 132.23, 131.98, 130.63, 127.60, 124.19, 123.27, 119.14, 117.18; 62.90, 61.63, 56.46, 52.54, 42.80, 39.85, 31.40, 19.87, 19.04, 13.04 ppm. LC-MS: $R_t$ (min): 3.99 (ESI-MS (m/z): 561.07 (M+H$^+$)). HRMS: calcd. for $C_{27}H_{36}N_4O_7S$ [M+H]$^+$ 561.23775. found 561.23775.

$N_3$-Phe-Ala (4-pyridine)-Leu-Phe (4-CH$_2$NH$_2$-TFA)-VS (50)

(SEQ ID NO:16). $^1$H NMR (400 MHz, CD$_3$OD): δ ppm 8.67 (d, J=6.0 Hz, 2H), 7.79 (d, J=6.3 Hz, 2H), 7.48-7.34 (m, 4H), 7.32-7.09 (m, 5H), 6.82 (dd, J=15.2, 5.5 Hz, 1H), 6.58 (dd, J=15.2, 1.4 Hz, 1H), 4.85-4.65 (m, 2H), 4.30 (dd, J=9.9, 5.1 Hz, 1H), 4.19-4.05 (m, 1H), 4.10 (s, 2H), 3.43 (dd, J=14.0, 5.4 Hz, 1H), 3.23-3.00 (m, 4H), 2.95 (s, 3H), 3.00-2.88 (m, 1H), 1.73-1.32 (m, 3H), 0.98 (d, J=6.4 Hz, 3H), 0.92 (d, J=6.4 Hz, 3H). $^{13}$C NMR (101 MHz, CD$_3$OD): ppm 174.27, 171.64, 146.56, 143.83, 139.70, 137.62, 134.54, 133.05, 131.97, 131.34, 130.42, 130.25, 129.62, 128.82, 128.15, 65.27, 54.15, 53.76, 52.76, 44.01, 42.76, 41.87, 40.02, 38.88, 38.52, 25.88, 23.39, 21.86. HRMS calcd for [$C_{35}H_{45}N_8O_5S$]$^+$ 689.32281. found 689.32267.

$N_3$-Phe-Phe (4-NH$_2$. TFA)-Leu-Phe (4-CH$_2$NH$_2$.TFA)-VS (51)

(SEQ ID NO:17). $^1$H NMR (400 MHz, CD$_3$OD): δ ppm 7.51-7.08 (m, 13H), 6.83 (dd, J=15.2, 5.4 Hz, 1H), 6.59 (dd, J=15.2, 1.3 Hz, 1H), 4.88-4.79 (m, 1H), 4.69 (dd, J=9.9, 4.8 Hz, 1H), 4.33 (dd, J=9.8, 5.0 Hz, 1H), 4.09 (s, 2H), 4.08-3.96 (m, 1H), 3.23 (dd, J=14.1, 4.8 Hz, 1H), 3.11 (dd, J=14.0, 5.0 Hz, 1H), 3.05 (dd, J=10.3, 3.0 Hz, 2H), 3.02-2.91 (m, 1H), 2.96 (s, 3H), 2.83 (dd, J=14.0, 9.0 Hz, 1H), 1.72-1.40 (m, 3H), 0.98 (d, J=6.3 Hz, 3H), 0.92 (d, J=6.3 Hz, 3H). $^{13}$C NMR (101 MHz, CD$_3$OD): δ ppm 174.30, 172.89, 171.64, 146.60, 139.62, 139.53, 137.81, 133.03, 132.17, 131.92, 131.31, 130.91, 130.34, 130.24, 129.64, 128.11, 123.96, 65.52, 55.62, 53.71, 52.56, 44.02, 42.77, 41.82, 40.15, 38.82, 38.15, 25.88, 23.39, 21.90. HRMS calcd for [$C_{36}H_{47}N_8O_5S$]+ 703.33846 found 703.33842.

$N_3$-Phe-Phe (4-CH$_2$NH$_2$)-Leu-Phe (4-CH$_2$NH$_2$)-VS (52)
(SEQ ID NO:18). $^1$H NMR (400 MHz, CD$_3$OD): δ ppm 7.53-7.20 (m, 13H), 6.84 (dd, J=15.2, 5.3 Hz, 1H), 6.60 (dd, J=15.2, 1.4 Hz, 1H), 4.66 (dd, J=9.6, 4.9 Hz, 1H), 4.33 (dd, J=9.7, 5.0 Hz, 1H), 4.18-4.02 (m, 4H), 3.24-3.08 (m, 2H), 3.05 (d, J=7.6 Hz, 1H), 2.96 (s, 3H), 2.98-2.80 (m, 3H), 1.67-1.55 (m, 2H), 1.54-1.44 (m, 1H), 1.04-0.85 (m, 6H). $^{13}$C NMR (101 MHz, CD$_3$OD): δ ppm 174.26, 173.08, 171.72, 146.65, 139.57, 139.45, 137.83, 133.01, 132.95, 131.90, 131.28, 131.14, 130.33, 130.24, 130.11, 129.63, 128.09, 65.50, 65.43, 55.94, 53.72, 52.50, 44.01, 42.80, 41.78, 40.13, 38.85, 38.34, 30.71, 25.87, 23.38, 21.92. HRMS calcd for [$C_{37}H_{49}N_8O_5S$]$^+$717.35411 found 717.35415.

$N_3$-Phe-Phe (4-CH$_2$NH$_2$)-Leu-Phe (4-NH$_2$)—VS (53)

(SEQ ID NO:19). $^1$H NMR (400 MHz, MeOD) δ ppm 7.50-7.09 (m, 13H), 6.88 (dd, J=15.2, 5.3 Hz, 1H), 6.64 (dd, J=15.2, 1.5 Hz, 1H), 4.87 (d, J=5.6 Hz, 1H), 4.68 (dd, J=9.7, 4.8 Hz, 1H), 4.32 (dd, J=9.9, 5.0 Hz, 1H), 4.17-4.03 (m, 3H), 3.27-3.01 (m, 4H), 2.97 (s, 4H), 2.85 (dd, J=14.0, 9.2 Hz, 1H), 1.68-1.54 (m, 2H), 1.54-1.36 (m, 1H), 0.95 (dd, J=21.3, 6.3 Hz, 6H). $^{13}$C NMR (101 MHz, MeOD) δ ppm 174.39, 173.13, 171.76, 146.48, 139.75, 139.46, 137.84, 132.95, 132.30, 132.01, 131.14, 130.81, 130.33, 130.12, 129.91, 129.64, 129.20, 128.09, 126.30, 124.15, 65.47, 55.95, 53.78, 52.45, 43.99, 42.74, 41.78, 39.73, 38.86, 38.32, 25.84, 23.38, 21.87. HRMS calcd for [$C_{36}H_{47}N_8O_5S$]$^+$703.33846. found 703.33848.

$N_3$-Phe-Phe (4-CH$_2$NH$_2$)-Leu-Ala (4 pyridine)-VS (54)
(SEQ ID NO:20). $^1$H NMR (400 MHz, MeOD) δ 8.68 (d, J=5.2 Hz, 2H), 8.01-7.81 (m, 2H), 7.24 (ddt, J=32.5, 18.7, 7.6 Hz, 11H), 6.96 (dd, J=15.2, 4.9 Hz, 1H), 6.76-6.67 (m, 1H), 5.18-5.02 (m, 1H), 4.60-4.49 (m, 1H), 4.24-3.93 (m, 2H), 3.55-2.62 (m, 9H), 1.75-1.15 (m, 3H), 1.01-0.76 (m, 6H). $^{13}$C NMR (100 MHz, MeOD) δ 173.95, 172.28, 170.86, 158.22, 145.35, 142.41, 138.62, 136.97, 131.94, 131.76, 130.66, 129.94, 129.83, 129.47, 129.18, 128.65, 127.68, 65.07, 55.11, 53.15, 50.03, 43.60, 42.67, 40.94, 39.78, 38.55, 37.93, 25.33, 23.15, 21.59. HRMS calcd for [$C_{35}H_{45}N_8O_5S$]$^+$ 689.32281. found 689.32271

$N_3$-Phe-Phe(4-CH$_2$NH$_2$.TFA)-Leu-Leu-VS (55)

(SEQ ID NO:21). $^1$H NMR (400 MHz, CD$_3$OD): δ ppm 7.49-7.09 (m, 9H), 6.82 (dd, J=15.2, 5.2 Hz, 1H), 6.63 (dd, J=15.2, 1.5 Hz, 1H), 4.99-4.61 (m, 2H), 4.38 (dd, J=9.5, 5.4 Hz, 1H), 4.09 (s, 2H), 4.05 (dd, J=9.1, 4.9 Hz, 1H), 3.23-3.08 (m, 2H), 3.00 (s, 3H), 2.98-2.81 (m, 2H), 1.82-1.43 (m, 6H), 1.13-0.77 (m, 12H). $^{13}$C NMR (101 MHz, CD$_3$OD): δ ppm 172.92, 171.56, 170.18, 147.05, 138.08, 136.45, 131.50, 129.81, 129.49, 128.94, 128.68, 128.24, 126.70, 64.07, 54.24, 52.21, 47.90, 42.64, 41.83, 41.39, 40.45, 37.43, 37.13, 24.55, 24.47, 22.00, 20.61. HRMS calcd for [$C_{33}H_{48}N_7O_5S$] 654.34321 found 654.34325.

$N_3$-Phe-Phe(4-NH$_2$-TFA)-Leu-Leu-VS (56)
(SEQ ID NO:22). $^1$H NMR (400 MHz, CD$_3$OD): δ ppm 7.38 (d, J=8.4 Hz, 2H), 7.35-7.18 (m, 7H), 6.82 (dd, J=15.2, 5.2 Hz, 1H), 6.63 (dd, J=15.2, 1.5 Hz, 1H), 4.78-4.61 (m, 2H), 4.38 (dd, J=9.6, 5.4 Hz, 1H), 4.06 (dd, J=8.9, 5.0 Hz, 1H), 3.22 (dd, J=14.0, 4.9 Hz, 1H), 3.11 (dd, J=14.0, 5.0 Hz, 1H), 3.00 (s, 3H), 2.99-2.91 (m, 1H), 2.85 (dd, J=13.9, 8.9 Hz, 1H), 1.90-1.44 (m, 6H), 1.15-0.79 (m, 12H). $^{13}$C NMR (101 MHz, CD$_3$OD): δ ppm 172.96, 171.37, 170.11, 147.08, 137.83, 136.41, 130.86, 130.80, 129.79, 129.47, 128.96, 128.23, 126.70, 122.37, 64.09, 53.98, 52.23, 47.89, 41.82, 41.39, 40.46, 37.40, 36.90, 24.56, 24.47, 22.00, 20.59. HRMS calcd for [C$_{32}$H$_{46}$N$_7$O$_5$S]$^+$ 640.32756 found 640.32795.

N$_3$-Phe-Ala(4-pyridine)-Leu-Leu-VS (57)

(SEQ ID NO:23). $^1$H NMR (400 MHz, CD$_3$OD): δ ppm 8.42 (d, J=6.0 Hz, 2H), 7.39-7.16 (m, 7H), 6.81 (dd, J=15.2, 5.4 Hz, 1H), 6.63 (dd, J=15.2, 1.3 Hz, 1H), 4.78 (dd, J=9.3, 5.0 Hz, 1H), 4.72-4.65 (m, 1H), 4.38 (dd, J=9.4, 5.5 Hz, 1H), 4.09 (dd, J=8.5, 5.3 Hz, 1H), 3.25-3.18 (m, 1H), 3.12 (dd, J=14.0, 5.3 Hz, 1H), 3.00 (s, 3H), 2.98-2.82 (m, 2H), 1.80-1.42 (m, 6H), 1.07-0.90 (m, 12H). $^{13}$C NMR (101 MHz, CD$_3$OD): δ ppm 174.21, 172.33, 171.52, 149.93, 148.87, 148.40, 137.73, 130.95, 130.36, 129.60, 128.09, 126.39, 65.41, 54.48, 53.60, 49.26, 43.29, 42.80, 41.93, 38.68, 38.02, 25.94, 25.85, 23.38, 23.35, 22.05. HRMS calcd for [C$_{31}$H$_{44}$N$_7$O$_5$S]$^+$ 626.31191 found 626.31156.

N$_3$-Phe-Phe-Leu-Phe-VS (58)

(SEQ ID NO:24). $^1$H NMR (400 MHz, CDCl$_3$) δ 7.38-6.73 (m, 15H), 6.46-6.40 (m, 1H), 6.39 (d, J=7.4 Hz, 1H), 4.98-4.84 (m, 1H), 4.55 (d, J=6.9 Hz, 1H), 4.30 (d, J=5.2 Hz, 1H), 4.21-4.11 (m, 2H), 3.19 (dd, J=14.0, 4.3 Hz, 2H), 3.03-2.76 (m, 6H), 1.75-1.09 (m, 3H), 1.02-0.56 (m, 6H). $^{13}$C NMR (101 MHz, CDCl$_3$) δ 171.08, 170.67, 169.41, 146.01, 135.98, 135.53, 130.14, 129.37, 129.28, 129.12, 129.10, 128.87, 128.70, 128.66, 127.41, 127.35, 127.11, 64.97, 54.54, 52.49, 50.60, 42.69, 40.14, 39.74, 38.27, 37.28, 24.66, 22.78, 21.72. HRMS calcd for [C$_{35}$H$_{43}$N$_6$O$_5$S]$^+$ 659.30102. found 659.30113. BODIPY-triazole-Phe-Leu-Leu-Phe (4-CH$_2$NH$_2$)-VS TFA salt (39)

(SEQ ID NO:7). Compound 4a (5.68 mg, 8.69 μmol) and BODIPY-alkyne (1.5 eq., 13.0 μmol, 4.28 mg) were dissolved in a 1:1:1 mixture of H$_2$O/tBuOH/Tol (1.5 mL) and to this were added CuSO$_4$ (0.1 eq., 0.87 μmol, 0.87 μL of a 1M solution in H$_2$O) and sodium ascorbate (0.15 eq., 1.3 μmol, 1.3 μL of a 1M solution in H$_2$O) and the reaction was stirred at 80° C. for 4 hours. LC-MS analysis revealed complete consumption of the azide and formation of a single product (R$_t$ (min.): 10.41 (ESI-MS (m/z): 981.20 (M+H$^+$))), which was assigned to be the corresponding benzaldehyde. The mixture was concentrated under reduced pressure and dissolved in MeOH (1.5 mL). To this were added NH$_4$OAc (10 eq., 70 μmol, 5.4 mg) and NaCNBH$_4$ (2 eq., 15 μmol, 1.0 mg) and the reaction was stirred for 15 hours, after which LC-MS analysis indicated a complete disappearance of the aldehyde peak. The reaction was quenched by addition of aqueous HCl (100 μL, 1M) and the mixture was concentrated under reduced pressure. The title compound was obtained after RP-HPLC purification (gradient: 30%->70% ACN/0.1% aq. TFA) as a red/brown solid (yield: 2.1 mg, 2.14 μmol, 29%). $^1$H NMR (400 MHz, CD$_3$OD): δ=7.77 (s, 1H), 7.31 (d, J=7.91 Hz, 2H), 7.25 (d, J=8.08 Hz, 2H), 7.03-6.97 (m, 5H), 6.75 (dd, J=15.17, 5.40 Hz, 1H), 6.50 (dd, J=15.26, 1.28 Hz, 1H), 6.08 (s, 2H), 5.52 (dd, J=10.52, 5.15 Hz, 1H), 4.85-4.81 (m, 1H), 4.29-4.22 (m, 2H), 3.95 (s, 2H), 3.37-3.34 (m, 2H), 2.97-2.91 (m, 4H), 2.87 (s, 3H), 2.72-2.67 (m, 2H), 2.40 (s, 6H), 2.33 (s, 6H), 1.88-1.79 (m, 2H), 1.64-1.41 (m, 8H), 0.93-0.75 (m, 12H) ppm. LC-MS: R$_t$ (min): 8.42 (ESI-MS (m/z): 982.40 (M+H$^+$)). HRMS: calcd. for C$_{52}$H$_{70}$BF$_2$N$_9$O$_5$S [M+H]$^+$ 982.53545. found 982.53653.

BODIPY-triazole-Phe-Phe(4-CH$_2$NH$_2$.TFA)-Leu-Phe(4-CH$_2$NH$_2$.TFA)-VS (59)

(SEQ ID NO:25). A different procedure was used to avoid the side reaction of benzylamine conversion in benzyl aldehyde. Inhibitor 52 (3.94 mg, 4.17 μmol) was dissolved in 1:1:1 tBuOH:H$_2$O:MeCN (0.5 mL) and the solution was degassed. BODIPY-alkyne (2 mg, 6.3 μmol, 1.5 equiv.) and TBTA (2.2 mg, 4.17 μmol, 1 equiv.) were added, followed by Cu(MeCN)$_4$PF$_6$ (1.56 mg, 4.17 μmol, 1 equiv.). The mixture was stirred overnight under an argon atmosphere. EDTA (8.7 mg, 21 μmol, 5 equiv.) in H$_2$O (300 μL) was added and this mixture was directly subjected to HPLC purification (38-48% MeCN in H$_2$O+0.1% TFA) to afford the product (1.85 mg, 1.49 μmol, 36%). LC-MS: R$_t$ 6.48 min (linear gradient 10->90% MeCN+0.1% TFA, 15 min). $^1$H NMR (600 MHz, CD$_3$OD): δ ppm 7.44-7.30 (m, 4H), 7.28-7.14 (m, 4H), 7.01 (d, J=13.3 Hz, 7H), 6.78 (dd, J=15.1, 5.4 Hz, 1H), 6.55 (d, J=15.1 Hz, 1H), 6.11 (s, 2H), 5.47 (d, J=16.2 Hz, 1H), 4.60 (d, J=5.3 Hz, 1H), 4.34-4.28 (m, 1H), 4.11-3.96 (m, 4H), 3.28-2.84 (m, 6H), 2.92 (s, 3H), 2.79-2.67 (m, 2H), 2.44 (s, 6H), 2.40-2.31 (m, 8H), 1.86 (s, 2H), 1.64-1.28 (m, 7H), 0.99-0.85 (m, 6H). HRMS calcd for [C$_{56}$H$_{72}$BF$_2$N$_{10}$O$_5$S]$^+$ 1045.54635. found 1045.54639.

Example 14

Crystallization and Structure Determination

Crystals of the 20S proteasome from *S. cerevisiae* were grown in hanging drops at 24° C. (Groll, et al. (1997) *Nature* 386:463-71) and incubated for at least 12 hours with the respective compounds. The protein concentration used for crystallization was 40 mg/ml in Tris-HCl (10 mM, pH 7.5) and EDTA (1 mM). The drops contained 3 μl of protein and 2 μl of the reservoir solution, which contained 30 mM of magnesium acetate (MgAc$_2$), 100 mM of MES (pH 6.8) and 10% of 2-methyl-2,4-pentanediol (MPD). Crystals were soaked in a cryoprotecting buffer (30% MPD, 20 mM MgAc$_2$, 100 mM MES pH 6.8) and frozen in a stream of liquid nitrogen gas at 90 K (Oxford Cryo Systems) for data collection. The space group of CP:Inhibitor-complexes belong to P2$_1$ with cell dimensions of about a=135 Å, b=300 Å, c=144 Å, and β=113° (ST1). Data sets were collected using synchrotron radiation with λ=1.0 Å at the X06SA-beamline in SLS/Villingen/Switzerland. X-ray intensities and data reduction were evaluated by using the XDS program package (Kabsch (1993) *J. Appl. Cryst.* 26:795-800). The anisotropy of diffraction was corrected by an overall anisotropic temperature factor by comparing observed and calculated structure amplitudes using the program CNS (Brunger, et al. (1998) *Acta Crystallogr. D Biol. Crystallogr.* 54:905-21; Brunger (1992) Nature 355:472-5). Electron density was improved by averaging and back transforming the reflections 10 times over the two-fold non-crystallographic symmetry axis using the program package MAIN. Conventional crystallographic rigid body, positional, and temperature factor refinements were carried out with CNS using coordinates of the yeast 20S proteasome structure as a starting model (Groll, et al. (1997) supra). Topology and parameter-files for the ligand were received by Powell-minimization of their respective pdb-files using the program sybyl (Horner, et al. (2008) *J. Chem. Inform. Model* 48:2294-307) and SKETCHER in CCP4 pack (Ihlenfeldt, et al. (2009) *J. Cheminform.* 1:20). Model building of the ligand into the experimental electron density was performed using COOT (Emsley, et al. (2010) *Acta Crystallogr. D Biol. Crystallogr.* 66:486-501). Subsequent Translation/Libration/Screw (TLS) vibrational motion refinement was performed using the program REFMAC5 in CCP4 pack or CNS (Brunger, et al. (1998) supra; Brunger (1992) supra;

Vagin, et al. (2004) *Acta Crystallogr. D Biol. Crystallogr.* 60:2184-95). Ramachandran plot analysis was executed using SFCHECK in CCP4 pack (Vaguine, et al. (1999) *Acta Crystallogr. D Biol. Crystallogr.* 55:191-205). Final graphic representations of molecules were completed using the programs MOLSCRIPT, BOBSCRIPT (Esnouf (1997) *J. Mol. Graph. Model* 15:132-4, 112-3) and PyMOL (DeLano (2002) *Curr. Opin. Struct. Biol.* 12:14-20).

What is claimed is:

1. A peptide-based inhibitor of the proteasome β2/β2i site comprising the structure:

(Y)-(X4)-X3-X2-X1 (SEQ ID NO:2), wherein X1 is Phe residue or an aminosubstituted phenylalanine derivative wherein said residue or derivative comprises a carboxy-terminal epoxyketone or vinyl sulfone warhead; X2 is Leu or Ser; X3 is Leu, Val, Ser, Arg, His, Lys, Phe or an aminosubstituted phenylalanine derivative; X4 is present or absent and when present is Phe; Y is present or absent and when present is a capping group; and wherein each aminosubstituted phenylalanine derivative has a structure:

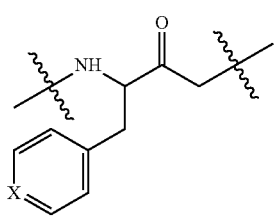

wherein X is independently N, C—NH$_2$, or C—CH$_2$—NH$_2$.

2. The peptide-based inhibitor of claim 1, wherein the capping group is a label.

3. The peptide-based inhibitor of claim 2, wherein the label comprises a 4,4-difluoro-4-bora-3a,4a-diaza-s-indacene fluorophore, a fluoroscein, a rhodamine dye or biotin.

4. A pharmaceutical composition comprising the peptide-based inhibitor of claim 1 and a pharmaceutically acceptable carrier.

5. The pharmaceutical composition of claim 4, further comprising an inhibitor of the proteasome β5/β5i site.

6. A method for inhibiting the activity of the β2/β2i site of a proteasome comprising contacting a proteasome with a peptide-based inhibitor of claim 1 so that activity of the proteasome β2/β2i site is inhibited.

7. A method for treating multiple myeloma, organ graft rejection, lupus, rheumatoid arthritis, multiple sclerosis, inflammatory bowel disease, parasitic disease, chronic obstructive pulmonary disease, psoriasis, bronchitis, emphysema or cystic fibrosis comprising administering to a subject in need of treatment an effective amount of the pharmaceutical composition of claim 4 thereby treating the multiple myeloma, organ graft rejection, lupus, rheumatoid arthritis, multiple sclerosis, inflammatory bowel disease, parasitic disease, chronic obstructive pulmonary disease, psoriasis, bronchitis, emphysema or cystic fibrosis.

8. The method of claim 7, further comprising administering an inhibitor of the proteasome β5/β5i site.

9. A method for producing the peptide-based inhibitor of claim 1, comprising
(a) protecting amine groups of arginine or an aminosubstituted phenylalanine derivative; wherein each aminosubstituted phenylalanine has a structure:

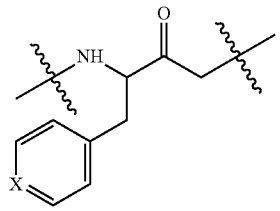

wherein X is independently N, C—H$_2$, or C—CH$_2$—NH$_2$,
(b) introducing an epoxyketone or vinyl sulfone warhead onto the arginine or aminosubstituted phenylalanine derivative, and
(c) attaching a proteasomal β2/β2i site-selective oligopeptide to the alpha amino-group of the arginine or aminosubstituted phenylalanine derivative so that a peptide-based inhibitor is produced.

10. A peptide-based inhibitor of the proteasome β2/β2i site comprising the structure:

(Y)-(X4)-X3-X2-X1 (SEQ ID NO:2), wherein X1 is an Arg or Phe residue or an aminosubstituted phenylalanine derivative wherein said residue or derivative comprises a carboxy-terminal epoxyketone or vinyl sulfone warhead; X2 is Leu or Ser; X3 is Leu, Val, Ser, Arg, His, Lys, Phe or an aminosubstituted phenylalanine derivative; X4 is Phe; Y is present or absent and when present is a capping group; and wherein each aminosubstituted phenylalanine derivative has a structure:

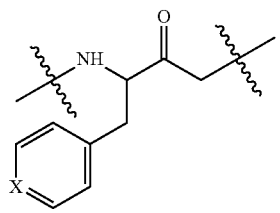

wherein X is independently N, C—NH$_2$, or C—CH$_2$—NH$_2$.

11. The peptide-based inhibitor of claim 10, wherein the capping group is a label.

12. The peptide-based inhibitor of claim 11, wherein the label comprises a 4,4-difluoro-4-bora-3a,4a-diaza-s-indacene fluorophore, a fluoroscein, a rhodamine dye or biotin.

13. A pharmaceutical composition comprising the peptide-based inhibitor of claim 10 and a pharmaceutically acceptable carrier.

14. The pharmaceutical composition of claim 13, further comprising an inhibitor of the proteasome β5/β5i site.

15. A peptide-based inhibitor of the proteasome β2/β2i site comprising the structure:

(Y)-(X4)-X3-X2-X1 (SEQ ID NO:2), wherein X1 is an Arg or Phe residue or an aminosubstituted phenylalanine derivative wherein said residue or derivative comprises a carboxy-terminal epoxyketone or vinyl sulfone warhead; X2 is Leu or Ser; X3 is Leu, Val, Ser, Arg, His, Lys, Phe or an aminosubstituted phenylalanine derivative; X4 is present or absent and when present is Phe; Y is present or absent and when present is a capping group selected from the group of an N-(3-hydroxy-2-methylbenzoyl) group, an acetyl group, a benzoyl group, an azido group, or a label; and wherein each aminosubstituted phenylalanine derivative has a structure:

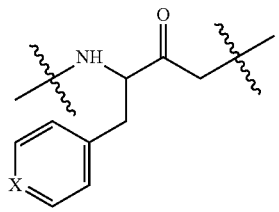

wherein X is independently N, C—NH$_2$, or C—CH$_2$—NH$_2$.

16. The peptide-based inhibitor of claim 15, wherein the label comprises a 4,4-difluoro-4-bora-3a,4a-diaza-s-indacene fluorophore, a fluoroscein, a rhodamine dye or biotin.

17. A pharmaceutical composition comprising the peptide-based inhibitor of claim 15 and a pharmaceutically acceptable carrier.

18. The pharmaceutical composition of claim 17, further comprising an inhibitor of the proteasome β5/β5i site.

* * * * *

UNITED STATES PATENT AND TRADEMARK OFFICE
CERTIFICATE OF CORRECTION

PATENT NO. : 8,609,610 B2
APPLICATION NO. : 13/723979
DATED : December 17, 2013
INVENTOR(S) : Kisselev et al.

Page 1 of 1

It is certified that error appears in the above-identified patent and that said Letters Patent is hereby corrected as shown below:

In the Claims

Column 89, line 44, delete "β2/β21"
Column 89, line 44, insert --β2/β2i--

Signed and Sealed this
Twenty-fifth Day of March, 2014

Michelle K. Lee
*Deputy Director of the United States Patent and Trademark Office*